(12) United States Patent
Mayfield et al.

(10) Patent No.: US 9,732,351 B2
(45) Date of Patent: Aug. 15, 2017

(54) CHLOROPLAST EXPRESSING COLOSTRUM OR MILK POLYPEPTIDES

(71) Applicant: The Regents of the University of California, Oakland, CA (US)

(72) Inventors: Stephen P. Mayfield, Cardiff, CA (US); Austin Hallgren, Novato, CA (US); Beth A. Rasala, San Diego, CA (US); Miller Tran, San Diego, CA (US); Michael Mayfield, Cardiff, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/135,559

(22) Filed: Apr. 22, 2016

(65) Prior Publication Data

US 2016/0257730 A1    Sep. 8, 2016

Related U.S. Application Data

(63) Continuation of application No. PCT/US2015/016460, filed on Feb. 19, 2015.

(60) Provisional application No. 61/942,024, filed on Feb. 19, 2014.

(51) Int. Cl.

| | |
|---|---|
| *C12N 15/82* | (2006.01) |
| *C07K 14/52* | (2006.01) |
| *A23K 10/18* | (2016.01) |
| *A23L 1/30* | (2006.01) |
| *A23L 2/52* | (2006.01) |
| *C07K 14/47* | (2006.01) |
| *C07K 14/475* | (2006.01) |
| *C07K 14/775* | (2006.01) |
| *C12P 21/00* | (2006.01) |
| *C07K 14/705* | (2006.01) |
| *C07K 14/76* | (2006.01) |
| *C12N 9/36* | (2006.01) |

(52) U.S. Cl.
CPC .......... *C12N 15/8257* (2013.01); *A23K 10/18* (2016.05); *A23L 1/3014* (2013.01); *A23L 2/52* (2013.01); *C07K 14/47* (2013.01); *C07K 14/475* (2013.01); *C07K 14/4705* (2013.01); *C07K 14/52* (2013.01); *C07K 14/70596* (2013.01); *C07K 14/76* (2013.01); *C07K 14/775* (2013.01); *C12N 9/2462* (2013.01); *C12N 15/8214* (2013.01); *C12P 21/00* (2013.01); *C12Y 302/01017* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,778,759 A | 10/1988 | Szalay et al. | |
| 7,678,561 B2 | 3/2010 | Mayfield | |
| RE44,266 E | 6/2013 | Mayfield | |
| 2002/0048577 A1 | 4/2002 | Bornstein et al. | |
| 2004/0022797 A1 | 2/2004 | Winslow et al. | |
| 2007/0134229 A1 | 6/2007 | Tian | |
| 2007/0298050 A1 | 12/2007 | Mayfield | |
| 2009/0098149 A1* | 4/2009 | Sayre | A23K 50/80 424/184.1 |
| 2010/0129394 A1* | 5/2010 | Mayfield | C12N 15/79 424/195.17 |
| 2010/0267139 A1 | 10/2010 | Kjems et al. | |
| 2012/0208279 A1 | 8/2012 | Vick et al. | |

FOREIGN PATENT DOCUMENTS

| | | | | |
|---|---|---|---|---|
| EP | 0 195 680 | * | 9/1986 | ............. C12N 15/00 |
| WO | WO 2015/126992 A1 | | 8/2015 | |
| WO | WO 2015/127061 A1 | | 8/2015 | |

OTHER PUBLICATIONS

Nazifi et al. Evaluation of serum and milk amyloid A in some inflammatory diseases of cattle. (2008) Iranian Journal of Veterinary Research; vol. 9, pp. 222-226.*
Larson et al. Human serum amyloid A3 peptide enhances intestinal MUC3 expression and inhibits EPEC adherence. (2003) Biochemical and Biophysical Research Communications; vol. 300; pp. 531-540.*
Blom et al. Sequence and structure-based prediction of eukaryotic protein phosphorylation sites. (1999) J. Mol. Biol.; vol. 294; pp. 1351-1362.*
Wynn et al. Minor Proteins, Including Growth Factors. (2012) in Advanced Dairy Chemistry; eds. McSweeney and Fox; pp. 317-335.*
Horiguchi et al. Production of recombinant human osteopontin using baculovirus expression systems. (2002) Bulletin of Kanagawa Dental College; vol. 30; pp. 19P-21P.*
Kerr et al. Osteopontin. (2012) UniProt P31096; pp. 1-7.*
WO patent application No. PCT/US2015/016460, International Search Report and Written Opinion mailed Jun. 26, 2015.
WO patent application No. PCT/US15/16596, International Search Report and Written Opinion mailed Jun. 9, 2015.
Artym, Jolanta et al., "Milk-derived proteins and peptides in clinical trials," *Postepy Hig Med Dosw (online)*, 2013; 67: 800-816.
Lis, Jolanta et al., "Proteins of human milk involved in immunological processes," *Postepy Hig Med Dosw (online)*, 2013; 67: 529-547, with English abstract.

(Continued)

*Primary Examiner* — Cathy Kingdon Worley
(74) *Attorney, Agent, or Firm* — Weaver Austin Villeneuve & Sampson LLP

(57) ABSTRACT

Provided are chloroplasts engineered to recombinantly express mammalian colostrum and milk polypeptides, photosynthetic organisms containing such chloroplasts, and compositions comprising such organisms and methods for producing such organisms. In certain embodiments, provided is a chloroplast comprising one or more polynucleotides encoding one or more mammalian milk or colostrum polypeptides selected from osteopontin, lactadherin, cathelicidin-1, lysozyme, lactoperoxidase, lingual antimicrobial peptide (LAP), alpha-lactalbumin, and soluble CD14.

22 Claims, 22 Drawing Sheets
(9 of 22 Drawing Sheet(s) Filed in Color)

(56) References Cited

OTHER PUBLICATIONS

Smolenski, G. et al., "Characterisation of host defence proteins in milk using a proteomic approach," *J Proteome Res*, Jan. 2007; 6(1):207-15. PubMed abstract.
U.S. Appl. No. 15/117,439, filed Aug. 8, 2016, Mayfield et al.
PCT International Preliminary Report on Patentability dated Sep. 1, 2016 issued in PCT/US2015/016460.
PCT International Preliminary Report on Patentability dated Sep. 1, 2016 issued in PCT/US2015/016596.
Ashkar et al., (1993) "In Vitro Phosphorylation of Mouse Osteopontin Expressed in *E. coli*," *Biochemical and Biophysical Research Communications*, 191(1):126-133.
Ashkar et al., (2000) "Eta-1 (Osteopontin): An Early Component of Type-1 (Cell-Mediated) Immunity," *Science*, 287(5454):860-864 [Retrieved on Nov. 29, 2016 from http://science.sciencemag.org].
Hu et al., (1995) "A Biochemical Characterization of the Binding of Osteopontin to Integrins $\alpha_v\beta_1$ and $\alpha_v\beta_5$," *The Journal of Biological Chemistry*, 270(44) Issue 3:26232-26238 [Retrieved on Dec. 14, 2016 from http://www.jbc.org].

\* cited by examiner

| Protein | Class | Function |
|---|---|---|
| mammary assoc. serum amyloid A3 | antimicrobial | Induces the expression of mucus to block pathogenic bacterial adhesion |
| osteopontin | bone strength anti-inflammatory | Extracellular matrix protein, binds calcium, major organic component of bone<br>Modulates immune function<br>Involved in wound repair |
| lysozyme C | anti-microbial | Hydrolyzes bacterial cell walls, inducing cell lysis. |
| alpha-lactalbumin | antimicrobial nutritional | Contains antimicrobial peptides<br>Prebiotic stimulation activities<br>Immuno-stimulatory effect<br>Enhances mineral absorption<br>Good source of tryptophan, first limited amino acid in infant formula |
| lactadherin | anti-inflammatory | Functions in the removal of apoptotic cells<br>Functions in intestinal epithelial homeostasis<br>Promotes mucosal healing<br>Treatment of bowel injuries |
| soluble CD14 | immuno-stimulation antimicrobial | Pattern recognition molecule that binds lipopolysaccharide (LPS) and initiates immune response to bacterial infections. |
| lingual antimicrobial peptide | antimicrobial | Broad-spectrum antimicrobial.<br>Inserts into cell membranes and causes cell lysis |
| cathelicidin-1 | antimicrobial | Broad-spectrum antimicrobial.<br>Inserts into cell membranes and causes cell lysis |

*Fig. 1*

```
atg GAT TAC AAA GAT GAT GAC GAT AAA AGT TTA CCT GTA AAA    < 42
  M   D   Y   K   D   D   D   D   K   S   L   P   V   K CCA ACA TCA TCA GGT TCA TCA GAA GAA AAA CAA TTA AAT AAT    < 84
  P   T   S   S   G   S   S   E   E   K   Q   L   N   N AAA TAT CCA GAT GCT GTT GCA ATT TGG TTA AAA CCT GAT CCA    < 126
  K   Y   P   D   A   V   A   I   W   L   K   P   D   P TCA CAA AAA CAA ACA TTT TTA ACA CCA CAA AAT TCA GTA TCA    < 168
  S   Q   K   Q   T   F   L   T   P   Q   N   S   V   S TCA GAA GAA ACA GAT GAT AAT AAA CAA AAT ACA TTA CCA TCA    < 210
  S   E   E   T   D   D   N   K   Q   N   T   L   P   S AAA TCA AAT GAA TCA CCA GAA CAA ACT GAT GAT TTA GAT GAT    < 252
  K   S   N   E   S   P   E   Q   T   D   D   L   D   D GAT GAT GAT AAT TCA CAA GAT GTT AAT TCA AAT GAT TCA GAT    < 294
  D   D   D   N   S   Q   D   V   N   S   N   D   S   D GAT GCT GAA ACA ACA GAT GAT CCT GAT CAT TCA GAT GAA TCA    < 336
  D   A   E   T   T   D   D   P   D   H   S   D   E   S CAT CAC TCA GAT GAA TCA GAT GAA GTT GAT TTT CCT ACA GAT    < 378
  H   H   S   D   E   S   D   E   V   D   F   P   T   D ATT CCA ACT ATT GCT GTT TTT ACA CCA TTT ATT CCT ACA GAA    < 420
  I   P   T   I   A   V   F   T   P   F   I   P   T   E TCA GCT AAT GAT GGT CGT GGT GAT TCA GTA GCT TAT GGT TTA    < 462
  S   A   N   D   G   R   G   D   S   V   A   Y   G   L AAA TCA CGT TCA AAA AAA TTT CGT CGT TCA AAT GTA CAA TCA    < 504
  K   S   R   S   K   K   F   R   R   S   N   V   Q   S CCA GAT GCT ACT GAA GAA GAT TTC ACA TCA CAC ATT GAA TCA    < 546
  P   D   A   T   E   E   D   F   T   S   H   I   E   S GAA GAA ATG CAC GAT GCT CCA AAA AAA ACT TCA CAA TTA ACA    < 588
  E   E   M   H   D   A   P   K   K   T   S   Q   L   T GAT CAT TCA AAA GAA ACT AAT TCA TCA GAA TTA TCA AAA GAA    < 630
  D   H   S   K   E   T   N   S   S   E   L   S   K   E TTA ACA CCA AAA GCT AAA GAT AAA AAT AAA CAT TCA AAT TTA    < 672
  L   T   P   K   A   K   D   K   N   K   H   S   N   L ATT GAA TCA CAA GAA AAT TCA AAA TTA TCA CAA GAA TTT CAT    < 714
  I   E   S   Q   E   N   S   K   L   S   Q   E   F   H TCA TTA GAA GAT AAA TTA GAT TTA GAT CAC AAA TCA GAA GAA    < 756
  S   L   E   D   K   L   D   L   D   H   K   S   E   E GAT AAA CAT TTA AAA ATT CGT ATT TCA CAT GAA TTA GAT TCA    < 798
  D   K   H   L   K   I   R   I   S   H   E   L   D   S

GCT TCA TCA GAA GTT AAT TAA    < 819
  A   S   S   E   V   N   *
```

*Fig. 2*

```
CAT ATG TGG AGT CAC CCT CAA TTC GAA AAA ACC GGT GCT ATT   < 42
 H   M   W   S   H   P   Q   F   E   K   T   G   A   I

CCA GTT AAA CAA GCA GAC TCT GGT TCA AGT GAA GAA AAA CAA   < 84
 P   V   K   Q   A   D   S   G   S   S   E   E   K   Q

TTA TAT AAT AAA TAC CCA GAT GCT GTT GCT ACA TGG TTA AAT   < 126
 L   Y   N   K   Y   P   D   A   V   A   T   W   L   N

CCT GAT CCT TCA CAA AAA CAA AAT TTA TTA GCT CCA CAA ACT   < 168
 P   D   P   S   Q   K   Q   N   L   L   A   P   Q   T

TTA CCT TCA AAA TCT AAT GAA AGT CAT GAT CAC ATG GAT GAC   < 210
 L   P   S   K   S   N   E   S   H   D   H   M   D   D

ATG GAC GAC GAA GAT GAC GAT GAC CAT GTA GAC TCT CAA GAT   < 252
 M   D   D   E   D   D   D   D   H   V   D   S   Q   D

AGT ATT GAC TCA AAT GAT TCA GAT GAC GTA GAT GAC ACT GAC   < 294
 S   I   D   S   N   D   S   D   D   V   D   D   T   D

GAC TCA CAT CAA TCA GAC GAA TCT CAT CAT AGT GAT GAA TCT   < 336
 D   S   H   Q   S   D   E   S   H   H   S   D   E   S

GAC GAA CTT GTA ACA GAT TTC CCA ACT GAT TTA CCA GCT ACT   < 378
 D   E   L   V   T   D   F   P   T   D   L   P   A   T

GAA GTT TTC ACA CCA GTA GTT CCA ACT GTT GAT ACT TAC GAC   < 420
 E   V   F   T   P   V   V   P   T   V   D   T   Y   D

GGT CGT GGT GAT TCT GTA GTT TAT GGT TTA CGT TCT AAA TCA   < 462
 G   R   G   D   S   V   V   Y   G   L   R   S   K   S

AAA AAA TTT CGT CGT CCT GAT ATT CAA TAT CCA GAC GCA ACT   < 504
 K   K   F   R   R   P   D   I   Q   Y   P   D   A   T

GAC GAA GAT ATT ACA TCA CAC ATG GAA TCT GAA GAA TTA AAT   < 546
 D   E   D   I   T   S   H   M   E   S   E   E   L   N

GGT GCT TAC AAA GCT ATT CCT GTA GCA CAA GAT TTA AAT GCT   < 588
 G   A   Y   K   A   I   P   V   A   Q   D   L   N   A

CCT TCA GAC TGG GAT TCT CGT GGT AAA GAC AGT TAC GAA ACT   < 630
 P   S   D   W   D   S   R   G   K   D   S   Y   E   T

TCA CAA CTT GAT GAT CAA AGT GCT GAA ACA CAT TCA CAC AAA   < 672
 S   Q   L   D   D   Q   S   A   E   T   H   S   H   K

CAA TCT CGT CTT TAT AAA CGT AAA GCT AAT GAT GAA AGT AAT   < 714
 Q   S   R   L   Y   K   R   K   A   N   D   E   S   N

GAA CAC TCA GAT GTT ATT GAC TCA CAA GAA CTT TCT AAA GTA   < 756
 E   H   S   D   V   I   D   S   Q   E   L   S   K   V

TCA CGT GAA TTT CAC AGT CAC GAA TTT CAT TCT CAC GAA GAT   < 798
 S   R   E   F   H   S   H   E   F   H   S   H   E   D

ATG TTA GTT GTT GAT CCA AAA AGT AAA GAA GAA GAC AAA CAC   < 840
 M   L   V   V   D   P   K   S   K   E   E   D   K   H

CTT AAA TTT CGT ATT TCT CAC GAA TTA GAC TCA GCA TCA TCT   < 882
 L   K   F   R   I   S   H   E   L   D   S   A   S   S

GAA GTT AAT TAA   < 894
 E   V   N   *
```

*Fig. 3*

```
              P  PP
              |  ||
   1<  MWSHPQFEKTGAIPVKQADSGSSEEKQLYNKYPDAVATWLNPDPSQKQNL  >50
           P P  P              P   P     P         P
           | |  |              |   |     |         |
  51<  LAPQTLPSKSNESHDHMDDMDDEDDDDHVDSQDSIDSNDSDDVDDTDDSH  >100
        P   P  P P
        |   |  | |
 101<  QSDESHHSDESDELVTDFPTDLPATEVFTPVVPTVDTYDGRGDSVVYGLR  >150
                    P       P  P                        P
                    |       |  |                        |
 151<  SKSKKFRRPDIQYPDATDEDITSHMESEELNGAYKAIPVAQDLNAPSDWD  >200
         P    P   P  P                P         P    PP
         |    |   |  |                |         |    ||
 201<  SRGKDSYETSQLDDQSAETHSHKQSRLYKRKANDESNEHSDVIDSQELSK  >250
         P    P        P            P        P PP
         |    |        |            |        | ||
 251<  VSREFHSHEFHSHEDMLVVDPKSKEEDKHLKFRISHELDSASSEVN       >296
```

*Fig. 4*

```
CAT ATG GAT TAC AAA GAT GAC GAT GAT AAA GGT ATT CCA ATT   < 42
 H   M   D   Y   K   D   D   D   D   K   G   I   P   I

AAA CAC GCA GAT AGT GGT TCA TCA GAA GAA AAA CAA TTA TAC   < 84
 K   H   A   D   S   G   S   S   E   E   K   Q   L   Y

AAC AAA TAC CCT GGT GCT GTT GCT ACA TGG TTA AAA CCA GAT   < 126
 N   K   Y   P   G   A   V   A   T   W   L   K   P   D

CCT TCA CAA AAA CAA ACA TTT TTA GCT TTA CAA AAT GCT GTT   < 168
 P   S   Q   K   Q   T   F   L   A   L   Q   N   A   V

TTA ACA GAA GAA ACT GAC GAC TTC AAA CAA AAA ACA TTT TCT   < 210
 L   T   E   E   T   D   D   F   K   Q   K   T   F   S

TCA AAA TCT AAC GAA AGT CAT GAC GAC GTT GAT GAA GAT GAT   < 252
 S   K   S   N   E   S   H   D   D   V   D   E   D   D

GGT GAT GAC GTT GAT AGT CAA GAT TCA GTT GAT TCA AAC GAC   < 294
 G   D   D   V   D   S   Q   D   S   V   D   S   N   D

TTA GAC GAT GAT TCA AAT GAA TCA GAT GAA AGT GAT GAA TTA   < 336
 L   D   D   D   S   N   E   S   D   E   S   D   E   L

GTA ACA GAT TTC CCA ACT GAT ATT CCT GCA ACT CAA TTA TTC   < 378
 V   T   D   F   P   T   D   I   P   A   T   Q   L   F

ACA CCA GCT GTT CCA ACA CGT GGT AGT TAC GAC GGT CGT GGT   < 420
 T   P   A   V   P   T   R   G   S   Y   D   G   R   G

GAT TCT GTA GCT TAT GGT TTA CGT TCA AAA TCA AAA AAA TCA   < 462
 D   S   V   A   Y   G   L   R   S   K   S   K   K   S

CAC AAA TAT GAA GTT CAA TAC CCA GAC TCA ACT GAA GAA GAT   < 504
 H   K   Y   E   V   Q   Y   P   D   S   T   E   E   D

TTT ACA TCA TTA GTA AAA TCT GCA TCA ATG GAA GAC GAC TTT   < 546
 F   T   S   L   V   K   S   A   S   M   E   D   D   F

AAT GCA GTA TTA TTA AGT CGT ACT GTT CGT GGT ACT TCA GAT   < 588
 N   A   V   L   L   S   R   T   V   R   G   T   S   D

CGT GAT TCA CAC GCT AAA GAC TCT CAA GAA ACT TCA CAA TTA   < 630
 R   D   S   H   A   K   D   S   Q   E   T   S   Q   L

GAT GAT CAT TCT ATG GAA ACT AAA GGT CGT AAA CAC TCA CAA   < 672
 D   D   H   S   M   E   T   K   G   R   K   H   S   Q

GAA TAC AAA TTA CGT GCT AGT GAC GAA TCA AAT ATG CAC AGT   < 714
 E   Y   K   L   R   A   S   D   E   S   N   M   H   S

CAC GAA ATT GGT TCA CAA GAA AAT TCT GAA GTA TCT AGT GAA   < 756
 H   E   I   G   S   Q   E   N   S   E   V   S   S   E

TTA GTT AGT CAA TTA AGT CAA TCA CAC GAA AAA GAA TTA ATT   < 798
 L   V   S   Q   L   S   Q   S   H   E   K   E   L   I

GTT GAC TCT AAA AGT GAA GAA GAA GAT AAA CAC TTA AAA TTT   < 840
 V   D   S   K   S   E   E   E   D   K   H   L   K   F

CAT GTT TCT CAC GAA TTA GAT AGT GCT TCA AGT GAA ATT AAT   < 882
 H   V   S   H   E   L   D   S   A   S   S   E   I   N taa tct aga   < 891
 *   S   R
```

*Fig. 5*

```
  1< MDYKDDDDKGIPIKHADSGSSEEKQLYNKYPGAVATWLKPDPSQKQTFLA > 50
            P  P
            |  |
 51< LQNAVLTEETDDFKQKTFSSKSNESHDDVDEDDGDDVDSQDSVDSNDLDD >100

101< DSNESDESDELVTDFPTDIPATQLFTPAVPTRGSYDGRGDSVAYGLRSKS >150
         P       PP        P P                       P
         |       ||        | |                       |
151< KKSHKYEVQYPDSTEEDFTSLVKSASMEDDFNAVLLSRTVRGTSDRDSHA >200
          P                      P P P          P
          |                      | | |          |
201< KDSQETSQLDDHSMETKGRKHSQEYKLRASDESNMHSHEIGSQENSEVSS >250
                    P    PP
                    |    ||
251< ELVSQLSQSHEKELIVDSKSEEEDKHLKFHVSHELDSASSEIN        >293
```

*Fig. 6*

```
CAT ATG GAC TAT AAA GAT GAC GAT GAT AAA GGT ATT CCA ATT   < 42
 H   M   D   Y   K   D   D   D   D   K   G   I   P   I

AAA CAA ACA GAC AGT GGA TCT AGT GAA GAA AAA CAA TTA TAT   < 84
 K   Q   T   D   S   G   S   S   E   E   K   Q   L   Y

AAC AAA TAT CCT GTT GCT GTA GCT ACT TGG CCA AAA CCA GAT   < 126
 N   K   Y   P   V   A   V   A   T   W   P   K   P   D

CCT TCT CAA AAA CAA ACT TTT TTA GCT TTA CAA AAC GCA GTT   < 168
 P   S   Q   K   Q   T   F   L   A   L   Q   N   A   V

TTA TCT GAA GAA ACA GAT GAT TTC AAA CAA AAA ACA TTA GCA   < 210
 L   S   E   E   T   D   D   F   K   Q   K   T   L   A

TCA AAA TCT AAC GAA TCA CAT GAT GTA GAT GAC GAA GAC GAT   < 252
 S   K   S   N   E   S   H   D   V   D   D   E   D   D

GAA GAC GAC GTA GAT TCT CAA GAT TCT GTT GAT TCT CAC GAT   < 294
 E   D   D   V   D   S   Q   D   S   V   D   S   H   D

ACA GAT GAT GAT AGT AAT CAA AGT GAC GAA AGT GAT GAA CTT   < 336
 T   D   D   D   S   N   Q   S   D   E   S   D   E   L

GTA ACA GAC TTT CCA ACT GAC GTA CCA GCT ACT CAA TTC TTT   < 378
 V   T   D   F   P   T   D   V   P   A   T   Q   F   F

ACA CCA GCT GTT CCA ACT CGT GAT AGT TAT GAC GGA CGT GGT   < 420
 T   P   A   V   P   T   R   D   S   Y   D   G   R   G

GAC TCT GTT GCA TAC GGT CTT CGT TCA AAA TCA AAA AAA TCA   < 462
 D   S   V   A   Y   G   L   R   S   K   S   K   K   S

CAT CGT TAC GAA GAT CAA TAT CCA GAT TCA ACA GAA GAA GAC   < 504
 H   R   Y   E   D   Q   Y   P   D   S   T   E   E   D

TTT ACA TCT TTA GTA AAA AGT CAA TCA ATG GAA GAT GAT TTT   < 546
 F   T   S   L   V   K   S   Q   S   M   E   D   D   F

AAT GCT GTA CTT TTA AGT CAT ACA GTT CGT CGT TCT CCT GAC   < 588
 N   A   V   L   L   S   H   T   V   R   R   S   P   D

CGT GAT TCA CAT GTT AAA GAT TCA CAA GAA ACT TCA CAA GTT   < 630
 R   D   S   H   V   K   D   S   Q   E   T   S   Q   V

GAT GAC CAC TCT ATG GAA ACA AAA AGT CGT AAA CAC TCT AAA   < 672
 D   D   H   S   M   E   T   K   S   R   K   H   S   K

GAA TAC AAA TTA AAA GCT TCT GAT GAA AAT AAT AAA CAC AGT   < 714
 E   Y   K   L   K   A   S   D   E   N   N   K   H   S

CAC GAA ATT GGT TCT CAA GAA TCT TCT GAC ATT TCT AGT GAA   < 756
 H   E   I   G   S   Q   E   S   S   D   I   S   S   E

TTA GTA GGT CAA ACT GTT CAA TCT AAT GAA AAA GAA CTT GTT   < 798
 L   V   G   Q   T   V   Q   S   N   E   K   E   L   V

CAA CAC CCA GAA AGT GAA GAA CAA GAT AAA CAC TTA AAA TTT   < 840
 Q   H   P   E   S   E   E   Q   D   K   H   L   K   F

CGT GTT TCA CAT GAA TTA GAT TCA GCA TCA AGT GAA GTT AAT   < 882
 R   V   S   H   E   L   D   S   A   S   S   E   V   N

TAA   < 885
 *
```

*Fig. 7*

```
  1<  MDYKDDDDKGIPIKQTDSGSSEEKQLYNKYPVAVATWPKPDPSQKQTFLA  >50

51<  LQNAVLSEETDDFKQKTLASKSNESHDVDDEDDEDDVDSQDSVDSHDTDD  >100

101<  DSNQSDESDELVTDFPTDVPATQFFTPAVPTRDSYDGRGDSVAYGLRSKS  >150
                                          P P
                                          | |
151<  KKSHRYEDQYPDSTEEDFTSLVKSQSMEDDFNAVLLSHTVRRSPDRDSHV  >200
                                       P
                                       |
201<  KDSQETSQVDDHSMETKSRKHSKEYKLKASDENNKHSHEIGSQESSDISS  >250
                                    P
                                    |
251<  ELVGQTVQSNEKELVQHPESEEQDKHLKFRVSHELDSASSEVN         >293
```

*Fig. 8*

```
atg GAT TAC AAA GAT GAT GAC GAT AAA AGT TTT TCA GGT GAT    < 42
 M   D   Y   K   D   D   D   D   K   S   F   S   G   D TTC TGT GAT TCA TCA CAA TGT TTA CAT GGT GGT ACA TGT TTA    < 84
 F   C   D   S   S   Q   C   L   H   G   G   T   C   L TTA AAT GAA GAT CGT ACT CCA CCA TTC TAT TGT TTA TGT CCT    < 126
 L   N   E   D   R   T   P   P   F   Y   C   L   C   P GAA GGT TTT ACA GGT TTA TTA TGT AAT GAA ACA GAA CAT GGT    < 168
 E   G   F   T   G   L   L   C   N   E   T   E   H   G CCA TGT TTT CCA AAT CCA TGT CAC AAT GAT GCA GAA TGT CAA    < 210
 P   C   F   P   N   P   C   H   N   D   A   E   C   Q GTT ACT GAT GAT TCA CAT CGT GGT GAT GTT TTT ATT CAA TAT    < 252
 V   T   D   D   S   H   R   G   D   V   F   I   Q   Y ATT TGT AAA TGT CCA TTA GGT TAT GTT GGT ATT CAC TGT GAA    < 294
 I   C   K   C   P   L   G   Y   V   G   I   H   C   E ACA ACA TGT ACT TCA CCT TTA GGT ATG CAA ACT GGT GCT ATT    < 336
 T   T   C   T   S   P   L   G   M   Q   T   G   A   I GCA GAT TCA CAA ATT TCA GCT TCA TCA ATG CAT TTA GGT TTT    < 378
 A   D   S   Q   I   S   A   S   S   M   H   L   G   F ATG GGT TTA CAA CGT TGG GCT CCA GAA TTA GCA CGT TTA CAC    < 420
 M   G   L   Q   R   W   A   P   E   L   A   R   L   H CAA ACA GGT ATT GTT AAT GCT TGG ACT TCA GGT AAT TAT GAT    < 462
 Q   T   G   I   V   N   A   W   T   S   G   N   Y   D AAA AAT CCT TGG ATT CAA GTT AAT TTA ATG CGT AAA ATG TGG    < 504
 K   N   P   W   I   Q   V   N   L   M   R   K   M   W GTA ACA GGT GTA GTT ACT CAA GGT GCT TCA CGT GCA GGT TCA    < 546
 V   T   G   V   V   T   Q   G   A   S   R   A   G   S GCT GAA TAT TTA AAA ACA TTC AAA GTT GCA TAT TCA ACT GAT    < 588
 A   E   Y   L   K   T   F   K   V   A   Y   S   T   D GGT CGT CAA TTC CAA TTC ATT CAA GTT GCA GGT CGT TCA GGT    < 630
 G   R   Q   F   Q   F   I   Q   V   A   G   R   S   G
```

*Fig. 9*

```
GAT AAA ATT TTT ATT GGT AAT GTT AAT AAT TCA GGT TTA AAA   < 672
 D   K   I   F   I   G   N   V   N   N   S   G   L   K

ATT AAT TTA TTC GAT ACT CCA TTA GAA ACA CAA TAT GTT CGT   < 714
 I   N   L   F   D   T   P   L   E   T   Q   Y   V   R

TTA GTT CCT ATT ATT TGT CAT CGT GGT TGT ACT TTA CGT TTT   < 756
 L   V   P   I   I   C   H   R   G   C   T   L   R   F

GAA TTA TTA GGT TGT GAA TTA AAT GGT TGT ACA GAA CCA TTA   < 798
 E   L   L   G   C   E   L   N   G   C   T   E   P   L

GGT TTA AAA GAT AAT ACA ATT CCA AAT AAA CAA ATT ACA GCT   < 840
 G   L   K   D   N   T   I   P   N   K   Q   I   T   A

TCA TCA TAT TAT AAA ACA TGG GGT TTA TCA GCT TTT TCA TGG   < 882
 S   S   Y   Y   K   T   W   G   L   S   A   F   S   W

TTT CCT TAT TAT GCT CGT TTA GAT AAT CAA GGT AAA TTT AAT   < 924
 F   P   Y   Y   A   R   L   D   N   Q   G   K   F   N

GCA TGG ACA GCT CAA ACA AAT TCA GCT TCA GAA TGG TTA CAA   < 966
 A   W   T   A   Q   T   N   S   A   S   E   W   L   Q

ATT GAT TTA GGT TCA CAA AAA CGT GTA ACA GGT ATT ATT ACA   <1008
 I   D   L   G   S   Q   K   R   V   T   G   I   I   T

CAA GGT GCA CGT GAT TTT GGT CAC ATT CAA TAT GTA GCT GCA   <1050
 Q   G   A   R   D   F   G   H   I   Q   Y   V   A   A

TAT CGT GTT GCT TAT GGT GAT GAT GGT GTT ACA TGG ACA GAA   <1092
 Y   R   V   A   Y   G   D   D   G   V   T   W   T   E

TAT AAA GAT CCT GGT GCT TCA GAA TCA AAA ATT TTT CCT GGT   <1134
 Y   K   D   P   G   A   S   E   S   K   I   F   P   G

AAT ATG GAT AAT AAT TCA CAT AAA AAA AAT ATT TTC GAA ACA   <1176
 N   M   D   N   N   S   H   K   K   N   I   F   E   T

CCT TTC CAA GCT CGT TTT GTA CGT ATT CAA CCA GTT GCT TGG   <1218
 P   F   Q   A   R   F   V   R   I   Q   P   V   A   W

CAT AAT CGT ATT ACT TTA CGT GTA GAA TTA TTA GGT TGT TAA   <1260
 H   N   R   I   T   L   R   V   E   L   L   G   C   *
```

*Fig. 9 (continued)*

```
ATG GAT TAC AAA GAT GAT GAC GAT AAA AGT CAA GCA TTA TCA    < 42
 M   D   Y   K   D   D   D   D   K   S   Q   A   L   S

TAT CGT GAA GCA GTT TTA CGT GCT GTT GAT CAA TTA AAT GAA    < 84
 Y   R   E   A   V   L   R   A   V   D   Q   L   N   E

CAA TCA TCA GAA CCT AAT ATT TAT CGT TTA TTA GAA TTA GAT    < 126
 Q   S   S   E   P   N   I   Y   R   L   L   E   L   D

CAA CCT CCA CAA GAT GAT GAA GAT CCT GAT TCA CCT AAA CGT    < 168
 Q   P   P   Q   D   D   E   D   P   D   S   P   K   R

GTA TCA TTT CGT GTT AAA GAA ACA GTT TGT TCA CGT ACA ACA    < 210
 V   S   F   R   V   K   E   T   V   C   S   R   T   T

CAA CAA CCA CCA GAA CAA TGT GAT TTC AAA GAA AAT GGT TTA    < 252
 Q   Q   P   P   E   Q   C   D   F   K   E   N   G   L

TTA AAA CGT TGT GAA GGT ACA GTA ACA TTA GAT CAA GTA CGT    < 294
 L   K   R   C   E   G   T   V   T   L   D   Q   V   R

GGT AAT TTT GAT ATT ACT TGT AAT AAT CAC CAA TCA ATT CGT    < 336
 G   N   F   D   I   T   C   N   N   H   Q   S   I   R

ATT ACA AAA CAA CCA TGG GCA CCA CCA CAA GCA GCT CGT TTA    < 378
 I   T   K   Q   P   W   A   P   P   Q   A   A   R   L

TGT CGT ATT GTT GTT ATT CGT GTT TGT CGT TAA    < 411
 C   R   I   V   V   I   R   V   C   R   *
```

*Fig. 10*

Lane 1: Negative Control
Lane 2: Chloroplast osteopontin 1
Lane 3: Chloroplast osteopontin 2
Lane 4: Chloroplast osteopontin 3
Lane 5: Chloroplast osteopontin 4
Lane 6: Chloroplast osteopontin 5

Lane 1: Negative Control
Lane 2: Chloroplast Cathelicidin 1
Lane 3: Chloroplast Cathelicidin 2
Lane 4: Chloroplast Cathelicidin 3
Lane 5: Chloroplast Cathelicidin 4

Fig. A

```
  1  MLFVKPTSSG  SSEERQLNNK  YPDAVAIWLK  FDPSQRQTEL  TPQNSVSSEE  TDDNQNTLP  SKSHESPEQP  DDLODDDNS    80
 81  QDWNSHDSDD  AETTDDPDHS  DESHHSDESD  EVDFFTDIPI  IAVFTPEIPT  ESAMDGRGDS  VAYGLKSESK  KFRRSWVQSP  160
161  DATEEDFTSH  IESEEMHDAP  KKTSQLTDHS  KETWESELSK  ELTEKAKDKN  KNSMLIESQB  NSKLSQEFHS  LEDKLDLDHE  240
241  SEEDKHLKIR  ISHELDSASS  EVN                                                                   263
```

Fig. B

| Localized Phosphorylation Sites |
|---|
| S45 |
| S47 |
| S218 |
| S230 |
| S241 |
| S252 |
| S259 |

| Ambiguous Phosphorylation Sites |
|---|
| S48 |
| T51 |
| S85 |
| S88 |
| T93 |
| T94 |
| S100 |
| S103 |
| S106 |
| S109 |
| S260 |

*Fig. 14A-B*

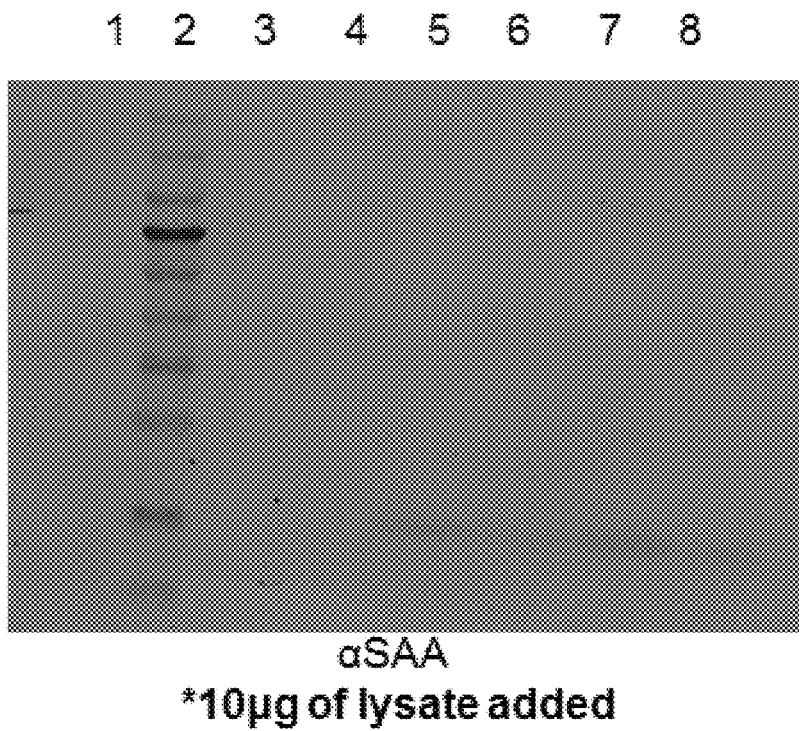
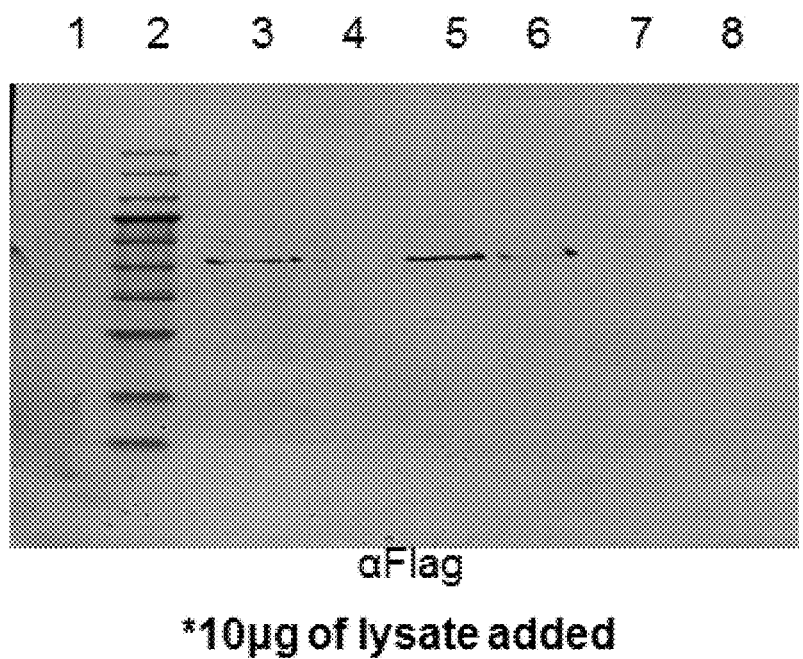
Fig. 21

SEQUENCE LISTING

<160> NUMBER OF SEQ ID NOS: 48

<210> SEQ ID NO 1
<211> LENGTH: 813
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gattacaaag atgatgacga taaaagttta cctgtaaaac caacatcatc aggttcatca      60
gaagaaaaac aattaaataa taaatatcca gatgctgttg caatttggtt aaaacctgat     120
ccatcacaaa aacaaacatt tttaacacca caaaattcag tatcatcaga agaaacagat     180
gataataaac aaaatacatt accatcaaaa tcaaatgaat caccagaaca aactgatgat     240
ttagatgatg atgatgataa ttcacaagat gttaattcaa atgattcaga tgatgctgaa     300

```
acaacagatg atcctgatca ttcagatgaa tcacatcact cagatgaatc agatgaagtt    360
gattttccta cagatattcc aactattgct gttttacac catttattcc tacagaatca     420
gctaatgatg gtcgtggtga ttcagtagct tatggtttaa aatcacgttc aaaaaaattt    480
cgtcgttcaa atgtacaatc accagatgct actgaagaag atttcacatc acacattgaa    540
tcagaagaaa tgcacgatgc tccaaaaaaa acttcacaat taacagatca ttcaaaagaa    600
actaattcat cagaattatc aaaagaatta acaccaaaag ctaaagataa aaataaacat    660
tcaaatttaa ttgaatcaca agaaaattca aaattatcac aagaatttca ttcattagaa    720
gataaattag atttagatca caaatcagaa gaagataaac atttaaaaat tcgtatttca    780
catgaattag attcagcttc atcagaagtt aat                                  813
```

```
<210> SEQ ID NO 2
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Tyr Lys Asp Asp Asp Lys Ser Leu Pro Val Lys Pro Thr Ser
1               5                   10                  15

Ser Gly Ser Ser Glu Glu Lys Gln Leu Asn Asn Lys Tyr Pro Asp Ala
                20                  25                  30

Val Ala Ile Trp Leu Lys Pro Asp Pro Ser Gln Lys Gln Thr Phe Leu
            35                  40                  45

Thr Pro Gln Asn Ser Val Ser Ser Glu Glu Thr Asp Asp Asn Lys Gln
        50                  55                  60

Asn Thr Leu Pro Ser Lys Ser Asn Glu Ser Pro Glu Gln Thr Asp Asp
65                  70                  75                  80

Leu Asp Asp Asp Asp Asn Ser Gln Asp Val Asn Ser Asn Asp Ser
                85                  90                  95

Asp Asp Ala Glu Thr Thr Asp Asp Pro Asp His Ser Asp Glu Ser His
            100                 105                 110

His Ser Asp Glu Ser Asp Glu Val Asp Phe Pro Thr Asp Ile Pro Thr
        115                 120                 125

Ile Ala Val Phe Thr Pro Phe Ile Pro Thr Glu Ser Ala Asn Asp Gly
    130                 135                 140

Arg Gly Asp Ser Val Ala Tyr Gly Leu Lys Ser Arg Ser Lys Lys Phe
145                 150                 155                 160

Arg Arg Ser Asn Val Gln Ser Pro Asp Ala Thr Glu Glu Asp Phe Thr
                165                 170                 175

Ser His Ile Glu Ser Glu Glu Met His Asp Ala Pro Lys Lys Thr Ser
            180                 185                 190

Gln Leu Thr Asp His Ser Lys Glu Thr Asn Ser Ser Glu Leu Ser Lys
        195                 200                 205

Glu Leu Thr Pro Lys Ala Lys Asp Lys Asn Lys His Ser Asn Leu Ile
    210                 215                 220

Glu Ser Gln Glu Asn Ser Lys Leu Ser Gln Glu Phe His Ser Leu Glu
225                 230                 235                 240

Asp Lys Leu Asp Leu Asp His Lys Ser Glu Glu Asp Lys His Leu Lys
                245                 250                 255

Ile Arg Ile Ser His Glu Leu Asp Ser Ala Ser Ser Glu Val Asn
```

<210> SEQ ID NO 3
<211> LENGTH: 1121
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gattacaaag atgatgacga taaaagtttt tcaggtgatt tctgtgattc atcacaatgt      60
ttacatggtg gtacatgttt attaaatgaa gatcgtactc caccattcta ttgtttatgt     120
cctgaaggtt ttacaggttt attatgtaat gaaacagaac atggtccatg ttttccaaat     180
ccatgtcaca atgatgcaga atgtcaagtt actgatgatt cacatcgtgg tgatgttttt     240
attcaatata tttgtaaatg tccattaggt tatgttggta ttcactgtga acaacatgt      300
acttcacctt taggtatgca aactggtgct attgcagatt cacaaatttc agcttcatca     360
atgcatttag gttttatggg tttacaacgt tgggctccag aattagcacg tttacaccaa     420
acaggtattg ttaatgcttg gacttcaggt aattatgata aaaatccttg gattcaagtt     480
aatttaatgc gtaaaatgtg ggtaacaggt gtagttactc aaggtgcttc acgtgcaggt     540
tcagctgaat atttaaaaac attcaaagtt gcatattcaa ctgatggtcg tcaattccaa     600
ttcattcaag ttgcaggtcg ttcaggtgat aaaatttta ttggtaatgt taataattca     660
ggtttaaaaa ttaatttatt cgatactcca ttagaaacac aatatgttcg tttagttcct     720
attatttgtc atcgtggttg tactttacgt tttgaattat taggttgtga attaaatggt     780
tgtacagaac cattaggttt aaaagataat acaattccaa ataaacaaat tacagcttca     840
tcatattata aacatggggg tttatcagct ttttcatggt ttccttatta tgctcgttta     900
gataatcaag gtaaatttaa tgcatggaca gctcaaacaa attcagcttc agaatggtta     960
caaattgatt taggttcaca aaaacgtgta acaggtatta ttacacaagg tgcacgtgat    1020
tttggtcaca ttcaatatgt agctgcatat cgtgttgctt atggtgatga tggtgttaca    1080
tggacagaat ataagatcc tggtgcttca gaatcaaaaa t                         1121
```

<210> SEQ ID NO 4
<211> LENGTH: 418
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

Asp Tyr Lys Asp Asp Asp Lys Ser Phe Ser Gly Asp Phe Cys Asp
1               5                   10                  15

Ser Ser Gln Cys Leu His Gly Gly Thr Cys Leu Leu Asn Glu Asp Arg
            20                  25                  30

Thr Pro Pro Phe Tyr Cys Leu Cys Pro Glu Gly Phe Thr Gly Leu Leu
        35                  40                  45

Cys Asn Glu Thr Glu His Gly Pro Cys Phe Pro Asn Pro Cys His Asn
    50                  55                  60

Asp Ala Glu Cys Gln Val Thr Asp Asp Ser His Arg Gly Asp Val Phe
65                  70                  75                  80

Ile Gln Tyr Ile Cys Lys Cys Pro Leu Gly Tyr Val Gly Ile His Cys
                85                  90                  95

Glu Thr Thr Cys Thr Ser Pro Leu Gly Met Gln Thr Gly Ala Ile Ala
            100                 105                 110

Asp Ser Gln Ile Ser Ala Ser Ser Met His Leu Gly Phe Met Gly Leu
        115                 120                 125

Gln Arg Trp Ala Pro Glu Leu Ala Arg Leu His Gln Thr Gly Ile Val
    130                 135                 140

Asn Ala Trp Thr Ser Gly Asn Tyr Asp Lys Asn Pro Trp Ile Gln Val
145                 150                 155                 160

Asn Leu Met Arg Lys Met Trp Val Thr Gly Val Thr Gln Gly Ala
                165                 170                 175

Ser Arg Ala Gly Ser Ala Glu Tyr Leu Lys Thr Phe Lys Val Ala Tyr
            180                 185                 190

Ser Thr Asp Gly Arg Gln Phe Gln Phe Ile Gln Val Ala Gly Arg Ser
        195                 200                 205

Gly Asp Lys Ile Phe Ile Gly Asn Val Asn Asn Ser Gly Leu Lys Ile
    210                 215                 220

Asn Leu Phe Asp Thr Pro Leu Glu Thr Gln Tyr Val Arg Leu Val Pro
225                 230                 235                 240

Ile Ile Cys His Arg Gly Cys Thr Leu Arg Phe Glu Leu Leu Gly Cys
                245                 250                 255

Glu Leu Asn Gly Cys Thr Glu Pro Leu Gly Leu Lys Asp Asn Thr Ile
            260                 265                 270

Pro Asn Lys Gln Ile Thr Ala Ser Ser Tyr Tyr Lys Thr Trp Gly Leu
        275                 280                 285

Ser Ala Phe Ser Trp Phe Pro Tyr Tyr Ala Arg Leu Asp Asn Gln Gly
    290                 295                 300

Lys Phe Asn Ala Trp Thr Ala Gln Thr Asn Ser Ala Ser Glu Trp Leu
305                 310                 315                 320

Gln Ile Asp Leu Gly Ser Gln Lys Arg Val Thr Gly Ile Ile Thr Gln
                325                 330                 335

Gly Ala Arg Asp Phe Gly His Ile Gln Tyr Val Ala Ala Tyr Arg Val
            340                 345                 350

Ala Tyr Gly Asp Asp Gly Val Thr Trp Thr Glu Tyr Lys Asp Pro Gly
        355                 360                 365

Ala Ser Glu Ser Lys Ile Phe Pro Gly Asn Met Asp Asn Asn Ser His
    370                 375                 380

Lys Lys Asn Ile Phe Glu Thr Pro Phe Gln Ala Arg Phe Val Arg Ile
385                 390                 395                 400

Gln Pro Val Ala Trp His Asn Arg Ile Thr Leu Arg Val Glu Leu Leu
                405                 410                 415

Gly Cys

<210> SEQ ID NO 5
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gattacaaag atgatgacga taaaagtcaa gcattatcat atcgtgaagc agttttacgt      60
gctgttgatc aattaaatga acaatcatca gaacctaata tttatcgttt attagaatta     120
gatcaacctc cacaagatga tgaagatcct gattcaccta aacgtgtatc atttcgtgtt     180

```
aaagaaacag tttgttcacg tacaacacaa caaccaccag aacaatgtga tttcaaagaa        240
aatggtttat taaaacgttg tgaaggtaca gtaacattag atcaagtacg tggtaattttt       300 gatattactt gtaataatca ccaatcaatt cgtattacaa acaaccatg  ggcaccacca        360 caagcagctc gtttatgtcg tattgttgtt attcgtgttt gtcgt                        405
```

<210> SEQ ID NO 6
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Asp Tyr Lys Asp Asp Asp Lys Ser Gln Ala Leu Ser Tyr Arg Glu
1               5                   10                  15

Ala Val Leu Arg Ala Val Asp Gln Leu Asn Glu Gln Ser Ser Glu Pro
            20                  25                  30

Asn Ile Tyr Arg Leu Leu Glu Leu Asp Gln Pro Pro Gln Asp Asp Glu
        35                  40                  45

Asp Pro Asp Ser Pro Lys Arg Val Ser Phe Arg Val Lys Glu Thr Val
    50                  55                  60

Cys Ser Arg Thr Thr Gln Gln Pro Pro Glu Gln Cys Asp Phe Lys Glu
65                  70                  75                  80

Asn Gly Leu Leu Lys Arg Cys Glu Gly Thr Val Thr Leu Asp Gln Val
                85                  90                  95

Arg Gly Asn Phe Asp Ile Thr Cys Asn Asn His Gln Ser Ile Arg Ile
            100                 105                 110

Thr Lys Gln Pro Trp Ala Pro Pro Gln Ala Ala Arg Leu Cys Arg Ile
        115                 120                 125

Val Val Ile Arg Val Cys Arg
    130                 135
```

<210> SEQ ID NO 7
<211> LENGTH: 789
<212> TYPE: DNA
<213> ORGANISM: Bos taurus

<400> SEQUENCE: 7

```
agtttacctg taaaaccaac atcatcaggt tcatcagaag aaaaacaatt aaataataaa        60
tatccagatg ctgttgcaat ttggttaaaa cctgatccat cacaaaaaca aacatttttta      120 acaccacaaa attcagtatc atcagaagaa acagatgata taaacaaaa tacattacca       180 tcaaaatcaa atgaatcacc agaacaaact gatgatttag atgatgatga tgataattca       240
caagatgtta attcaaatga ttcagatgat gctgaaacaa cagatgatcc tgatcattca       300
gatgaatcac atcactcaga tgaatcagat gaagttgatt tcctacaga tattccaact       360 attgctgttt ttacaccatt tattcctaca gaatcagcta atgatggtcg tggtgattca       420
gtagcttatg gtttaaaatc acgttcaaaa aaatttcgtc gttcaaatgt acaatcacca      480
gatgctactg aagaagattt cacatcacac attgaatcag aagaaatgca cgatgctcca      540
aaaaaaactt cacaattaac agatcattca aaagaaacta ttcatcaga attatcaaaa       600 gaattaacac caaaagctaa agataaaaat aaacattcaa atttaattga atcacaagaa      660
aattcaaaat tatcacaaga atttcattca ttagaagata aattagattt agatcacaaa      720
```

```
tcagaagaag ataaacattt aaaaattcgt atttcacatg aattagattc agcttcatca      780
gaagttaat                                                              789
```

<210> SEQ ID NO 8
<211> LENGTH: 263
<212> TYPE: PRT
<213> ORGANISM: Bos taurus
<220> FEATURE:
<221> NAME/KEY: MOD_RES
<222> LOCATION: (1)..(1)
<223> OTHER INFORMATION: May or may not be present
<220> FEATURE:
<223> OTHER INFORMATION: see specification as filed for detailed description of substitutions and preferred embodiments

<400> SEQUENCE: 8

```
Met Leu Pro Val Lys Pro Thr Ser Ser Gly Ser Ser Glu Glu Lys Gln
1               5                   10                  15

Leu Asn Asn Lys Tyr Pro Asp Ala Val Ala Ile Trp Leu Lys Pro Asp
            20                  25                  30

Pro Ser Gln Lys Gln Thr Phe Leu Thr Pro Gln Asn Ser Val Ser Ser
        35                  40                  45

Glu Glu Thr Asp Asp Asn Lys Gln Asn Thr Leu Pro Ser Lys Ser Asn
    50                  55                  60

Glu Ser Pro Glu Gln Thr Asp Asp Leu Asp Asp Asp Asp Asn Ser
65                  70                  75                  80

Gln Asp Val Asn Ser Asn Asp Ser Asp Ala Glu Thr Thr Asp
            85                  90                  95

Pro Asp His Ser Asp Glu Ser His His Ser Asp Glu Ser Asp Glu Val
            100                 105                 110

Asp Phe Pro Thr Asp Ile Pro Thr Ile Ala Val Phe Thr Pro Phe Ile
            115                 120                 125

Pro Thr Glu Ser Ala Asn Asp Gly Arg Gly Asp Ser Val Ala Tyr Gly
    130                 135                 140

Leu Lys Ser Arg Ser Lys Lys Phe Arg Arg Ser Asn Val Gln Ser Pro
145                 150                 155                 160

Asp Ala Thr Glu Glu Asp Phe Thr Ser His Ile Glu Ser Glu Glu Met
                165                 170                 175

His Asp Ala Pro Lys Lys Thr Ser Gln Leu Thr Asp His Ser Lys Glu
            180                 185                 190

Thr Asn Ser Ser Glu Leu Ser Lys Glu Leu Thr Pro Lys Ala Lys Asp
        195                 200                 205

Lys Asn Lys His Ser Asn Leu Ile Glu Ser Gln Glu Asn Ser Lys Leu
    210                 215                 220

Ser Gln Glu Phe His Ser Leu Glu Asp Lys Leu Asp Leu Asp His Lys
225                 230                 235                 240

Ser Glu Glu Asp Lys His Leu Lys Ile Arg Ile Ser His Glu Leu Asp
                245                 250                 255

Ser Ala Ser Ser Glu Val Asn
            260
```

<210> SEQ ID NO 9
<211> LENGTH: 1097
<212> TYPE: DNA
<213> ORGANISM: Bos taurus

<400> SEQUENCE: 9

```
agtttttcag gtgatttctg tgattcatca caatgtttac atggtggtac atgtttatta      60
```

-continued

```
aatgaagatc gtactccacc attctattgt ttatgtcctg aaggttttac aggtttatta    120
tgtaatgaaa cagaacatgg tccatgtttt ccaaatccat gtcacaatga tgcagaatgt    180
caagttactg atgattcaca tcgtggtgat gttttattc aatatatttg taaatgtcca     240
ttaggttatg ttggtattca ctgtgaaaca acatgtactt cacctttagg tatgcaaact    300
ggtgctattg cagattcaca aatttcagct tcatcaatgc atttaggttt tatgggttta    360
caacgttggg ctccagaatt agcacgttta caccaaacag gtattgttaa tgcttggact    420
tcaggtaatt atgataaaaa tccttggatt caagttaatt taatgcgtaa atgtgggta    480 acaggtgtag ttactcaagg tgcttcacgt gcaggttcag ctgaatattt aaaaacattc    540
aaagttgcat attcaactga tggtcgtcaa ttccaattca ttcaagttgc aggtcgttca    600
ggtgataaaa ttttattgg taatgttaat aattcaggtt taaaaattaa tttattcgat    660
actccattag aaacacaata tgttcgttta gttcctatta tttgtcatcg tggttgtact    720
ttacgttttg aattattagg ttgtgaatta atggttgta  cagaaccatt aggtttaaaa    780
gataatacaa ttccaaataa acaaattaca gcttcatcat attataaaac atggggttta    840
tcagcttttt catggtttcc ttattatgct cgtttagata atcaaggtaa atttaatgca    900
tggacagctc aaacaaattc agcttcagaa tggttacaaa ttgatttagg ttcacaaaaa    960
cgtgtaacag gtattattac acaaggtgca cgtgattttg gtcacattca atatgtagct   1020
gcatatcgtg ttgcttatgg tgatgatggt gttacatgga cagaatataa agatcctggt   1080
gcttcagaat caaaaat                                                   1097
```

<210> SEQ ID NO 10
<211> LENGTH: 409
<212> TYPE: PRT
<213> ORGANISM: Bos taurus

<400> SEQUENCE: 10

Phe Ser Gly Asp Phe Cys Asp Ser Ser Gln Cys Leu His Gly Gly Thr
1               5                   10                  15

Cys Leu Leu Asn Glu Asp Arg Thr Pro Pro Phe Tyr Cys Leu Cys Pro
            20                  25                  30

Glu Gly Phe Thr Gly Leu Leu Cys Asn Glu Thr Glu His Gly Pro Cys
        35                  40                  45

Phe Pro Asn Pro Cys His Asn Asp Ala Glu Cys Gln Val Thr Asp Asp
    50                  55                  60

Ser His Arg Gly Asp Val Phe Ile Gln Tyr Ile Cys Lys Cys Pro Leu
65                  70                  75                  80

Gly Tyr Val Gly Ile His Cys Glu Thr Thr Cys Thr Ser Pro Leu Gly
                85                  90                  95

Met Gln Thr Gly Ala Ile Ala Asp Ser Gln Ile Ser Ala Ser Ser Met
            100                 105                 110

His Leu Gly Phe Met Gly Leu Gln Arg Trp Ala Pro Glu Leu Ala Arg
        115                 120                 125

Leu His Gln Thr Gly Ile Val Asn Ala Trp Thr Ser Gly Asn Tyr Asp
    130                 135                 140

Lys Asn Pro Trp Ile Gln Val Asn Leu Met Arg Lys Met Trp Val Thr
145                 150                 155                 160

Gly Val Val Thr Gln Gly Ala Ser Arg Ala Gly Ser Ala Glu Tyr Leu
                165                 170                 175

Lys Thr Phe Lys Val Ala Tyr Ser Thr Asp Gly Arg Gln Phe Gln Phe

```
            180                 185                 190
Ile Gln Val Ala Gly Arg Ser Gly Asp Lys Ile Phe Ile Gly Asn Val
            195                 200                 205

Asn Asn Ser Gly Leu Lys Ile Asn Leu Phe Asp Thr Pro Leu Glu Thr
210                 215                 220

Gln Tyr Val Arg Leu Val Pro Ile Ile Cys His Arg Gly Cys Thr Leu
225                 230                 235                 240

Arg Phe Glu Leu Leu Gly Cys Glu Leu Asn Gly Cys Thr Glu Pro Leu
                245                 250                 255

Gly Leu Lys Asp Asn Thr Ile Pro Asn Lys Gln Ile Thr Ala Ser Ser
                260                 265                 270

Tyr Tyr Lys Thr Trp Gly Leu Ser Ala Phe Ser Trp Phe Pro Tyr Tyr
            275                 280                 285

Ala Arg Leu Asp Asn Gln Gly Lys Phe Asn Ala Trp Thr Ala Gln Thr
            290                 295                 300

Asn Ser Ala Ser Glu Trp Leu Gln Ile Asp Leu Gly Ser Gln Lys Arg
305                 310                 315                 320

Val Thr Gly Ile Ile Thr Gln Gly Ala Arg Asp Phe Gly His Ile Gln
                325                 330                 335

Tyr Val Ala Ala Tyr Arg Val Ala Tyr Gly Asp Asp Gly Val Thr Trp
                340                 345                 350

Thr Glu Tyr Lys Asp Pro Gly Ala Ser Glu Ser Lys Ile Phe Pro Gly
            355                 360                 365

Asn Met Asp Asn Asn Ser His Lys Lys Asn Ile Phe Glu Thr Pro Phe
370                 375                 380

Gln Ala Arg Phe Val Arg Ile Gln Pro Val Ala Trp His Asn Arg Ile
385                 390                 395                 400

Thr Leu Arg Val Glu Leu Leu Gly Cys
                405

<210> SEQ ID NO 11
<211> LENGTH: 381
<212> TYPE: DNA
<213> ORGANISM: Bos taurus

<400> SEQUENCE: 11
agtcaagcat tatcatatcg tgaagcagtt ttacgtgctg ttgatcaatt aaatgaacaa       60
tcatcagaac ctaatattta tcgtttatta gaattagatc aacctccaca agatgatgaa      120
gatcctgatt cacctaaacg tgtatcattt cgtgttaaag aaacagtttg ttcacgtaca      180
acacaacaac caccagaaca atgtgatttc aaagaaaatg gtttattaaa acgttgtgaa      240
ggtacagtaa cattagatca agtacgtggt aattttgata ttacttgtaa taatcaccaa      300
tcaattcgta ttacaaaaca accatgggca ccaccacaag cagctcgttt atgtcgtatt      360
gttgttattc gtgtttgtcg t                                                381

<210> SEQ ID NO 12
<211> LENGTH: 126
<212> TYPE: PRT
<213> ORGANISM: Bos taurus

<400> SEQUENCE: 12

Gln Ala Leu Ser Tyr Arg Glu Ala Val Leu Arg Ala Val Asp Gln Leu
1               5                   10                  15

Asn Glu Gln Ser Ser Glu Pro Asn Ile Tyr Arg Leu Leu Glu Leu Asp
                20                  25                  30
```

Gln Pro Pro Gln Asp Asp Glu Asp Pro Asp Ser Pro Lys Arg Val Ser
            35                  40                  45

Phe Arg Val Lys Glu Thr Val Cys Ser Arg Thr Thr Gln Gln Pro Pro
    50                  55                  60

Glu Gln Cys Asp Phe Lys Glu Asn Gly Leu Leu Lys Arg Cys Glu Gly
65                  70                  75                  80

Thr Val Thr Leu Asp Gln Val Arg Gly Asn Phe Asp Ile Thr Cys Asn
                85                  90                  95

Asn His Gln Ser Ile Arg Ile Thr Lys Gln Pro Trp Ala Pro Pro Gln
            100                 105                 110

Ala Ala Arg Leu Cys Arg Ile Val Val Ile Arg Val Cys Arg
        115                 120                 125

<210> SEQ ID NO 13
<211> LENGTH: 130
<212> TYPE: PRT
<213> ORGANISM: Unknown
<220> FEATURE:
<223> OTHER INFORMATION: Description of Unknown: Bovine milk lysozyme
      polypeptide

<400> SEQUENCE: 13

Lys Lys Phe Gln Arg Cys Glu Leu Ala Arg Thr Leu Lys Lys Leu Gly
1               5                   10                  15

Leu Asp Gly Tyr Arg Gly Val Ser Leu Ala Asn Trp Val Cys Leu Ala
            20                  25                  30

Arg Trp Glu Ser Asn Tyr Asn Thr Arg Ala Thr Asn Tyr Asn Arg Gly
        35                  40                  45

Asp Lys Ser Thr Asp Tyr Gly Ile Phe Gln Ile Asn Ser Arg Trp Trp
    50                  55                  60

Cys Asn Asp Gly Lys Thr Pro Lys Ala Val Asn Ala Cys Arg Ile Pro
65                  70                  75                  80

Cys Ser Ala Leu Leu Lys Asp Asp Ile Thr Gln Ala Val Ala Cys Ala
                85                  90                  95

Lys Arg Val Val Arg Asp Pro Gln Gly Ile Lys Ala Trp Val Ala Trp
            100                 105                 110

Arg Asn Lys Cys Gln Asn Arg Asp Leu Arg Ser Tyr Val Gln Gly Cys
        115                 120                 125

Arg Val
    130

<210> SEQ ID NO 14
<211> LENGTH: 123
<212> TYPE: PRT
<213> ORGANISM: Unknown
<220> FEATURE:
<223> OTHER INFORMATION: Description of Unknown: Bovine alpha-
      lactalbumin polypeptide

<400> SEQUENCE: 14

Glu Gln Leu Thr Lys Cys Glu Val Phe Arg Glu Leu Lys Asp Leu Lys
1               5                   10                  15

Gly Tyr Gly Gly Val Ser Leu Pro Glu Trp Val Cys Thr Thr Phe His
            20                  25                  30

Thr Ser Gly Tyr Asp Thr Gln Ala Ile Val Gln Asn Asn Asp Ser Thr
        35                  40                  45

Glu Tyr Gly Leu Phe Gln Ile Asn Asn Lys Ile Trp Cys Lys Asp Asp
    50                  55                  60

Gln Asn Pro His Ser Ser Asn Ile Cys Asn Ile Ser Cys Asp Lys Phe
65                  70                  75                  80

Leu Asp Asp Asp Leu Thr Asp Asp Ile Met Cys Val Lys Lys Ile Leu
                85                  90                  95

Asp Lys Val Gly Ile Asn Tyr Trp Leu Ala His Lys Ala Leu Cys Ser
            100                 105                 110

Glu Lys Leu Asp Gln Trp Leu Cys Glu Lys Leu
        115                 120

<210> SEQ ID NO 15
<211> LENGTH: 40
<212> TYPE: PRT
<213> ORGANISM: Unknown
<220> FEATURE:
<223> OTHER INFORMATION: Description of Unknown: Bovine lingual
      antimicrobial polypeptide

<400> SEQUENCE: 15

Val Arg Asn Ser Gln Ser Cys Arg Arg Asn Lys Gly Ile Cys Val Pro
1               5                   10                  15

Ile Arg Cys Pro Gly Ser Met Arg Gln Ile Gly Thr Cys Leu Gly Ala
            20                  25                  30

Gln Val Lys Cys Cys Arg Arg Lys
        35                  40

<210> SEQ ID NO 16
<211> LENGTH: 353
<212> TYPE: PRT
<213> ORGANISM: Unknown
<220> FEATURE:
<223> OTHER INFORMATION: Description of Unknown: Bovine soluble CD14
      polypeptide

<400> SEQUENCE: 16

Asp Thr Thr Glu Pro Cys Glu Leu Asp Asp Asp Phe Arg Cys Val
1               5                   10                  15

Cys Asn Phe Thr Asp Pro Lys Pro Asp Trp Ser Ser Ala Val Gln Cys
            20                  25                  30

Met Val Ala Val Glu Val Glu Ile Ser Ala Gly Gly Arg Ser Leu Glu
        35                  40                  45

Gln Phe Leu Lys Gly Ala Asp Thr Asn Pro Lys Gln Tyr Ala Asp Thr
    50                  55                  60

Ile Lys Ala Leu Arg Val Arg Arg Leu Lys Leu Gly Ala Ala Gln Val
65                  70                  75                  80

Pro Ala Gln Leu Leu Val Ala Val Leu Arg Ala Leu Gly Tyr Ser Arg
                85                  90                  95

Leu Lys Glu Leu Thr Leu Glu Asp Leu Glu Val Thr Gly Pro Thr Pro
            100                 105                 110

Pro Thr Pro Leu Glu Ala Ala Gly Pro Ala Leu Thr Thr Leu Ser Leu
        115                 120                 125

Arg Asn Val Ser Trp Thr Thr Gly Gly Ala Trp Leu Gly Glu Leu Gln
    130                 135                 140

Gln Trp Leu Lys Pro Gly Leu Arg Val Leu Asn Ile Ala Gln Ala His
145                 150                 155                 160

Ser Leu Ala Phe Pro Cys Ala Gly Leu Ser Thr Phe Glu Ala Leu Thr
                165                 170                 175

Thr Leu Asp Leu Ser Asp Asn Pro Ser Leu Gly Asp Ser Gly Leu Met
            180                 185                 190

Ala Ala Leu Cys Pro Asn Lys Phe Pro Ala Leu Gln Tyr Leu Ala Leu
        195                 200                 205

Arg Asn Ala Gly Met Glu Thr Pro Ser Gly Val Cys Ala Ala Leu Ala
210                 215                 220

Ala Ala Arg Val Gln Pro Gln Ser Leu Asp Leu Ser His Asn Ser Leu
225                 230                 235                 240

Arg Val Thr Ala Pro Gly Ala Thr Arg Cys Val Trp Pro Ser Ala Leu
                245                 250                 255

Arg Ser Leu Asn Leu Ser Phe Ala Gly Leu Glu Gln Val Pro Lys Gly
                260                 265                 270

Leu Pro Pro Lys Leu Ser Val Leu Asp Leu Ser Cys Asn Lys Leu Ser
                275                 280                 285

Arg Glu Pro Arg Arg Asp Glu Leu Pro Glu Val Asn Asp Leu Thr Leu
290                 295                 300

Asp Gly Asn Pro Phe Leu Asp Pro Gly Ala Leu Gln His Gln Asn Asp
305                 310                 315                 320

Pro Met Ile Ser Gly Val Val Pro Ala Cys Ala Arg Ser Ala Leu Thr
                325                 330                 335

Met Gly Val Ser Gly Ala Leu Ala Leu Leu Gln Gly Ala Arg Gly Phe
                340                 345                 350

Ala

<210> SEQ ID NO 17
<211> LENGTH: 858
<212> TYPE: DNA
<213> ORGANISM: Homo sapiens

<400> SEQUENCE: 17
gctattccag ttaaacaagc agactctggt tcaagtgaag aaaaacaatt atataataaa      60
tacccagatg ctgttgctac atggttaaat cctgatcctt cacaaaaaca aaatttatta    120
gctccacaaa ctttaccttc aaaatctaat gaaagtcatg atcacatgga tgacatggac    180
gacgaagatg acgatgacca tgtagactct caagatagta ttgactcaaa tgattcagat    240
gacgtagatg acactgacga ctcacatcaa tcagacgaat ctcatcatag tgatgaatct    300
gacgaacttg taacagattt cccaactgat ttaccagcta ctgaagtttt cacaccagta    360
gttccaactg ttgatactta cgacggtcgt ggtgattctg tagtttatgg tttacgttct    420
aaatcaaaaa aatttcgtcg tcctgatatt caatatccag acgcaactga cgaagatatt    480
acatcacaca tggaatctga agaattaaat ggtgcttaca agctattcc tgtagcacaa    540 gatttaaatg ctccttcaga ctgggattct cgtggtaaag acagttacga aacttcacaa    600
cttgatgatc aaagtgctga acacattca cacaaacaat ctcgtcttta taacgtaaa    660 gctaatgatg aaagtaatga acactcagat gttattgact cacaagaact ttctaaagta    720
tcacgtgaat ttcacagtca cgaatttcat tctcacgaag atatgttagt tgttgatcca    780
aaaagtaaag aagaagacaa acaccttaaa tttcgtattt ctcacgaatt agactcagca    840
tcatctgaag ttaattaa                                                 858

<210> SEQ ID NO 18
<211> LENGTH: 300
<212> TYPE: PRT
<213> ORGANISM: Homo sapiens

<400> SEQUENCE: 18

```
Met Arg Ile Ala Val Ile Cys Phe Cys Leu Gly Ile Thr Cys Ala
1               5                   10                  15

Ile Pro Val Lys Gln Ala Asp Ser Gly Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Thr Leu Pro Ser Lys Ser
    50                  55                  60

Asn Glu Ser His Asp His Met Asp Asp Met Asp Glu Asp Asp Asp
65                  70                  75                  80

Asp His Val Asp Ser Gln Asp Ser Ile Asp Ser Asn Asp Ser Asp Asp
                85                  90                  95

Val Asp Asp Thr Asp Asp Ser His Gln Ser Asp Glu Ser His His Ser
            100                 105                 110

Asp Glu Ser Asp Glu Leu Val Thr Asp Phe Pro Thr Asp Leu Pro Ala
            115                 120                 125

Thr Glu Val Phe Thr Pro Val Val Pro Thr Val Asp Thr Tyr Asp Gly
        130                 135                 140

Arg Gly Asp Ser Val Val Tyr Gly Leu Arg Ser Lys Ser Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Glu Leu Asn Gly Ala Tyr Lys Ala Ile Pro
            180                 185                 190

Val Ala Gln Asp Leu Asn Ala Pro Ser Asp Trp Asp Ser Arg Gly Lys
        195                 200                 205

Asp Ser Tyr Glu Thr Ser Gln Leu Asp Asp Gln Ser Ala Glu Thr His
    210                 215                 220

Ser His Lys Gln Ser Arg Leu Tyr Lys Arg Lys Ala Asn Asp Glu Ser
225                 230                 235                 240

Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
            260                 265                 270

Val Asp Pro Lys Ser Lys Glu Glu Asp Lys His Leu Lys Phe Arg Ile
        275                 280                 285

Ser His Glu Leu Asp Ser Ala Ser Ser Glu Val Asn
    290                 295                 300

<210> SEQ ID NO 19
<211> LENGTH: 861
<212> TYPE: DNA
<213> ORGANISM: Canis familiaris

<400> SEQUENCE: 19
ggtattccaa ttaaacacgc agatagtggt tcatcagaag aaaaacaatt atacaacaaa      60
taccctggtg ctgttgctac atggttaaaa ccagatcctt cacaaaaaca acatttttta    120
gctttacaaa atgctgtttt aacagaagaa actgacgact caaacaaaa aacatttctct    180 tcaaaatcta acgaaagtca tgacgacgtt gatgaagatg atggtgatga cgttgatagt    240
caagattcag ttgattcaaa cgacttagac gatgattcaa atgaatcaga tgaaagtgat    300
gaattagtaa cagatttccc aactgatatt cctgcaactc aattattcac accagctgtt    360
ccaacacgtg gtagttacga cggtcgtggt gattctgtag cttatggttt acgttcaaaa    420
```

```
tcaaaaaaat cacacaaata tgaagttcaa tacccagact caactgaaga agattttaca    480
tcattagtaa aatctgcatc aatggaagac gactttaatg cagtattatt aagtcgtact    540
gttcgtggta cttcagatcg tgattcacac gctaaagact ctcaagaaac ttcacaatta    600
gatgatcatt ctatggaaac taaaggtcgt aaacactcac aagaatacaa attacgtgct    660
agtgacgaat caaatatgca cagtcacgaa attggttcac aagaaaattc tgaagtatct    720
agtgaattag ttagtcaatt aagtcaatca cacgaaaaag aattaattgt tgactctaaa    780
agtgaagaag aagataaaca cttaaaattt catgtttctc acgaattaga tagtgcttca    840
agtgaaatta attaatctag a                                              861
```

<210> SEQ ID NO 20
<211> LENGTH: 299
<212> TYPE: PRT
<213> ORGANISM: Canis familiaris
<220> FEATURE:
<221> NAME/KEY: MOD_RES
<222> LOCATION: (1)..(1)
<223> OTHER INFORMATION: May or may not be present
<220> FEATURE:
<223> OTHER INFORMATION: see specification as filed for detailed
      description of substitutions and preferred embodiments

<400> SEQUENCE: 20

```
Met Arg Ile Ala Val Ile Cys Phe Cys Leu Leu Gly Ile Ala Tyr Ala
1               5                   10                  15

Ile Pro Ile Lys His Ala Asp Ser Gly Ser Ser Glu Glu Lys Gln Leu
            20                  25                  30

Tyr Asn Lys Tyr Pro Gly Ala Val Ala Thr Trp Leu Lys Pro Asp Pro
        35                  40                  45

Ser Gln Lys Gln Thr Phe Leu Ala Leu Gln Asn Ala Val Leu Thr Glu
    50                  55                  60

Glu Thr Asp Asp Phe Lys Gln Lys Thr Phe Ser Ser Lys Ser Asn Glu
65                  70                  75                  80

Ser His Asp Asp Val Asp Glu Asp Gly Asp Asp Val Asp Ser Gln
                85                  90                  95

Asp Ser Val Asp Ser Asn Asp Leu Asp Asp Ser Asn Glu Ser Asp
            100                 105                 110

Glu Ser Asp Glu Leu Val Thr Asp Phe Pro Thr Asp Ile Pro Ala Thr
        115                 120                 125

Gln Leu Phe Thr Pro Ala Val Pro Thr Arg Gly Ser Tyr Asp Gly Arg
    130                 135                 140

Gly Asp Ser Val Ala Tyr Gly Leu Arg Ser Lys Ser Lys Lys Ser His
145                 150                 155                 160

Lys Tyr Glu Val Gln Tyr Pro Asp Ser Thr Glu Glu Asp Phe Thr Ser
                165                 170                 175

Leu Val Lys Ser Ala Ser Met Glu Asp Asp Phe Asn Ala Val Leu Leu
            180                 185                 190

Ser Arg Thr Val Arg Gly Thr Ser Asp Arg Asp Ser His Ala Lys Asp
        195                 200                 205

Ser Gln Glu Thr Ser Gln Leu Asp Asp His Ser Met Glu Thr Lys Gly
    210                 215                 220

Arg Lys His Ser Gln Glu Tyr Lys Leu Arg Ala Ser Asp Glu Ser Asn
225                 230                 235                 240

Met His Ser His Glu Ile Gly Ser Gln Glu Asn Ser Glu Val Ser Ser
                245                 250                 255
```

```
Glu Leu Val Ser Gln Leu Ser Gln Ser His Glu Lys Glu Leu Ile Val
            260                 265                 270

Asp Ser Lys Ser Glu Glu Glu Asp Lys His Leu Lys Phe His Val Ser
        275                 280                 285

His Glu Leu Asp Ser Ala Ser Ser Glu Ile Asn
    290                 295
```

```
<210> SEQ ID NO 21
<211> LENGTH: 855
<212> TYPE: DNA
<213> ORGANISM: Felis catus

<400> SEQUENCE: 21
ggtattccaa ttaaacaaac agacagtgga tctagtgaag aaaaacaatt atataacaaa      60
tatcctgttg ctgtagctac ttggccaaaa ccagatcctt ctcaaaaaca aactttttta     120
gctttacaaa acgcagtttt atctgaagaa acagatgatt tcaaacaaaa acattagca     180
tcaaaatcta acgaatcaca tgatgtagat gacgaagacg atgaagacga cgtagattct     240
caagattctg ttgattctca cgatacagat gatgatagta atcaaagtga cgaaagtgat     300
gaacttgtaa cagactttcc aactgacgta ccagctactc aattctttac accagctgtt     360
ccaactcgtg atagttatga cggacgtggt gactctgttg catacggtct tcgttcaaaa     420
tcaaaaaaat cacatcgtta cgaagatcaa tatccagatt caacagaaga agactttaca     480
tctttagtaa aagtcaatc aatggaagat gattttaatg ctgtactttt aagtcataca     540
gttcgtcgtt ctcctgaccg tgattcacat gttaaagatt cacaagaaac ttcacaagtt     600
gatgaccact ctatggaaac aaaaagtcgt aaacactcta agaatacaa attaaaagct     660
tctgatgaaa ataataaaca cagtcacgaa attggttctc aagaatcttc tgacatttct     720
agtgaattag taggtcaaac tgttcaatct aatgaaaaag aacttgttca cacccagaa     780
agtgaagaac aagataaaca cttaaaattt cgtgtttcac atgaattaga ttcagcatca     840
agtgaagtta attaa                                                      855

<210> SEQ ID NO 22
<211> LENGTH: 299
<212> TYPE: PRT
<213> ORGANISM: Felis catus
<220> FEATURE:
<221> NAME/KEY: MOD_RES
<222> LOCATION: (1)..(1)
<223> OTHER INFORMATION: May or may not be present
<220> FEATURE:
<223> OTHER INFORMATION: see specification as filed for detailed
      description of substitutions and preferred embodiments

<400> SEQUENCE: 22

Met Arg Ile Ala Val Ile Cys Phe Cys Leu Leu Gly Ile Ala Tyr Ala
1               5                   10                  15

Ile Pro Ile Lys Gln Thr Asp Ser Gly Ser Ser Glu Glu Lys Gln Leu
            20                  25                  30

Tyr Asn Lys Tyr Pro Val Ala Val Ala Thr Trp Pro Lys Pro Asp Pro
        35                  40                  45

Ser Gln Lys Gln Thr Phe Leu Ala Leu Gln Asn Ala Val Leu Ser Glu
    50                  55                  60

Glu Thr Asp Asp Phe Lys Gln Lys Thr Leu Ala Ser Lys Ser Asn Glu
65                  70                  75                  80

Ser His Asp Val Asp Asp Glu Asp Glu Asp Val Asp Ser Gln
                85                  90                  95
```

```
Asp Ser Val Asp Ser His Asp Thr Asp Asp Ser Asn Gln Ser Asp
            100                 105                 110

Glu Ser Asp Glu Leu Val Thr Asp Phe Pro Thr Asp Val Pro Ala Thr
        115                 120                 125

Gln Phe Phe Thr Pro Ala Val Pro Thr Arg Asp Ser Tyr Asp Gly Arg
    130                 135                 140

Gly Asp Ser Val Ala Tyr Gly Leu Arg Ser Lys Ser Lys Lys Ser His
145                 150                 155                 160

Arg Tyr Glu Asp Gln Tyr Pro Asp Ser Thr Glu Asp Phe Thr Ser
                165                 170                 175

Leu Val Lys Ser Gln Ser Met Glu Asp Phe Asn Ala Val Leu Leu
        180                 185                 190

Ser His Thr Val Arg Arg Ser Pro Asp Arg Asp Ser His Val Lys Asp
            195                 200                 205

Ser Gln Glu Thr Ser Gln Val Asp Asp His Ser Met Glu Thr Lys Ser
    210                 215                 220

Arg Lys His Ser Lys Glu Tyr Lys Leu Lys Ala Ser Asp Glu Asn Asn
225                 230                 235                 240

Lys His Ser His Glu Ile Gly Ser Gln Glu Ser Ser Asp Ile Ser Ser
                245                 250                 255

Glu Leu Val Gly Gln Thr Val Gln Ser Asn Glu Lys Glu Leu Val Gln
            260                 265                 270

His Pro Glu Ser Glu Glu Gln Asp Lys His Leu Lys Phe Arg Val Ser
        275                 280                 285

His Glu Leu Asp Ser Ala Ser Ser Glu Val Asn
    290                 295

<210> SEQ ID NO 23
<211> LENGTH: 111
<212> TYPE: DNA
<213> ORGANISM: Unknown
<220> FEATURE:
<223> OTHER INFORMATION: Description of Unknown: Plastid retention
      polynucleotide

<400> SEQUENCE: 23
atggccgtca tgatgcgcac ccaggcgccc gctgccactc gcgcttcatc gcgcgtcgct      60
gttgccgctc gcccggctgc tcgccgcgcc gtggtggtcc gcgccgaggc t             111

<210> SEQ ID NO 24
<211> LENGTH: 37
<212> TYPE: PRT
<213> ORGANISM: Unknown
<220> FEATURE:
<223> OTHER INFORMATION: Description of Unknown: Plastid retention
      polypeptide

<400> SEQUENCE: 24

Met Ala Val Met Met Arg Thr Gln Ala Pro Ala Thr Arg Ala Ser
1               5                   10                  15

Ser Arg Val Ala Val Ala Ala Arg Pro Ala Ala Arg Arg Ala Val Val
            20                  25                  30

Val Arg Ala Glu Ala
        35

<210> SEQ ID NO 25
<211> LENGTH: 4
<212> TYPE: PRT
```

<213> ORGANISM: Unknown
<220> FEATURE:
<223> OTHER INFORMATION: Description of Unknown: "DEAD" box motif
      peptide

<400> SEQUENCE: 25

Asp Glu Ala Asp
1

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtgctaggta actaacgttt gattttt                                          27

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctgaatcacc acgaccatca ttagc                                            25

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccgaactgag gttgggttta                                                  20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gggggagcga ataggattag                                                  20

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcttcacgta cttggtcacg tgtcatacc                                        29

<210> SEQ ID NO 31
<211> LENGTH: 26
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 31
cctgaagtcc aagcattaac aatacc                                          26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggaaggggag gacgtaggta cataaa                                          26

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttagaacgtg ttttgttccc aat                                             23

<210> SEQ ID NO 34
<211> LENGTH: 819
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(816)

<400> SEQUENCE: 34 atg gat tac aaa gat gat gac gat aaa agt tta cct gta aaa cca aca        48
Met Asp Tyr Lys Asp Asp Asp Asp Lys Ser Leu Pro Val Lys Pro Thr
1               5                   10                  15 tca tca ggt tca tca gaa gaa aaa caa tta aat aat aaa tat cca gat        96
Ser Ser Gly Ser Ser Glu Glu Lys Gln Leu Asn Asn Lys Tyr Pro Asp
                20                  25                  30 gct gtt gca att tgg tta aaa cct gat cca tca caa aaa caa aca ttt       144
Ala Val Ala Ile Trp Leu Lys Pro Asp Pro Ser Gln Lys Gln Thr Phe
            35                  40                  45 tta aca cca caa aat tca gta tca tca gaa gaa aca gat gat aat aaa       192
Leu Thr Pro Gln Asn Ser Val Ser Ser Glu Glu Thr Asp Asp Asn Lys
        50                  55                  60 caa aat aca tta cca tca aaa tca aat gaa tca cca gaa caa act gat       240
Gln Asn Thr Leu Pro Ser Lys Ser Asn Glu Ser Pro Glu Gln Thr Asp
65                  70                  75                  80 gat tta gat gat gat gat gat aat tca caa gat gtt aat tca aat gat       288
Asp Leu Asp Asp Asp Asp Asp Asn Ser Gln Asp Val Asn Ser Asn Asp
                85                  90                  95 tca gat gat gct gaa aca aca gat gat cct gat cat tca gat gaa tca       336
Ser Asp Asp Ala Glu Thr Thr Asp Asp Pro Asp His Ser Asp Glu Ser
                100                 105                 110 cat cac tca gat gaa tca gat gaa gtt gat ttt cct aca gat att cca       384
His His Ser Asp Glu Ser Asp Glu Val Asp Phe Pro Thr Asp Ile Pro
```

```
                    115                 120                 125
act att gct gtt ttt aca cca ttt att cct aca gaa tca gct aat gat    432
Thr Ile Ala Val Phe Thr Pro Phe Ile Pro Thr Glu Ser Ala Asn Asp
        130                 135                 140 ggt cgt ggt gat tca gta gct tat ggt tta aaa tca cgt tca aaa aaa    480
Gly Arg Gly Asp Ser Val Ala Tyr Gly Leu Lys Ser Arg Ser Lys Lys
145                 150                 155                 160 ttt cgt cgt tca aat gta caa tca cca gat gct act gaa gaa gat ttc    528
Phe Arg Arg Ser Asn Val Gln Ser Pro Asp Ala Thr Glu Glu Asp Phe
                165                 170                 175 aca tca cac att gaa tca gaa gaa atg cac gat gct cca aaa aaa act    576
Thr Ser His Ile Glu Ser Glu Glu Met His Asp Ala Pro Lys Lys Thr
            180                 185                 190 tca caa tta aca gat cat tca aaa gaa act aat tca tca gaa tta tca    624
Ser Gln Leu Thr Asp His Ser Lys Glu Thr Asn Ser Ser Glu Leu Ser
        195                 200                 205 aaa gaa tta aca cca aaa gct aaa gat aaa aat aaa cat tca aat tta    672
Lys Glu Leu Thr Pro Lys Ala Lys Asp Lys Asn Lys His Ser Asn Leu
    210                 215                 220 att gaa tca caa gaa aat tca aaa tta tca caa gaa ttt cat tca tta    720
Ile Glu Ser Gln Glu Asn Ser Lys Leu Ser Gln Glu Phe His Ser Leu
225                 230                 235                 240 gaa gat aaa tta gat tta gat cac aaa tca gaa gaa gat aaa cat tta    768
Glu Asp Lys Leu Asp Leu Asp His Lys Ser Glu Glu Asp Lys His Leu
                245                 250                 255 aaa att cgt att tca cat gaa tta gat tca gct tca tca gaa gtt aat    816
Lys Ile Arg Ile Ser His Glu Leu Asp Ser Ala Ser Ser Glu Val Asn
            260                 265                 270 taa                                                                 819
```

<210> SEQ ID NO 35
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Met Asp Tyr Lys Asp Asp Asp Lys Ser Leu Pro Val Lys Pro Thr
1               5                   10                  15

Ser Ser Gly Ser Ser Glu Glu Lys Gln Leu Asn Asn Lys Tyr Pro Asp
                20                  25                  30

Ala Val Ala Ile Trp Leu Lys Pro Asp Pro Ser Gln Lys Gln Thr Phe
            35                  40                  45

Leu Thr Pro Gln Asn Ser Val Ser Ser Glu Glu Thr Asp Asp Asn Lys
        50                  55                  60

Gln Asn Thr Leu Pro Ser Lys Ser Asn Glu Ser Pro Glu Gln Thr Asp
65                  70                  75                  80

Asp Leu Asp Asp Asp Asp Asn Ser Gln Asp Val Asn Ser Asn Asp
                85                  90                  95

Ser Asp Asp Ala Glu Thr Thr Asp Asp Pro Asp His Ser Asp Glu Ser
            100                 105                 110

His His Ser Asp Glu Ser Asp Glu Val Asp Phe Pro Thr Asp Ile Pro
        115                 120                 125

Thr Ile Ala Val Phe Thr Pro Phe Ile Pro Thr Glu Ser Ala Asn Asp
    130                 135                 140

Gly Arg Gly Asp Ser Val Ala Tyr Gly Leu Lys Ser Arg Ser Lys Lys
```

```
                    145                 150                 155                 160
                Phe Arg Arg Ser Asn Val Gln Ser Pro Asp Ala Thr Glu Glu Asp Phe
                                165                 170                 175

Thr Ser His Ile Glu Ser Glu Met His Asp Ala Pro Lys Lys Thr
                                180                 185                 190

Ser Gln Leu Thr Asp His Ser Lys Glu Thr Asn Ser Ser Glu Leu Ser
                                195                 200                 205

Lys Glu Leu Thr Pro Lys Ala Lys Asp Lys Asn Lys His Ser Asn Leu
                                210                 215                 220

Ile Glu Ser Gln Glu Asn Ser Lys Leu Ser Gln Glu Phe His Ser Leu
                225                 230                 235                 240

Glu Asp Lys Leu Asp Leu Asp His Lys Ser Glu Asp Lys His Leu
                                245                 250                 255

Lys Ile Arg Ile Ser His Glu Leu Asp Ser Ala Ser Ser Glu Val Asn
                                260                 265                 270

<210> SEQ ID NO 36
<211> LENGTH: 894
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(891)

<400> SEQUENCE: 36 cat atg tgg agt cac cct caa ttc gaa aaa acc ggt gct att cca gtt        48
His Met Trp Ser His Pro Gln Phe Glu Lys Thr Gly Ala Ile Pro Val
1               5                   10                  15 aaa caa gca gac tct ggt tca agt gaa gaa aaa caa tta tat aat aaa        96
Lys Gln Ala Asp Ser Gly Ser Ser Glu Glu Lys Gln Leu Tyr Asn Lys
            20                  25                  30 tac cca gat gct gtt gct aca tgg tta aat cct gat cct tca caa aaa       144
Tyr Pro Asp Ala Val Ala Thr Trp Leu Asn Pro Asp Pro Ser Gln Lys
        35                  40                  45 caa aat tta tta gct cca caa act tta cct tca aaa tct aat gaa agt       192
Gln Asn Leu Leu Ala Pro Gln Thr Leu Pro Ser Lys Ser Asn Glu Ser
    50                  55                  60 cat gat cac atg gat gac atg gac gac gaa gat gac gat gac cat gta       240
His Asp His Met Asp Asp Met Asp Asp Glu Asp Asp Asp Asp His Val
65                  70                  75                  80 gac tct caa gat agt att gac tca aat gat tca gat gac gta gat gac       288
Asp Ser Gln Asp Ser Ile Asp Ser Asn Asp Ser Asp Asp Val Asp Asp
                85                  90                  95 act gac gac tca cat caa tca gac gaa tct cat cat agt gat gaa tct       336
Thr Asp Asp Ser His Gln Ser Asp Glu Ser His His Ser Asp Glu Ser
            100                 105                 110 gac gaa ctt gta aca gat ttc cca act gat tta cca gct act gaa gtt       384
Asp Glu Leu Val Thr Asp Phe Pro Thr Asp Leu Pro Ala Thr Glu Val
        115                 120                 125 ttc aca cca gta gtt cca act gtt gat act tac gac ggt cgt ggt gat       432
Phe Thr Pro Val Val Pro Thr Val Asp Thr Tyr Asp Gly Arg Gly Asp
    130                 135                 140 tct gta gtt tat ggt tta cgt tct aaa tca aaa aaa ttt cgt cgt cct       480
Ser Val Val Tyr Gly Leu Arg Ser Lys Ser Lys Lys Phe Arg Arg Pro
145                 150                 155                 160 gat att caa tat cca gac gca act gac gaa gat att aca tca cac atg       528
Asp Ile Gln Tyr Pro Asp Ala Thr Asp Glu Asp Ile Thr Ser His Met
```

```
                       165                 170                 175
gaa tct gaa gaa tta aat ggt gct tac aaa gct att cct gta gca caa    576
Glu Ser Glu Glu Leu Asn Gly Ala Tyr Lys Ala Ile Pro Val Ala Gln
            180                 185                 190 gat tta aat gct cct tca gac tgg gat tct cgt ggt aaa gac agt tac    624
Asp Leu Asn Ala Pro Ser Asp Trp Asp Ser Arg Gly Lys Asp Ser Tyr
        195                 200                 205 gaa act tca caa ctt gat gat caa agt gct gaa aca cat tca cac aaa    672
Glu Thr Ser Gln Leu Asp Asp Gln Ser Ala Glu Thr His Ser His Lys
    210                 215                 220 caa tct cgt ctt tat aaa cgt aaa gct aat gat gaa agt aat gaa cac    720
Gln Ser Arg Leu Tyr Lys Arg Lys Ala Asn Asp Glu Ser Asn Glu His
225                 230                 235                 240 tca gat gtt att gac tca caa gaa ctt tct aaa gta tca cgt gaa ttt    768
Ser Asp Val Ile Asp Ser Gln Glu Leu Ser Lys Val Ser Arg Glu Phe
            245                 250                 255 cac agt cac gaa ttt cat tct cac gaa gat atg tta gtt gtt gat cca    816
His Ser His Glu Phe His Ser His Glu Asp Met Leu Val Val Asp Pro
        260                 265                 270 aaa agt aaa gaa gaa gac aaa cac ctt aaa ttt cgt att tct cac gaa    864
Lys Ser Lys Glu Glu Asp Lys His Leu Lys Phe Arg Ile Ser His Glu
    275                 280                 285 tta gac tca gca tca tct gaa gtt aat taa                            894
Leu Asp Ser Ala Ser Ser Glu Val Asn
    290                 295
```

<210> SEQ ID NO 37
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
His Met Trp Ser His Pro Gln Phe Glu Lys Thr Gly Ala Ile Pro Val
1               5                   10                  15

Lys Gln Ala Asp Ser Gly Ser Ser Glu Glu Lys Gln Leu Tyr Asn Lys
            20                  25                  30

Tyr Pro Asp Ala Val Ala Thr Trp Leu Asn Pro Asp Pro Ser Gln Lys
        35                  40                  45

Gln Asn Leu Leu Ala Pro Gln Thr Leu Pro Ser Lys Ser Asn Glu Ser
    50                  55                  60

His Asp His Met Asp Asp Met Asp Asp Glu Asp Asp Asp His Val
65                  70                  75                  80

Asp Ser Gln Asp Ser Ile Asp Ser Asn Asp Ser Asp Val Asp
                85                  90                  95

Thr Asp Asp Ser His Gln Ser Asp Glu Ser His His Ser Asp Glu Ser
                100                 105                 110

Asp Glu Leu Val Thr Asp Phe Pro Thr Asp Leu Pro Ala Thr Glu Val
            115                 120                 125

Phe Thr Pro Val Val Pro Thr Val Asp Thr Tyr Asp Gly Arg Gly Asp
        130                 135                 140

Ser Val Val Tyr Gly Leu Arg Ser Lys Ser Lys Lys Phe Arg Arg Pro
145                 150                 155                 160

Asp Ile Gln Tyr Pro Asp Ala Thr Asp Glu Asp Ile Thr Ser His Met
                165                 170                 175

Glu Ser Glu Glu Leu Asn Gly Ala Tyr Lys Ala Ile Pro Val Ala Gln
```

```
                180                 185                 190
Asp Leu Asn Ala Pro Ser Asp Trp Asp Ser Arg Gly Lys Asp Ser Tyr
            195                 200                 205

Glu Thr Ser Gln Leu Asp Asp Gln Ser Ala Glu Thr His Ser His Lys
        210                 215                 220

Gln Ser Arg Leu Tyr Lys Arg Lys Ala Asn Asp Glu Ser Asn Glu His
225                 230                 235                 240

Ser Asp Val Ile Asp Ser Gln Glu Leu Ser Lys Val Ser Arg Glu Phe
                245                 250                 255

His Ser His Glu Phe His Ser His Glu Asp Met Leu Val Val Asp Pro
            260                 265                 270

Lys Ser Lys Glu Glu Asp Lys His Leu Lys Phe Arg Ile Ser His Glu
        275                 280                 285

Leu Asp Ser Ala Ser Ser Glu Val Asn
        290                 295

<210> SEQ ID NO 38
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Trp Ser His Pro Gln Phe Glu Lys Thr Gly Ala Ile Pro Val Lys
1               5                   10                  15

Gln Ala Asp Ser Gly Ser Ser Glu Glu Lys Gln Leu Tyr Asn Lys Tyr
            20                  25                  30

Pro Asp Ala Val Ala Thr Trp Leu Asn Pro Asp Pro Ser Gln Lys Gln
        35                  40                  45

Asn Leu Leu Ala Pro Gln Thr Leu Pro Ser Lys Ser Asn Glu Ser His
    50                  55                  60

Asp His Met Asp Asp Met Asp Asp Glu Asp Asp Asp His Val Asp
65                  70                  75                  80

Ser Gln Asp Ser Ile Asp Ser Asn Asp Ser Asp Val Asp Asp Thr
                85                  90                  95

Asp Asp Ser His Gln Ser Asp Glu Ser His His Ser Asp Glu Ser Asp
            100                 105                 110

Glu Leu Val Thr Asp Phe Pro Thr Asp Leu Pro Ala Thr Glu Val Phe
        115                 120                 125

Thr Pro Val Val Pro Thr Val Asp Thr Tyr Asp Gly Arg Gly Asp Ser
    130                 135                 140

Val Val Tyr Gly Leu Arg Ser Lys Ser Lys Lys Phe Arg Arg Pro Asp
145                 150                 155                 160

Ile Gln Tyr Pro Asp Ala Thr Asp Glu Asp Ile Thr Ser His Met Glu
                165                 170                 175

Ser Glu Glu Leu Asn Gly Ala Tyr Lys Ala Ile Pro Val Ala Gln Asp
            180                 185                 190

Leu Asn Ala Pro Ser Asp Trp Asp Ser Arg Gly Lys Asp Ser Tyr Glu
        195                 200                 205

Thr Ser Gln Leu Asp Asp Gln Ser Ala Glu Thr His Ser His Lys Gln
    210                 215                 220

Ser Arg Leu Tyr Lys Arg Lys Ala Asn Asp Glu Ser Asn Glu His Ser
225                 230                 235                 240
```

```
Asp Val Ile Asp Ser Gln Glu Leu Ser Lys Val Ser Arg Glu Phe His
            245                 250                 255

Ser His Glu Phe His Ser His Glu Asp Met Leu Val Val Asp Pro Lys
        260                 265                 270

Ser Lys Glu Glu Asp Lys His Leu Lys Phe Arg Ile Ser His Glu Leu
    275                 280                 285

Asp Ser Ala Ser Ser Glu Val Asn
    290                 295

<210> SEQ ID NO 39
<211> LENGTH: 891
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(888)

<400> SEQUENCE: 39 cat atg gat tac aaa gat gac gat gat aaa ggt att cca att aaa cac      48
His Met Asp Tyr Lys Asp Asp Asp Asp Lys Gly Ile Pro Ile Lys His
1               5                   10                  15 gca gat agt ggt tca tca gaa gaa aaa caa tta tac aac aaa tac cct      96
Ala Asp Ser Gly Ser Ser Glu Glu Lys Gln Leu Tyr Asn Lys Tyr Pro
            20                  25                  30 ggt gct gtt gct aca tgg tta aaa cca gat cct tca caa aaa caa aca     144
Gly Ala Val Ala Thr Trp Leu Lys Pro Asp Pro Ser Gln Lys Gln Thr
        35                  40                  45 ttt tta gct tta caa aat gct gtt tta aca gaa gaa act gac gac ttc     192
Phe Leu Ala Leu Gln Asn Ala Val Leu Thr Glu Glu Thr Asp Asp Phe
    50                  55                  60 aaa caa aaa aca ttt tct tca aaa tct aac gaa agt cat gac gac gtt     240
Lys Gln Lys Thr Phe Ser Ser Lys Ser Asn Glu Ser His Asp Asp Val
65                  70                  75                  80 gat gaa gat gat ggt gat gac gtt gat agt caa gat tca gtt gat tca     288
Asp Glu Asp Asp Gly Asp Asp Val Asp Ser Gln Asp Ser Val Asp Ser
                85                  90                  95 aac gac tta gac gat gat tca aat gaa tca gat gaa agt gat gaa tta     336
Asn Asp Leu Asp Asp Asp Ser Asn Glu Ser Asp Glu Ser Asp Glu Leu
            100                 105                 110 gta aca gat ttc cca act gat att cct gca act caa tta ttc aca cca     384
Val Thr Asp Phe Pro Thr Asp Ile Pro Ala Thr Gln Leu Phe Thr Pro
        115                 120                 125 gct gtt cca aca cgt ggt agt tac gac ggt cgt ggt gat tct gta gct     432
Ala Val Pro Thr Arg Gly Ser Tyr Asp Gly Arg Gly Asp Ser Val Ala
    130                 135                 140 tat ggt tta cgt tca aaa tca aaa aaa tca cac aaa tat gaa gtt caa     480
Tyr Gly Leu Arg Ser Lys Ser Lys Lys Ser His Lys Tyr Glu Val Gln
145                 150                 155                 160 tac cca gac tca act gaa gaa gat ttt aca tca tta gta aaa tct gca     528
Tyr Pro Asp Ser Thr Glu Glu Asp Phe Thr Ser Leu Val Lys Ser Ala
                165                 170                 175 tca atg gaa gac gac ttt aat gca gta tta tta agt cgt act gtt cgt     576
Ser Met Glu Asp Asp Phe Asn Ala Val Leu Leu Ser Arg Thr Val Arg
            180                 185                 190 ggt act tca gat cgt gat tca cac gct aaa gac tct caa gaa act tca     624
Gly Thr Ser Asp Arg Asp Ser His Ala Lys Asp Ser Gln Glu Thr Ser
        195                 200                 205 caa tta gat gat cat tct atg gaa act aaa ggt cgt aaa cac tca caa     672
```

```
Gln Leu Asp Asp His Ser Met Glu Thr Lys Gly Arg Lys His Ser Gln
    210                 215                 220 gaa tac aaa tta cgt gct agt gac gaa tca aat atg cac agt cac gaa       720
Glu Tyr Lys Leu Arg Ala Ser Asp Glu Ser Asn Met His Ser His Glu
225                 230                 235                 240 att ggt tca caa gaa aat tct gaa gta tct agt gaa tta gtt agt caa       768
Ile Gly Ser Gln Glu Asn Ser Glu Val Ser Ser Glu Leu Val Ser Gln
                245                 250                 255 tta agt caa tca cac gaa aaa gaa tta att gtt gac tct aaa agt gaa       816
Leu Ser Gln Ser His Glu Lys Glu Leu Ile Val Asp Ser Lys Ser Glu
            260                 265                 270 gaa gaa gat aaa cac tta aaa ttt cat gtt tct cac gaa tta gat agt       864
Glu Glu Asp Lys His Leu Lys Phe His Val Ser His Glu Leu Asp Ser
        275                 280                 285 gct tca agt gaa att aat taatctaga                                     891
Ala Ser Ser Glu Ile Asn
    290

<210> SEQ ID NO 40
<211> LENGTH: 294
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

His Met Asp Tyr Lys Asp Asp Asp Lys Gly Ile Pro Ile Lys His
1               5                   10                  15

Ala Asp Ser Gly Ser Ser Glu Glu Lys Gln Leu Tyr Asn Lys Tyr Pro
            20                  25                  30

Gly Ala Val Ala Thr Trp Leu Lys Pro Asp Pro Ser Gln Lys Gln Thr
        35                  40                  45

Phe Leu Ala Leu Gln Asn Ala Val Leu Thr Glu Glu Thr Asp Asp Phe
    50                  55                  60

Lys Gln Lys Thr Phe Ser Ser Lys Ser Asn Glu Ser His Asp Asp Val
65                  70                  75                  80

Asp Glu Asp Asp Gly Asp Val Asp Ser Gln Asp Ser Val Asp Ser
            85                  90                  95

Asn Asp Leu Asp Asp Ser Asn Glu Ser Asp Glu Ser Asp Glu Leu
        100                 105                 110

Val Thr Asp Phe Pro Thr Asp Ile Pro Ala Thr Gln Leu Phe Thr Pro
    115                 120                 125

Ala Val Pro Thr Arg Gly Ser Tyr Asp Gly Arg Gly Asp Ser Val Ala
    130                 135                 140

Tyr Gly Leu Arg Ser Lys Ser Lys Lys Ser His Lys Tyr Glu Val Gln
145                 150                 155                 160

Tyr Pro Asp Ser Thr Glu Glu Asp Phe Thr Ser Leu Val Lys Ser Ala
            165                 170                 175

Ser Met Glu Asp Asp Phe Asn Ala Val Leu Leu Ser Arg Thr Val Arg
        180                 185                 190

Gly Thr Ser Asp Arg Asp Ser His Ala Lys Asp Ser Gln Glu Thr Ser
    195                 200                 205

Gln Leu Asp Asp His Ser Met Glu Thr Lys Gly Arg Lys His Ser Gln
    210                 215                 220

Glu Tyr Lys Leu Arg Ala Ser Asp Glu Ser Asn Met His Ser His Glu
225                 230                 235                 240
```

```
Ile Gly Ser Gln Glu Asn Ser Glu Val Ser Glu Leu Val Ser Gln
            245                 250                 255

Leu Ser Gln Ser His Glu Lys Glu Leu Ile Val Asp Ser Lys Ser Glu
        260                 265                 270

Glu Glu Asp Lys His Leu Lys Phe His Val Ser His Glu Leu Asp Ser
        275                 280                 285

Ala Ser Ser Glu Ile Asn
        290

<210> SEQ ID NO 41
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Asp Tyr Lys Asp Asp Asp Lys Gly Ile Pro Ile Lys His Ala
1               5                  10                  15

Asp Ser Gly Ser Ser Glu Glu Lys Gln Leu Tyr Asn Lys Tyr Pro Gly
            20                  25                  30

Ala Val Ala Thr Trp Leu Lys Pro Asp Pro Ser Gln Lys Gln Thr Phe
        35                  40                  45

Leu Ala Leu Gln Asn Ala Val Leu Thr Glu Thr Asp Asp Phe Lys
    50                  55                  60

Gln Lys Thr Phe Ser Ser Lys Ser Asn Glu Ser His Asp Asp Val Asp
65                  70                  75                  80

Glu Asp Asp Gly Asp Asp Val Asp Ser Gln Asp Ser Val Asp Ser Asn
                85                  90                  95

Asp Leu Asp Asp Ser Asn Glu Ser Asp Glu Ser Asp Glu Leu Val
            100                 105                 110

Thr Asp Phe Pro Thr Asp Ile Pro Ala Thr Gln Leu Phe Thr Pro Ala
        115                 120                 125

Val Pro Thr Arg Gly Ser Tyr Asp Gly Arg Gly Asp Ser Val Ala Tyr
    130                 135                 140

Gly Leu Arg Ser Lys Ser Lys Lys Ser His Lys Tyr Glu Val Gln Tyr
145                 150                 155                 160

Pro Asp Ser Thr Glu Glu Asp Phe Thr Ser Leu Val Lys Ser Ala Ser
                165                 170                 175

Met Glu Asp Asp Phe Asn Ala Val Leu Leu Ser Arg Thr Val Arg Gly
            180                 185                 190

Thr Ser Asp Arg Asp Ser His Ala Lys Asp Ser Gln Glu Thr Ser Gln
        195                 200                 205

Leu Asp Asp His Ser Met Glu Thr Lys Gly Arg Lys His Ser Gln Glu
    210                 215                 220

Tyr Lys Leu Arg Ala Ser Asp Glu Ser Asn Met His Ser His Glu Ile
225                 230                 235                 240

Gly Ser Gln Glu Asn Ser Glu Val Ser Glu Leu Val Ser Gln Leu
                245                 250                 255

Ser Gln Ser His Glu Lys Glu Leu Ile Val Asp Ser Lys Ser Glu Glu
            260                 265                 270

Glu Asp Lys His Leu Lys Phe His Val Ser His Glu Leu Asp Ser Ala
        275                 280                 285

Ser Ser Glu Ile Asn
        290
```

<210> SEQ ID NO 42
<211> LENGTH: 885
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(882)

<400> SEQUENCE: 42

```
cat atg gac tat aaa gat gac gat gat aaa ggt att cca att aaa caa      48
His Met Asp Tyr Lys Asp Asp Asp Asp Lys Gly Ile Pro Ile Lys Gln
1               5                   10                  15 aca gac agt gga tct agt gaa gaa aaa caa tta tat aac aaa tat cct      96
Thr Asp Ser Gly Ser Ser Glu Glu Lys Gln Leu Tyr Asn Lys Tyr Pro
            20                  25                  30 gtt gct gta gct act tgg cca aaa cca gat cct tct caa aaa caa act     144
Val Ala Val Ala Thr Trp Pro Lys Pro Asp Pro Ser Gln Lys Gln Thr
        35                  40                  45 ttt tta gct tta caa aac gca gtt tta tct gaa gaa aca gat gat ttc     192
Phe Leu Ala Leu Gln Asn Ala Val Leu Ser Glu Glu Thr Asp Asp Phe
    50                  55                  60 aaa caa aaa aca tta gca tca aaa tct aac gaa tca cat gat gta gat     240
Lys Gln Lys Thr Leu Ala Ser Lys Ser Asn Glu Ser His Asp Val Asp
65                  70                  75                  80 gac gaa gac gat gaa gac gac gta gat tct caa gat tct gtt gat tct     288
Asp Glu Asp Asp Glu Asp Asp Val Asp Ser Gln Asp Ser Val Asp Ser
                85                  90                  95 cac gat aca gat gat gat agt aat caa agt gac gaa agt gat gaa ctt     336
His Asp Thr Asp Asp Asp Ser Asn Gln Ser Asp Glu Ser Asp Glu Leu
            100                 105                 110 gta aca gac ttt cca act gac gta cca gct act caa ttc ttt aca cca     384
Val Thr Asp Phe Pro Thr Asp Val Pro Ala Thr Gln Phe Phe Thr Pro
        115                 120                 125 gct gtt cca act cgt gat agt tat gac gga cgt ggt gac tct gtt gca     432
Ala Val Pro Thr Arg Asp Ser Tyr Asp Gly Arg Gly Asp Ser Val Ala
    130                 135                 140 tac ggt ctt cgt tca aaa tca aaa aaa tca cat cgt tac gaa gat caa     480
Tyr Gly Leu Arg Ser Lys Ser Lys Lys Ser His Arg Tyr Glu Asp Gln
145                 150                 155                 160 tat cca gat tca aca gaa gaa gac ttt aca tct tta gta aaa agt caa     528
Tyr Pro Asp Ser Thr Glu Glu Asp Phe Thr Ser Leu Val Lys Ser Gln
                165                 170                 175 tca atg gaa gat gat ttt aat gct gta ctt tta agt cat aca gtt cgt     576
Ser Met Glu Asp Asp Phe Asn Ala Val Leu Leu Ser His Thr Val Arg
            180                 185                 190 cgt tct cct gac cgt gat tca cat gtt aaa gat tca caa gaa act tca     624
Arg Ser Pro Asp Arg Asp Ser His Val Lys Asp Ser Gln Glu Thr Ser
        195                 200                 205 caa gtt gat gac cac tct atg gaa aca aaa agt cgt aaa cac tct aaa     672
Gln Val Asp Asp His Ser Met Glu Thr Lys Ser Arg Lys His Ser Lys
    210                 215                 220 gaa tac aaa tta aaa gct tct gat gaa aat aat aaa cac agt cac gaa     720
Glu Tyr Lys Leu Lys Ala Ser Asp Glu Asn Asn Lys His Ser His Glu
225                 230                 235                 240 att ggt tct caa gaa tct tct gac att tct agt gaa tta gta ggt caa     768
Ile Gly Ser Gln Glu Ser Ser Asp Ile Ser Ser Glu Leu Val Gly Gln
                245                 250                 255
```

```
act gtt caa tct aat gaa aaa gaa ctt gtt caa cac cca gaa agt gaa      816
Thr Val Gln Ser Asn Glu Lys Glu Leu Val Gln His Pro Glu Ser Glu
        260                 265                 270 gaa caa gat aaa cac tta aaa ttt cgt gtt tca cat gaa tta gat tca      864
Glu Gln Asp Lys His Leu Lys Phe Arg Val Ser His Glu Leu Asp Ser
        275                 280                 285 gca tca agt gaa gtt aat taa                                          885
Ala Ser Ser Glu Val Asn
        290
```

<210> SEQ ID NO 43
<211> LENGTH: 294
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 43

```
His Met Asp Tyr Lys Asp Asp Asp Lys Gly Ile Pro Ile Lys Gln
 1               5                  10                  15

Thr Asp Ser Gly Ser Ser Glu Glu Lys Gln Leu Tyr Asn Lys Tyr Pro
                20                  25                  30

Val Ala Val Ala Thr Trp Pro Lys Pro Asp Pro Ser Gln Lys Gln Thr
            35                  40                  45

Phe Leu Ala Leu Gln Asn Ala Val Leu Ser Glu Thr Asp Phe
 50                  55                  60

Lys Gln Lys Thr Leu Ala Ser Lys Ser Asn Glu Ser His Asp Val Asp
 65                  70                  75                  80

Asp Glu Asp Asp Glu Asp Asp Val Asp Ser Gln Asp Ser Val Asp Ser
                85                  90                  95

His Asp Thr Asp Asp Ser Asn Gln Ser Asp Glu Ser Asp Glu Leu
                   100                 105                 110

Val Thr Asp Phe Pro Thr Asp Val Pro Ala Thr Gln Phe Phe Thr Pro
            115                 120                 125

Ala Val Pro Thr Arg Asp Ser Tyr Asp Gly Arg Gly Asp Ser Val Ala
        130                 135                 140

Tyr Gly Leu Arg Ser Lys Ser Lys Lys Ser His Arg Tyr Glu Asp Gln
145                 150                 155                 160

Tyr Pro Asp Ser Thr Glu Glu Asp Phe Thr Ser Leu Val Lys Ser Gln
                    165                 170                 175

Ser Met Glu Asp Asp Phe Asn Ala Val Leu Leu Ser His Thr Val Arg
                180                 185                 190

Arg Ser Pro Asp Arg Asp Ser His Val Lys Asp Ser Gln Glu Thr Ser
            195                 200                 205

Gln Val Asp Asp His Ser Met Glu Thr Lys Ser Arg Lys His Ser Lys
        210                 215                 220

Glu Tyr Lys Leu Lys Ala Ser Asp Glu Asn Asn Lys His Ser His Glu
225                 230                 235                 240

Ile Gly Ser Gln Glu Ser Ser Asp Ile Ser Ser Glu Leu Val Gly Gln
                    245                 250                 255

Thr Val Gln Ser Asn Glu Lys Glu Leu Val Gln His Pro Glu Ser Glu
                260                 265                 270

Glu Gln Asp Lys His Leu Lys Phe Arg Val Ser His Glu Leu Asp Ser
            275                 280                 285

Ala Ser Ser Glu Val Asn
        290
```

<210> SEQ ID NO 44
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Asp Tyr Lys Asp Asp Asp Lys Gly Ile Pro Ile Lys Gln Thr
1               5                   10                  15

Asp Ser Gly Ser Ser Glu Glu Lys Gln Leu Tyr Asn Lys Tyr Pro Val
            20                  25                  30

Ala Val Ala Thr Trp Pro Lys Pro Asp Pro Ser Gln Lys Gln Thr Phe
        35                  40                  45

Leu Ala Leu Gln Asn Ala Val Leu Ser Glu Glu Thr Asp Asp Phe Lys
    50                  55                  60

Gln Lys Thr Leu Ala Ser Lys Ser Asn Glu Ser His Asp Val Asp Asp
65                  70                  75                  80

Glu Asp Asp Glu Asp Asp Val Asp Ser Gln Asp Ser Val Asp Ser His
                85                  90                  95

Asp Thr Asp Asp Asp Ser Asn Gln Ser Asp Glu Ser Asp Glu Leu Val
            100                 105                 110

Thr Asp Phe Pro Thr Asp Val Pro Ala Thr Gln Phe Phe Thr Pro Ala
        115                 120                 125

Val Pro Thr Arg Asp Ser Tyr Asp Gly Arg Gly Asp Ser Val Ala Tyr
    130                 135                 140

Gly Leu Arg Ser Lys Ser Lys Ser His Arg Tyr Glu Asp Gln Tyr
145                 150                 155                 160

Pro Asp Ser Thr Glu Glu Asp Phe Thr Ser Leu Val Lys Ser Gln Ser
                165                 170                 175

Met Glu Asp Asp Phe Asn Ala Val Leu Leu Ser His Thr Val Arg Arg
            180                 185                 190

Ser Pro Asp Arg Asp Ser His Val Lys Asp Ser Gln Glu Thr Ser Gln
        195                 200                 205

Val Asp Asp His Ser Met Glu Thr Lys Ser Arg Lys His Ser Lys Glu
    210                 215                 220

Tyr Lys Leu Lys Ala Ser Asp Glu Asn Asn Lys His Ser His Glu Ile
225                 230                 235                 240

Gly Ser Gln Glu Ser Ser Asp Ile Ser Ser Glu Leu Val Gly Gln Thr
                245                 250                 255

Val Gln Ser Asn Glu Lys Glu Leu Val Gln His Pro Glu Ser Glu Glu
            260                 265                 270

Gln Asp Lys His Leu Lys Phe Arg Val Ser His Glu Leu Asp Ser Ala
        275                 280                 285

Ser Ser Glu Val Asn
    290

<210> SEQ ID NO 45
<211> LENGTH: 1260
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS

<222> LOCATION: (1)..(1257)

<400> SEQUENCE: 45

| | | | | | | | | | | | | | | | | |
|---|---|---|---|---|---|---|---|---|---|---|---|---|---|---|---|---|
| atg | gat | tac | aaa | gat | gat | gac | gat | aaa | agt | ttt | tca | ggt | gat | ttc | tgt | 48 |
| Met | Asp | Tyr | Lys | Asp | Asp | Asp | Asp | Lys | Ser | Phe | Ser | Gly | Asp | Phe | Cys | |
| 1 | | | | 5 | | | | | 10 | | | | | 15 | | |

| gat | tca | tca | caa | tgt | tta | cat | ggt | ggt | aca | tgt | tta | tta | aat | gaa | gat | 96 |
|---|---|---|---|---|---|---|---|---|---|---|---|---|---|---|---|---|
| Asp | Ser | Ser | Gln | Cys | Leu | His | Gly | Gly | Thr | Cys | Leu | Leu | Asn | Glu | Asp | |
| | | 20 | | | | | 25 | | | | | 30 | | | | |

| cgt | act | cca | cca | ttc | tat | tgt | tta | tgt | cct | gaa | ggt | ttt | aca | ggt | tta | 144 |
|---|---|---|---|---|---|---|---|---|---|---|---|---|---|---|---|---|
| Arg | Thr | Pro | Pro | Phe | Tyr | Cys | Leu | Cys | Pro | Glu | Gly | Phe | Thr | Gly | Leu | |
| | | 35 | | | | | 40 | | | | | 45 | | | | |

| tta | tgt | aat | gaa | aca | gaa | cat | ggt | cca | tgt | ttt | cca | aat | cca | tgt | cac | 192 |
|---|---|---|---|---|---|---|---|---|---|---|---|---|---|---|---|---|
| Leu | Cys | Asn | Glu | Thr | Glu | His | Gly | Pro | Cys | Phe | Pro | Asn | Pro | Cys | His | |
| 50 | | | | | 55 | | | | | 60 | | | | | | |

| aat | gat | gca | gaa | tgt | caa | gtt | act | gat | gat | tca | cat | cgt | ggt | gat | gtt | 240 |
|---|---|---|---|---|---|---|---|---|---|---|---|---|---|---|---|---|
| Asn | Asp | Ala | Glu | Cys | Gln | Val | Thr | Asp | Asp | Ser | His | Arg | Gly | Asp | Val | |
| 65 | | | | 70 | | | | | 75 | | | | | 80 | | |

| ttt | att | caa | tat | att | tgt | aaa | tgt | cca | tta | ggt | tat | gtt | ggt | att | cac | 288 |
|---|---|---|---|---|---|---|---|---|---|---|---|---|---|---|---|---|
| Phe | Ile | Gln | Tyr | Ile | Cys | Lys | Cys | Pro | Leu | Gly | Tyr | Val | Gly | Ile | His | |
| | | | | 85 | | | | | 90 | | | | | 95 | | |

| tgt | gaa | aca | aca | tgt | act | tca | cct | tta | ggt | atg | caa | act | ggt | gct | att | 336 |
|---|---|---|---|---|---|---|---|---|---|---|---|---|---|---|---|---|
| Cys | Glu | Thr | Thr | Cys | Thr | Ser | Pro | Leu | Gly | Met | Gln | Thr | Gly | Ala | Ile | |
| | | | 100 | | | | | 105 | | | | | 110 | | | |

| gca | gat | tca | caa | att | tca | gct | tca | tca | atg | cat | tta | ggt | ttt | atg | ggt | 384 |
|---|---|---|---|---|---|---|---|---|---|---|---|---|---|---|---|---|
| Ala | Asp | Ser | Gln | Ile | Ser | Ala | Ser | Ser | Met | His | Leu | Gly | Phe | Met | Gly | |
| | | 115 | | | | | 120 | | | | | 125 | | | | |

| tta | caa | cgt | tgg | gct | cca | gaa | tta | gca | cgt | tta | cac | caa | aca | ggt | att | 432 |
|---|---|---|---|---|---|---|---|---|---|---|---|---|---|---|---|---|
| Leu | Gln | Arg | Trp | Ala | Pro | Glu | Leu | Ala | Arg | Leu | His | Gln | Thr | Gly | Ile | |
| | 130 | | | | | 135 | | | | | 140 | | | | | |

| gtt | aat | gct | tgg | act | tca | ggt | aat | tat | gat | aaa | aat | cct | tgg | att | caa | 480 |
|---|---|---|---|---|---|---|---|---|---|---|---|---|---|---|---|---|
| Val | Asn | Ala | Trp | Thr | Ser | Gly | Asn | Tyr | Asp | Lys | Asn | Pro | Trp | Ile | Gln | |
| 145 | | | | | 150 | | | | | 155 | | | | | 160 | |

| gtt | aat | tta | atg | cgt | aaa | atg | tgg | gta | aca | ggt | gta | gtt | act | caa | ggt | 528 |
|---|---|---|---|---|---|---|---|---|---|---|---|---|---|---|---|---|
| Val | Asn | Leu | Met | Arg | Lys | Met | Trp | Val | Thr | Gly | Val | Val | Thr | Gln | Gly | |
| | | | 165 | | | | | 170 | | | | | 175 | | | |

| gct | tca | cgt | gca | ggt | tca | gct | gaa | tat | tta | aaa | aca | ttc | aaa | gtt | gca | 576 |
|---|---|---|---|---|---|---|---|---|---|---|---|---|---|---|---|---|
| Ala | Ser | Arg | Ala | Gly | Ser | Ala | Glu | Tyr | Leu | Lys | Thr | Phe | Lys | Val | Ala | |
| | | 180 | | | | | 185 | | | | | 190 | | | | |

| tat | tca | act | gat | ggt | cgt | caa | ttc | caa | ttc | att | caa | gtt | gca | ggt | cgt | 624 |
|---|---|---|---|---|---|---|---|---|---|---|---|---|---|---|---|---|
| Tyr | Ser | Thr | Asp | Gly | Arg | Gln | Phe | Gln | Phe | Ile | Gln | Val | Ala | Gly | Arg | |
| | | 195 | | | | | 200 | | | | | 205 | | | | |

| tca | ggt | gat | aaa | att | ttt | att | ggt | aat | gtt | aat | aat | tca | ggt | tta | aaa | 672 |
|---|---|---|---|---|---|---|---|---|---|---|---|---|---|---|---|---|
| Ser | Gly | Asp | Lys | Ile | Phe | Ile | Gly | Asn | Val | Asn | Asn | Ser | Gly | Leu | Lys | |
| 210 | | | | | 215 | | | | | 220 | | | | | | |

| att | aat | tta | ttc | gat | act | cca | tta | gaa | aca | caa | tat | gtt | cgt | tta | gtt | 720 |
|---|---|---|---|---|---|---|---|---|---|---|---|---|---|---|---|---|
| Ile | Asn | Leu | Phe | Asp | Thr | Pro | Leu | Glu | Thr | Gln | Tyr | Val | Arg | Leu | Val | |
| 225 | | | | 230 | | | | | 235 | | | | | 240 | | |

| cct | att | att | tgt | cat | cgt | ggt | tgt | act | tta | cgt | ttt | gaa | tta | tta | ggt | 768 |
|---|---|---|---|---|---|---|---|---|---|---|---|---|---|---|---|---|
| Pro | Ile | Ile | Cys | His | Arg | Gly | Cys | Thr | Leu | Arg | Phe | Glu | Leu | Leu | Gly | |
| | | | 245 | | | | | 250 | | | | | 255 | | | |

| tgt | gaa | tta | aat | ggt | tgt | aca | gaa | cca | tta | ggt | tta | aaa | gat | aat | aca | 816 |
|---|---|---|---|---|---|---|---|---|---|---|---|---|---|---|---|---|
| Cys | Glu | Leu | Asn | Gly | Cys | Thr | Glu | Pro | Leu | Gly | Leu | Lys | Asp | Asn | Thr | |
| | | | 260 | | | | | 265 | | | | | 270 | | | |

| att | cca | aat | aaa | caa | att | aca | gct | tca | tca | tat | tat | aaa | aca | tgg | ggt | 864 |
|---|---|---|---|---|---|---|---|---|---|---|---|---|---|---|---|---|
| Ile | Pro | Asn | Lys | Gln | Ile | Thr | Ala | Ser | Ser | Tyr | Tyr | Lys | Thr | Trp | Gly | |
| | | 275 | | | | | 280 | | | | | 285 | | | | |

| tta | tca | gct | ttt | tca | tgg | ttt | cct | tat | tat | gct | cgt | tta | gat | aat | caa | 912 |
|---|---|---|---|---|---|---|---|---|---|---|---|---|---|---|---|---|
| Leu | Ser | Ala | Phe | Ser | Trp | Phe | Pro | Tyr | Tyr | Ala | Arg | Leu | Asp | Asn | Gln | |
| | 290 | | | | | 295 | | | | | 300 | | | | | |

```
ggt aaa ttt aat gca tgg aca gct caa aca aat tca gct tca gaa tgg      960
Gly Lys Phe Asn Ala Trp Thr Ala Gln Thr Asn Ser Ala Ser Glu Trp
305                 310                 315                 320 tta caa att gat tta ggt tca caa aaa cgt gta aca ggt att att aca     1008
Leu Gln Ile Asp Leu Gly Ser Gln Lys Arg Val Thr Gly Ile Ile Thr
                325                 330                 335 caa ggt gca cgt gat ttt ggt cac att caa tat gta gct gca tat cgt     1056
Gln Gly Ala Arg Asp Phe Gly His Ile Gln Tyr Val Ala Ala Tyr Arg
            340                 345                 350 gtt gct tat ggt gat gat ggt gtt aca tgg aca gaa tat aaa gat cct     1104
Val Ala Tyr Gly Asp Asp Gly Val Thr Trp Thr Glu Tyr Lys Asp Pro
        355                 360                 365 ggt gct tca gaa tca aaa att ttt cct ggt aat atg gat aat aat tca     1152
Gly Ala Ser Glu Ser Lys Ile Phe Pro Gly Asn Met Asp Asn Asn Ser
    370                 375                 380 cat aaa aaa aat att ttc gaa aca cct ttc caa gct cgt ttt gta cgt     1200
His Lys Lys Asn Ile Phe Glu Thr Pro Phe Gln Ala Arg Phe Val Arg
385                 390                 395                 400 att caa cca gtt gct tgg cat aat cgt att act tta cgt gta gaa tta     1248
Ile Gln Pro Val Ala Trp His Asn Arg Ile Thr Leu Arg Val Glu Leu
                405                 410                 415 tta ggt tgt taa                                                     1260
Leu Gly Cys <210> SEQ ID NO 46
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asp Tyr Lys Asp Asp Asp Lys Ser Phe Ser Gly Asp Phe Cys
1               5                   10                  15

Asp Ser Ser Gln Cys Leu His Gly Gly Thr Cys Leu Leu Asn Glu Asp
                20                  25                  30

Arg Thr Pro Pro Phe Tyr Cys Leu Cys Pro Glu Gly Phe Thr Gly Leu
            35                  40                  45

Leu Cys Asn Glu Thr Glu His Gly Pro Cys Phe Pro Asn Pro Cys His
        50                  55                  60

Asn Asp Ala Glu Cys Gln Val Thr Asp Asp Ser His Arg Gly Asp Val
65                  70                  75                  80

Phe Ile Gln Tyr Ile Cys Lys Cys Pro Leu Gly Tyr Val Gly Ile His
                85                  90                  95

Cys Glu Thr Thr Cys Thr Ser Pro Leu Gly Met Gln Thr Gly Ala Ile
            100                 105                 110

Ala Asp Ser Gln Ile Ser Ala Ser Ser Met His Leu Gly Phe Met Gly
        115                 120                 125

Leu Gln Arg Trp Ala Pro Glu Leu Ala Arg Leu His Gln Thr Gly Ile
    130                 135                 140

Val Asn Ala Trp Thr Ser Gly Asn Tyr Asp Lys Asn Pro Trp Ile Gln
145                 150                 155                 160

Val Asn Leu Met Arg Lys Met Trp Val Thr Gly Val Val Thr Gln Gly
                165                 170                 175

Ala Ser Arg Ala Gly Ser Ala Glu Tyr Leu Lys Thr Phe Lys Val Ala
            180                 185                 190
```

```
Tyr Ser Thr Asp Gly Arg Gln Phe Gln Phe Ile Gln Val Ala Gly Arg
            195                 200                 205

Ser Gly Asp Lys Ile Phe Ile Gly Asn Val Asn Asn Ser Gly Leu Lys
    210                 215                 220

Ile Asn Leu Phe Asp Thr Pro Leu Glu Thr Gln Tyr Val Arg Leu Val
225                 230                 235                 240

Pro Ile Ile Cys His Arg Gly Cys Thr Leu Arg Phe Glu Leu Leu Gly
                245                 250                 255

Cys Glu Leu Asn Gly Cys Thr Glu Pro Leu Gly Leu Lys Asp Asn Thr
            260                 265                 270

Ile Pro Asn Lys Gln Ile Thr Ala Ser Ser Tyr Tyr Lys Thr Trp Gly
        275                 280                 285

Leu Ser Ala Phe Ser Trp Phe Pro Tyr Tyr Ala Arg Leu Asp Asn Gln
    290                 295                 300

Gly Lys Phe Asn Ala Trp Thr Ala Gln Thr Asn Ser Ala Ser Glu Trp
305                 310                 315                 320

Leu Gln Ile Asp Leu Gly Ser Gln Lys Arg Val Thr Gly Ile Ile Thr
                325                 330                 335

Gln Gly Ala Arg Asp Phe Gly His Ile Gln Tyr Val Ala Ala Tyr Arg
            340                 345                 350

Val Ala Tyr Gly Asp Asp Gly Val Thr Trp Thr Glu Tyr Lys Asp Pro
        355                 360                 365

Gly Ala Ser Glu Ser Lys Ile Phe Pro Gly Asn Met Asp Asn Asn Ser
    370                 375                 380

His Lys Lys Asn Ile Phe Glu Thr Pro Phe Gln Ala Arg Phe Val Arg
385                 390                 395                 400

Ile Gln Pro Val Ala Trp His Asn Arg Ile Thr Leu Arg Val Glu Leu
                405                 410                 415

Leu Gly Cys

<210> SEQ ID NO 47
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(408)

<400> SEQUENCE: 47 atg gat tac aaa gat gat gac gat aaa agt caa gca tta tca tat cgt      48
Met Asp Tyr Lys Asp Asp Asp Asp Lys Ser Gln Ala Leu Ser Tyr Arg
1               5                   10                  15 gaa gca gtt tta cgt gct gtt gat caa tta aat gaa caa tca tca gaa      96
Glu Ala Val Leu Arg Ala Val Asp Gln Leu Asn Glu Gln Ser Ser Glu
            20                  25                  30 cct aat att tat cgt tta tta gaa tta gat caa cct cca caa gat gat     144
Pro Asn Ile Tyr Arg Leu Leu Glu Leu Asp Gln Pro Pro Gln Asp Asp
        35                  40                  45 gaa gat cct gat tca cct aaa cgt gta tca ttt cgt gtt aaa gaa aca     192
Glu Asp Pro Asp Ser Pro Lys Arg Val Ser Phe Arg Val Lys Glu Thr
    50                  55                  60 gtt tgt tca cgt aca aca caa caa cca cca gaa caa tgt gat ttc aaa     240
Val Cys Ser Arg Thr Thr Gln Gln Pro Pro Glu Gln Cys Asp Phe Lys
65                  70                  75                  80 gaa aat ggt tta tta aaa cgt tgt gaa ggt aca gta aca tta gat caa     288
```

```
Glu Asn Gly Leu Leu Lys Arg Cys Glu Gly Thr Val Thr Leu Asp Gln
                85                  90                  95 gta cgt ggt aat ttt gat att act tgt aat aat cac caa tca att cgt        336
Val Arg Gly Asn Phe Asp Ile Thr Cys Asn Asn His Gln Ser Ile Arg
            100                 105                 110 att aca aaa caa cca tgg gca cca cca caa gca gct cgt tta tgt cgt        384
Ile Thr Lys Gln Pro Trp Ala Pro Pro Gln Ala Ala Arg Leu Cys Arg
        115                 120                 125 att gtt gtt att cgt gtt tgt cgt taa                                    411
Ile Val Val Ile Arg Val Cys Arg
        130             135

<210> SEQ ID NO 48
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Asp Tyr Lys Asp Asp Asp Lys Ser Gln Ala Leu Ser Tyr Arg
1               5                   10                  15

Glu Ala Val Leu Arg Ala Val Asp Gln Leu Asn Glu Gln Ser Ser Glu
                20                  25                  30

Pro Asn Ile Tyr Arg Leu Leu Glu Leu Asp Gln Pro Gln Asp Asp
            35                  40                  45

Glu Asp Pro Asp Ser Pro Lys Arg Val Ser Phe Arg Val Lys Glu Thr
    50                  55                  60

Val Cys Ser Arg Thr Thr Gln Gln Pro Pro Glu Gln Cys Asp Phe Lys
65                  70                  75                  80

Glu Asn Gly Leu Leu Lys Arg Cys Glu Gly Thr Val Thr Leu Asp Gln
                85                  90                  95

Val Arg Gly Asn Phe Asp Ile Thr Cys Asn Asn His Gln Ser Ile Arg
            100                 105                 110

Ile Thr Lys Gln Pro Trp Ala Pro Pro Gln Ala Ala Arg Leu Cys Arg
        115                 120                 125

Ile Val Val Ile Arg Val Cys Arg
        130             135
```

CHLOROPLAST EXPRESSING COLOSTRUM OR MILK POLYPEPTIDES

CROSS-REFERENCE TO RELATED APPLICATIONS

This application is a continuation under 35 U.S.C. §111 of Intl. Appl. No. PCT/US2015/016460, filed on Feb. 19, 2015, and claims the benefit of and the right to priority to PCT/US2015/016460 under 35 U.S.C. §365. Intl. Appl. No. PCT/US2015/016460 claims the benefit under 35 U.S.C. §119(e) of U.S. Provisional Appl. No. 61/942,024, filed on Feb. 19, 2014, both of which are hereby incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Mar. 26, 2015, is named UCSDP033WO_SL.txt and is 91 kilobytes in size.

FIELD

Provided are colostrum and milk polypeptides recombinantly expressed in photosynthetic organisms, compositions comprising such organisms and methods for producing such organisms.

BACKGROUND

Colostrum or milk bioactive proteins have only been available from the natural source (e.g., human and bovine colostrum or milk); because natural sources are in very limited supply, so too are the associated bioactives contained in them. Tailored combinations of colostrum and milk bioactives have never been available. Bioactive colostrum and milk proteins require both polypeptide accumulation and correct protein folding and post-translational modification.

SUMMARY

The invention provides a solution to drawbacks associated with conventional recombinant protein production methods. For example, the methods feature photosynthetic organisms such as the *Chlamydomonas reinhardtii*, a single-cell green alga, engineered to contain nucleic acids encoding a milk or colostrum protein in the chloroplasts. As a result, the organism produces recombinant biologically active mammalian proteins in the chloroplast. Algae's ability to fold, assemble and accumulate multiple domain proteins as soluble molecules with appropriate post-translational modification of phosphorylation, to preserve biological activity, offers significant advantages. The organisms, isolated cells, and/or sub-cellular organelles such as chloroplasts are useful to produce proteins, which are rare or non-existent in the plant genome/proteome. The proteins produced can be delivered without purification, compared to conventional bioreactor systems, e.g., CHO, bacteria, or yeast, to yield bioactive compounds useful in an edible delivery system.

This edible delivery system comprises food as medicine for not only human therapy but also for veterinary use for companion animals such as dogs and cat as well as livestock such as cows, pigs, chickens, horses and other performance as well as working animals. Purification of bioactive proteins is expedited using the engineered organisms and direct oral administration of organisms themselves leads to efficient delivery, e.g., oral delivery, to gastrointestinal tissues. Oral delivery leads to absorption and assimilation of the encoded proteins into tissues, e.g., bone tissue, of the subject to which the protein or recombinant organism is administered. The system is particularly useful to express/produce proteins, the biological activity of which depends on post-translational modification such as phosphorylation.

Accordingly provided are photosynthetic organisms, e.g., algae and cyanobacteria, as well as cells purified from populations of such organisms and/or sub-cellular organelles, e.g., chloroplasts, purified or obtained from such organism. In varying embodiments, the chloroplasts or cyanobacteria comprise one or more polynucleotides encoding one or more mammalian milk or colostrum polypeptides selected from osteopontin, lactadherin, cathelicidin-1, lysozyme, lactoperoxidase, lingual antimicrobial peptide (LAP), lactalbumin, and soluble CD14. In varying embodiments, the chloroplast is from a photosynthetic organism. In varying embodiments, the chloroplast is from a non-vascular photosynthetic eukaryotic organism. In varying embodiments, the chloroplast is from a photosynthetic unicellular organism. In varying embodiments, the chloroplast is from a microalgae. In some embodiments, the photosynthetic organism is selected from the group consisting of Chlorophyta (green algae), Rhodophyta (red algae), Stramenopiles (heterokonts), Xanthophyceae (yellow-green algae), Glaucocystophyceae (glaucocystophytes), Chlorarachniophyceae (chlorarachniophytes), Euglenida (euglenids), Haptophyceae (coccolithophorids), Chrysophyceae (golden algae), Cryptophyta (cryptomonads), Dinophyceae (dinoflagellates), Haptophyceae coccolithophorids), Bacillariophyta (diatoms), Eustigmatophyceae (eustigmatophytes), Raphidophyceae (raphidophytes), Scenedesmaceae, Phaeophyceae (brown algae). In some embodiments, the photosynthetic organism is selected from the group consisting of *Chlamydomonas reinhardtii, Dunaliella salina, Haematococcus pluvialis, Chlorella vulgaris, Acutodesmus obliquus, Scenedesmus dimorphus, Arthrospira platensis, Arthrospira maxima, Anabaena* sp. PCC7120, *Leptolyngbya* sp, *Synechocystis* sp, and *Synechococcus elongatus* PCC7942. In some embodiments, the chloroplast is a Chlorophyta (green algae) chloroplast. In some embodiments, the green algae is selected from the group consisting of *Chlamydomonas, Dunaliella, Haematococcus, Chlorella*, and Scenedesmaceae. In some embodiments, the *Chlamydomonas* is a *Chlamydomonas reinhardtii*. In varying embodiments, the green algae can be a Chlorophycean, a *Chlamydomonas, C. reinhardtii, C. reinhardtii* 137c, or a psbA deficient *C. reinhardtii* strain. In varying embodiments, the chloroplast is from a higher plant selected from Brassicaceae, Solanaceae, Phaseoleae, Zea and Oryzeae. In some embodiments, the chloroplast comprises at least two (e.g., at least 3, 4, 5, 6, 7, 8, 9 or 10) polynucleotides encoding at least two mammalian milk or colostrum polypeptides. In varying embodiments, the at least two mammalian milk or colostrum polypeptides comprise osteopontin and mammary associated serum amyloid A3 (M-SAA3). In some embodiments, the one or more mammalian polypeptides further comprises one or more mammalian milk or colostrum polypeptides selected from mammary associated serum amyloid A3, osteopontin, soluble cluster of differentiation 14 (sCD14), lactedherin (milk fat globule-EGF factor 8 protein, Mfge8), alpha-lactalbumin, beta-lactoglobin, haptoglobin, immunoglobulins (e.g., IgG1, IgG2, IgA, IgM, IgD), lactoferrin, proline rich polypeptide (PRP), proline rich polypeptide (PRP), growth factors (e.g., transforming growth factor (TGF)-β1, TGF-β2, insulin-like growth factor 1 (somatomedin C) (IGF-1), IGF-2, epidermal growth factor, heparin-binding epidermal growth factor-like growth factor, betacellulin), cytokines (e.g., IL-6, IL-1β, IL 1ra), milk fat globule membrane (MFGM) proteins, serum albumin, glycomacropeptide, casein proteins (e.g., (β-casein, κ-casein, αs1 casein, αs2-casein and γ-casein), enzymes (e.g., superoxide dismutase, lactoperoxidase, alkaline phosphatase, platelet-activating factor-acetylhydroxylase, lysozyme, lipase), mucins, antimicrobial peptides, alpha-defensins, beta-defensins, cathelicidins, 14-3-3 protein zeta chain, 5-oxoprolinase (ATP-hydrolyzing), actin, cytoplasmic 1 (beta-actin), adipose differentiation-related protein, albumin (precursor), aldehyde dehydrogenase (NAD) 2 precursor, ankyrin 3, node of Ranvier (ankyrin G), annexin 1, annexin A2, apolipoprotein A-I, apolipoprotein B, ARP3 (actin-related protein 3, yeast) homolog, ATP synthase, H+ transporting, mitochondrial, F1 complex, alpha subunit, beta-2-microglobulin precursor (lactollin); butyrophilin, subfamily 1, member A1; capping protein (actin filament); muscle Z-line, alpha 1; casein kinase 1, alpha 1; coronin, actin binding protein, 1A; CD36 antigen [collagen type I receptor, thrombospondin receptor]; Chitinase-like protein 1 (CLP-1); DEAD (Asp-Glu-Ala-Asp) box (SEQ ID NO: 25) polypeptide 54; deleted in malignant brain tumors 1; diacylglycerol kinase kappa; endoplasmin precursor (GRP94/GP96); enolase 1; eukaryotic translation initiation factor 4, gamma 2; fatty acid binding protein, heart-type (MDGI); fetuin; fibrinogen alpha chain; fibrinogen beta chain precursor; fibrinogen gamma-B chain precursor; gene model 440, (NCBI); glucose regulated protein 58 kD; glutamate receptor, ionotropic, delta 1; glutathione S-transferase, mu 1; glyceraldehyde-3-phosphate; dehydrogenase (GAPDH); glycerol-3-phosphate dehydrogenase 2; glycoprotein antigen MGP57/53 (Lactadherin/bP47 protein); glycosylation-dependent cell adhesion molecule 1 (lactophorin/PP3); guanine nucleotide binding protein, beta 2; H3 histone, family 3A; heat shock 70 kDa protein 8; heat shock 70 kD protein 5 (glucose-regulated protein); heat shock protein 27; heat shock protein 70 kDa protein 1A; histone 2, H2ab; zinc finger protein 668; hypothetical/unnamed protein LOC51063; IRTA2; isocitrate dehydrogenase 1 (NADP+), soluble; keratin 9; keratin complex 2, basic, gene 6a; keratin, type I cytoskeletal 10; and KIAA1586 protein. In varying embodiments, the one or more mammalian polypeptides are bioactive. In some embodiments, the one or more polynucleotides encoding the one or more mammalian polypeptides is integrated into the chloroplast genome. In some embodiments, the one or more mammalian polypeptides are human milk or colostrum polypeptides. In some embodiments, the one or more mammalian polypeptides are milk or colostrum polypeptides from a mammal selected from the group consisting of human, canine, feline, bovine, porcine, ovine and caprine. In some embodiments, the nucleic acid encoding osteopontin comprises a polynucleotide having at least about 60% sequence identity, e.g., at least about 65%, 70%, 75%, 80%, 85%, 90%, 95%, 98% or 99% sequence identity, to SEQ ID NO:7. In some embodiments, the nucleic acid encoding lactadherin comprises a polynucleotide having at least about 60% sequence identity, e.g., at least about 65%, 70%, 75%, 80%, 85%, 90%, 95%, 98% or 99% sequence identity, to SEQ ID NO:9. In some embodiments, the nucleic acid encoding cathelicidin-1 comprises a polynucleotide having at least about 60% sequence identity, e.g., at least about 65%, 70%, 75%, 80%, 85%, 90%, 95%, 98% or 99% sequence identity, to SEQ ID NO:11. In some embodiments, the one or more mammalian polypeptides are phosphorylated. In varying embodiments, the one or more mammalian polypeptides are bioactive and phosphorylated at 50% or more, e.g., 60%, 70%, 80%, 90% or more, of the amino acid positions that are phosphorylated in the mammalian peptide expressed from a mammalian cell. In some embodiments, the one or more mammalian polypeptides comprises bovine osteopontin and the bovine osteopontin is phosphorylated at one or more amino acids comprising S45, S47, S218, S230, S241, S252 and S259, wherein the amino acid positions are with reference to SEQ ID NO:8 and FIG. 14. In some embodiments, the bovine osteopontin is further phosphorylated at one or more amino acids comprising S48, T51, S85, S88, T93, T94, S100, S103, S106, S109 and S260, wherein the amino acid positions are with reference to SEQ ID NO:8 and FIG. 14. In varying embodiments, the one or more mammalian polypeptides comprises human osteopontin and the human osteopontin is phosphorylated at one or more amino acids comprising Ser20, Ser22, Ser23, Ser58, Ser60, Ser63, Ser81, Ser84, Ser90, Ser99, Ser102, Ser105, Ser108, Ser111, Thr167, Ser173, Ser177, Ser197, Ser201, Ser206, Ser210, Ser216, Ser236, Ser245, Ser249, Ser252, Ser257, Ser273, Ser285, Ser290, and Ser292, wherein the amino acid positions are with reference to FIGS. 3 and 4. In some embodiments, the one or more mammalian polypeptides comprises canine osteopontin and the canine osteopontin is phosphorylated at one or more amino acids comprising Thr57, Thr60, Ser153, Ser163, Thr164, Ser174, Ser176, Ser198, Ser207, Ser230, Ser233, Ser237, Ser246, Ser282, Ser289, and Ser290, wherein the amino acid positions are with reference to FIGS. 5 and 6. In some embodiments, the one or more mammalian polypeptides comprises feline osteopontin and the feline osteopontin is phosphorylated at one or more amino acids comprising Ser174, Ser176, Ser237, and Ser282, wherein the amino acid positions are with reference to FIGS. 7 and 8. In some embodiments, the one or more polynucleotides are operably linked to a promoter that promotes expression in the chloroplast. In varying embodiments, two or more polynucleotides encoding two or more mammalian milk/colostrum polypeptides are integrated into the chloroplast genome. In varying embodiments, the one or more mammalian polypeptides are retained or sequestered in the chloroplast. In some embodiments, the chloroplast is intact. In some embodiments, the chloroplast is freeze-dried. In varying embodiments, the one or more colostrum/milk polypeptides are not purified or isolated from the chloroplast.

In a further aspect, provided are cells from a photosynthetic organism, the cells comprising one or more polynucleotides encoding one or more mammalian milk or colostrum polypeptides selected from osteopontin, lactadherin, soluble CD14, alpha-lactalbumin, lactoperoxidase, lysozyme, lingual antimicrobial peptide and cathelicidin-1. In varying embodiments, the cell is from a non-vascular photosynthetic eukaryotic organism. In varying embodiments, the cell is from a photosynthetic unicellular organism. In varying embodiments, the cell is from a microalgae. In varying embodiments, the cell is from a cyanobacteria. In some embodiments, the photosynthetic organism is selected from the group consisting of Chlorophyta (green algae), Rhodophyta (red algae), Stramenopiles (heterokonts), Xanthophyceae (yellow-green algae), Glaucocystophyceae (glaucocystophytes), Chlorarachniophyceae (chlorarachniophytes), Euglenida (euglenids), Haptophyceae (coccolithophorids), Chrysophyceae (golden algae), Cryptophyta (cryptomonads), Dinophyceae (dinoflagellates), Haptophyceae (coccolithophorids), Bacillariophyta (diatoms), Eustigmatophyceae (eustigmatophytes), Raphidophyceae (raphidophytes), Scenedesmaceae and Phaeophyceae (brown algae). In some embodiments, the photosynthetic organism is selected from the group consisting of *Chlamydomonas reinhardtii, Dunaliella salina, Haematococcus pluvialis, Chlorella vulgaris, Acutodesmus obliquus,* and *Scenedesmus dimorphus* and *Arthrospira platensis, Arthrospira maxima Anabaena* sp. PCC7120, *Leptolyngbya* sp, *Synechocystis* sp, and *Synechococcus elongatus* PCC7942. In some embodiments, the cell is a Chlorophyta (green algae) cell. In some embodiments, the green algae is selected from the group consisting of *Chlamydomonas, Dunaliella, Haematococcus, Chlorella,* and Scenedesmaceae. In some embodiments, the *Chlamydomonas* is a *Chlamydomonas Reinhardtii*. In varying embodiments, the green algae can be a Chlorophycean, a *Chlamydomonas, C. reinhardtii, C. reinhardtii* 137c, *C. reinhardtii* cc1690 or a psbA deficient *C. reinhardtii* strain. In varying embodiments, the cell is from a higher plant selected from Brassicaceae, Solanaceae, Phaseoleae, Zea and Oryzeae. In some embodiments, the cell comprises at least two (e.g., at least 3, 4, 5, 6, 7, 8, 9 or 10) polynucleotides encoding at least two mammalian milk or colostrum polypeptides. In some embodiments, the at least two mammalian milk or colostrum polypeptides comprise osteopontin and mammary associated serum amyloid A3. In some embodiments, the at least two mammalian milk or colostrum polypeptides comprise lysozyme and mammary associated serum amyloid A3. In some embodiments, the one or more mammalian polypeptides further comprises one or more mammalian milk or colostrum polypeptides selected from immunoglobulins (e.g., IgG1, IgG2, IgA, IgM, IgD), lactoferrin, mammary associated serum amyloid A3, proline rich polypeptide (PRP), growth factors (e.g., transforming growth factor (TGF)-(β1, TGF-β2, insulin-like growth factor 1 (somatomedin C) (IGF-1), IGF-2, epidermal growth factor, heparin-binding epidermal growth factor-like growth factor, betacellulin), cytokines (e.g., IL-6, IL-1β, IL 1ra) serum albumin, glycomacropeptide, casein proteins (e.g., (β-casein, κ-casein, αs1 casein, αs2-casein and γ-casein), enzymes (e.g., superoxide dismutase, lactoperoxidase, alkaline phosphatase, platelet-activating factor-acetylhydroxylase, lysozyme), 14-3-3 protein zeta chain, 5-oxoprolinase (ATP-hydrolyzing), actin, cytoplasmic 1 (beta-actin), adipose differentiation-related protein, albumin (precursor), aldehyde dehydrogenase (NAD) 2 precursor, ankyrin 3, node of Ranvier (ankyrin G), annexin 1, annexin A2, apolipoprotein A-I, apolipoprotein B, ARP3 (actin-related protein 3, yeast) homolog, ATP synthase, H+ transporting, mitochondrial, F1 complex, alpha subunit, beta-2-microglobulin precursor (lactollin); butyrophilin, subfamily 1, member A1; capping protein (actin filament); muscle Z-line, alpha 1; casein kinase 1, alpha 1; coronin, actin binding protein, 1A; CD36 antigen [collagen type I receptor, thrombospondin receptor]; Chitinase-like protein 1 (CLP-1); DEAD (Asp-Glu-Ala-Asp) box (SEQ ID NO: 25) polypeptide 54; deleted in malignant brain tumors 1; diacylglycerol kinase kappa; endoplasmin precursor (GRP94/GP96); enolase 1; eukaryotic translation initiation factor 4, gamma 2; fatty acid binding protein, heart-type (MDGI); fetuin; fibrinogen alpha chain; fibrinogen beta chain precursor; fibrinogen gamma-B chain precursor; gene model 440, (NCBI); glucose regulated protein 58 kD; glutamate receptor, ionotropic, delta 1; glutathione S-transferase, mu 1; glyceraldehyde-3-phosphate; dehydrogenase (GAPDH); glycerol-3-phosphate dehydrogenase 2; glycoprotein antigen MGP57/53 (Lactadherin/bP47 protein); glycosylation-dependent cell adhesion molecule 1 (lactophorin/PP3); guanine nucleotide binding protein, beta 2; H3 histone, family 3A; heat shock 70 kDa protein 8; heat shock 70 kD protein 5 (glucose-regulated protein); heat shock protein 27; heat shock protein 70 kDa protein 1A; histone 2, H2ab; zinc finger protein 668; hypothetical/unnamed protein LOC51063; IRTA2; isocitrate dehydrogenase 1 (NADP+), soluble; keratin 9; keratin complex 2, basic, gene 6a; keratin, type I cytoskeletal 10; and KIAA1586 protein. In varying embodiments, the one or more mammalian polypeptides are bioactive. In some embodiments, one or more polynucleotides encoding the one or more mammalian polypeptides is integrated into the chloroplast genome or the nuclear genome of the cell, or a cyanobacterial genome, or into a cyanobacterial plasmid. In some embodiments, the one or more mammalian polypeptides are human milk or colostrum polypeptides. In some embodiments, the one or more mammalian polypeptides are milk or colostrum polypeptides from a mammal selected from the group consisting of human, canine, feline, bovine, porcine, ovine and caprine. In some embodiments, the one or more mammalian polypeptides are milk or colostrum polypeptides. In some embodiments, one or more nucleic acids encoding the one or more mammalian polypeptides selected from osteopontin and lactadherin is integrated into the chloroplast genome of the cell. In some embodiments, the nucleic acid encoding osteopontin comprises a polynucleotide having at least about 60% sequence identity, e.g., at least about 65%, 70%, 75%, 80%, 85%, 90%, 95%, 98% or 99% sequence identity, to SEQ ID NO:7. In some embodiments, the nucleic acid encoding lactadherin comprises a polynucleotide having at least about 60% sequence identity, e.g., at least about 65%, 70%, 75%, 80%, 85%, 90%, 95%, 98% or 99% sequence identity, to SEQ ID NO:9. In some embodiments, the nucleic acid encoding cathelicidin-1 comprises a polynucleotide having at least about 60% sequence identity, e.g., at least about 65%, 70%, 75%, 80%, 85%, 90%, 95%, 98% or 99% sequence identity, to SEQ ID NO:11. In some embodiments, the one or more mammalian polypeptides are phosphorylated. In varying embodiments, the one or more mammalian polypeptides are bioactive and phosphorylated at 50% or more, e.g., 60%, 70%, 80%, 90% or more, of the amino acid positions that are phosphorylated in the mammalian peptide expressed from a mammalian cell. In some embodiments, the one or more mammalian polypeptides comprises bovine osteopontin and the bovine osteopontin is phosphorylated at one or more amino acids comprising S45, S47, S218, S230, S241, S252 and S259, wherein the amino acid positions are with reference to SEQ ID NO:8 and FIG. 14. In some embodiments, the bovine osteopontin is further phosphorylated at one or more amino acids comprising S48, T51, S85, S88, T93, T94, S100, S103, S106, S109 and S260, wherein the amino acid positions are with reference to SEQ ID NO:8 and FIG. 14. In varying embodiments, the one or more mammalian polypeptides comprises human osteopontin and the human osteopontin is phosphorylated at one or more amino acids comprising Ser20, Ser22, Ser23, Ser58, Ser60, Ser63, Ser81, Ser84, Ser90, Ser99, Ser102, Ser105, Ser108, Ser111, Thr167, Ser173, Ser177, Ser197, Ser201, Ser206, Ser210, Ser216, Ser236, Ser245, Ser249, Ser252, Ser257, Ser285, Ser290, and Ser292, wherein the amino acid positions are with reference to FIGS. 3 and 4. In some embodiments, the one or more mammalian polypeptides comprises canine osteopontin and the canine osteopontin is phosphorylated at one or more amino acids comprising Thr57, Thr60, Ser153, Ser163, Thr164, Ser174, Ser176, Ser198, Ser207, Ser230, Ser233, Ser237, Ser246, Ser282, Ser289, and Ser290, wherein the amino acid positions are with reference to FIGS. 5 and 6. In some embodiments, the one or more mammalian polypeptides comprises feline osteopontin and the feline osteopontin is phosphorylated at one or more amino acids comprising Ser174, Ser176, Ser237, and Ser282, wherein the amino acid positions are with reference to FIGS. 7 and 8. In some embodiments, the one or more mammalian polypeptides do not disrupt photosynthetic activity of said organism. In varying embodiments, the one or more polynucleotides are operably linked to a promoter that promotes expression in the chloroplast. In varying embodiments, two or more polynucleotides encoding two or more mammalian milk/colostrum polypeptides are integrated into the chloroplast genome of the cell. In varying embodiments, the one or more mammalian polypeptides are retained or sequestered in the chloroplast of the cell.

In another aspect, provided is a photosynthetic organism comprising one or more polynucleotides encoding one or more mammalian colostrum or milk proteins is selected from the group consisting of osteopontin, lactoperoxidase, lysozyme, lactadherin, soluble CD14, alpha-lactalbumin, lingual antimicrobial peptide and cathelicidin-1. In varying embodiments, the photosynthetic organism is a non-vascular photosynthetic eukaryotic organism. In varying embodiments, the photosynthetic organism is a photosynthetic unicellular organism. In varying embodiments, the photosynthetic organism is a cyanobacteria. In some embodiments, the photosynthetic organism is selected from the group consisting of Chlorophyta (green algae), Rhodophyta (red algae), Stramenopiles (heterokonts), Xanthophyceae (yellow-green algae), Glaucocystophyceae (glaucocystophytes), Chlorarachniophyceae (chlorarachniophytes), Euglenida (euglenids), Haptophyceae (coccolithophorids), Chrysophyceae (golden algae), Cryptophyta (cryptomonads), Dinophyceae (dinoflagellates), Haptophyceae (coccolithophorids), Bacillariophyta (diatoms), Eustigmatophyceae (eustigmatophytes), Raphidophyceae (raphidophytes), Scenedesmaceae and Phaeophyceae (brown algae). In some embodiments, the photosynthetic organism is selected from the group consisting of Chlamydomonas reinhardtii, Dunaliella salina, Haematococcus pluvialis, Chlorella vulgaris, Acutodesmus obliquus, and Scenedesmus dimorphus. In some embodiments, the organism is a Chlorophyta (green algae). In some embodiments, the green algae is selected from the group consisting of Chlamydomonas, Dunaliella, Haematococcus, Chlorella, and Scenedesmaceae. In some embodiments, the Chlamydomonas is a Chlamydomonas reinhardtii. In varying embodiments, the green algae can be a Chlorophycean, a Chlamydomonas, C. reinhardtii, C. reinhardtii 137c, or a psbA deficient C. reinhardtii strain. In varying embodiments, the photosynthetic organism is a higher plant selected from Brassicaceae, Solanaceae, Phaseoleae, Zea and Oryzeae. In some embodiments, the cell comprises at least two (e.g., at least 3, 4, 5, 6, 7, 8, 9 or 10) polynucleotides encoding at least two mammalian milk or colostrum polypeptides. In some embodiments, at least two mammalian milk or colostrum polypeptides comprise osteopontin and mammary associated serum amyloid A3. In some embodiments, at least two mammalian milk or colostrum polypeptides comprise lysozyme and mammary associated serum amyloid A3. In some embodiments, the one or more mammalian polypeptides further comprises one or more mammalian milk or colostrum polypeptides selected from immunoglobulins (e.g., IgG1, IgG2, IgA, IgM, IgD), lactoferrin, mammary associated serum amyloid A3, proline rich polypeptide (PRP), growth factors (e.g., transforming growth factor (TGF)- β1, TGF-β2, insulin-like growth factor 1 (somatomedin C) (IGF-1), IGF-2, epidermal growth factor, heparin-binding epidermal growth factor-like growth factor, betacellulin), cytokines (e.g., IL-6, IL-1β, IL 1ra) serum albumin, glycomacropeptide, casein proteins (e.g., β-casein, κ-casein, αs1casein, αs2-casein and γ-casein), enzymes (e.g., superoxide dismutase, lactoperoxidase, alkaline phosphatase, platelet-activating factor-acetylhydroxylase, lysozyme), 14-3-3 protein zeta chain, 5-oxoprolinase (ATP-hydrolyzing), actin, cytoplasmic 1 (beta-actin), adipose differentiation-related protein, albumin (precursor), aldehyde dehydrogenase (NAD) 2 precursor, ankyrin 3, node of Ranvier (ankyrin G), annexin 1, annexin A2, apolipoprotein A-I, apolipoprotein B, ARP3 (actin-elated protein 3, yeast) homolog, ATP synthase, H+ transporting, mitochondrial, F1 complex, alpha subunit, beta-2-microglobulin precursor (lactollin); butyrophilin, subfamily 1, member A1; capping protein (actin filament); muscle Z-line, alpha 1; casein kinase 1, alpha 1; coronin, actin binding protein, 1A; CD36 antigen [collagen type I receptor, thrombospondin receptor]; Chitinase-like protein 1 (CLP-1); DEAD (Asp-Glu-Ala-Asp) box (SEQ ID NO: 25) polypeptide 54; deleted in malignant brain tumors 1; diacylglycerol kinase kappa; endoplasmin precursor (GRP94/GP96); enolase 1; eukarotic translation initiation factor 4, gamma 2; fatty acid binding protein, heart-type (MDGI); fetuin; fibrinogen alpha chain; fibrinogen beta chain precursor; fibrinogen gamma-B chain precursor; gene model 440, (NCBI); glucose regulated protein 58 kD; glutamate receptor, ionotropic, delta 1; glutathione S-transferase, mu 1; glyceraldehyde-3-phosphate; dehydrogenase (GAPDH); glycerol-3-phosphate dehydrogenase 2; glycoprotein antigen MGP57/53 (Lactadherin/bP47 protein); glycosylation-dependent cell adhesion molecule 1 (lactophorin/PP3); guanine nucleotide binding protein, beta 2; H3 histone, family 3A; heat shock 70 kDa protein 8; heat shock 70 kD protein 5 (glucose-regulated protein); heat shock protein 27; heat shock protein 70 kDa protein 1A; histone 2, H2ab; zinc finger protein 668; hypothetical/unnamed protein LOC51063; IRTA2; isocitrate dehydrogenase 1 (NADP+), soluble; keratin 9; keratin complex 2, basic, gene 6a; keratin, type I cytoskeletal 10; and KIAA1586 protein. In varying embodiments, the one or more mammalian polypeptides are bioactive. In some embodiments, one or more polynucleotides encoding the one or more mammalian polypeptides is integrated into the chloroplast genome of the organism. In some embodiments, the one or more polynucleotides encoding the one or more mammalian polypeptides is operably linked to a promoter that promotes expression in the chloroplast. In some embodiments, the one or more mammalian polypeptides are retained or sequestered in the chloroplast of the organism. In varying embodiments, the one or more mammalian polypeptides comprise a plastid retention sequence comprising a polynucleotide sequence having at least about 60% sequence identity, e.g., at least about 65%, 70%, 75%, 80%, 85%, 90%, 95%, 98% or 99% sequence identity, to SEQ ID NO:23. In varying embodiments, the one or more mammalian polypeptides comprise a plastid retention sequence comprising a polypeptide sequence having at least about 60% sequence identity, e.g., at least about 65%, 70%, 75%, 80%, 85%, 90%, 95%, 98% or 99% sequence identity, to SEQ ID NO:24. In some embodiments, one or more polynucleotides encoding the one or more mammalian polypeptides is integrated into the nuclear genome of the organism. In some embodiments, the one or more mammalian polypeptides are human milk or colostrum polypeptides. In some embodiments, the one or more mammalian polypeptides are milk or colostrum polypeptides from a mammal selected from the group consisting of human, canine, feline, bovine, porcine, ovine and caprine. In some embodiments, one or more nucleic acids encoding the one or more mammalian polypeptides selected from osteopontin and lactadherin is integrated into the chloroplast genome of the cell. In some embodiments, the nucleic acid encoding osteopontin comprises a polynucleotide having at least about 60% sequence identity, e.g., at least about 65%, 70%, 75%, 80%, 85%, 90%, 95%, 98% or 99% sequence identity, to SEQ ID NO:7. In some embodiments, the nucleic acid encoding lactadherin comprises a polynucleotide having at least about 60% sequence identity, e.g., at least about 65%, 70%, 75%, 80%, 85%, 90%, 95%, 98% or 99% sequence identity, to SEQ ID NO:9. In some embodiments, the nucleic acid encoding cathelicidin-1comprises a polynucleotide having at least about 60% sequence identity, e.g., at least about 65%, 70%, 75%, 80%, 85%, 90%, 95%, 98% or 99% sequence identity, to SEQ ID NO:11. In some embodiments, the one or more mammalian polypeptides are phosphorylated. In varying embodiments, the one or more mammalian polypeptides are bioactive and phosphorylated at 50% or more, e.g., 60%, 70%, 80%, 90% or more, of the amino acid positions that are phosphorylated in the mammalian peptide expressed from a mammalian cell. In some embodiments, the one or more mammalian polypeptides comprises bovine osteopontin and the bovine osteopontin is phosphorylated at one or more amino acids comprising S45, S47, S218, S230, S241, S252 and S259, wherein the amino acid positions are with reference to SEQ ID NO:8 and FIG. 14. In some embodiments, the bovine osteopontin is further phosphorylated at one or more amino acids comprising S48, T51, S85, S88, T93, T94, S100, S103, S106, S109 and S260, wherein the amino acid positions are with reference to SEQ ID NO:8and FIG. 14. In varying embodiments, the one or more mammalian polypeptides comprises human osteopontin and the human osteopontin is phosphorylated at one or more amino acids comprising Ser20, Ser22, Ser23, Ser58, Ser60, Ser63, Ser81, Ser84, Ser90, Ser99, Ser102, Ser105, Ser108, Ser111, Thr167, Ser173, Ser177, Ser197, Ser201, Ser206, Ser210, Ser216, Ser236, Ser245, Ser249, Ser252, Ser257, Ser273, Ser285, Ser290, and Ser292, wherein the amino acid positions are with reference to FIGS. 3 and 4. In some embodiments, the one or more mammalian polypeptides comprises canine osteopontin and the canine osteopontin is phosphorylated at one or more amino acids comprising Thr57, Thr60, Ser153, Ser163, Thr164, Ser174, Ser176, Ser198, Ser207, Ser230, Ser233, Ser237, Ser246, Ser282, Ser289, and Ser290, wherein the amino acid positions are with reference to FIGS. 5 and 6. In some embodiments, the one or more mammalian polypeptides comprises feline osteopontin and the feline osteopontin is phosphorylated at one or more amino acids comprising Ser174, Ser176, Ser237, and Ser282, wherein the amino acid positions are with reference to FIGS. 7 and 8. In varying embodiments, the one or more polynucleotides are operably linked to a promoter that promotes expression in the chloroplast. In varying embodiments, two or more polynucleotides encoding two or more mammalian milk/colostrum polypeptides are integrated into the chloroplast genome of the organism. In varying embodiments, the one or more mammalian polypeptides are retained or sequestered in the chloroplast of the cell. In some embodiments, the one or more mammalian polypeptides are phosphorylated. For example, proteins produced in chloroplasts or cyanobacteria are post-translationally modified by phosphorylation with a high level of fidelity compared to the same protein produced in other recombinant production systems. Colostrum/milk polypeptides produced in chloroplasts or cyanobacteria are characterized by at least 50%, 75%, 85%, 90%, 95% 98%, 99% and even up to 100% of the level of bioactivity of the natural colostrum-derived counterpart protein. In some embodiments, the one or more mammalian polypeptides comprise an amino acid sequence that promotes secretion from a cell. In some embodiments, the one or more mammalian polypeptides comprise an amino acid sequence that promotes retention on the plasma membrane of a cell. In some embodiments, the one or more mammalian polypeptides comprise an amino acid sequence that promotes protein accumulation. In some embodiments, the one or more mammalian polypeptides do not disrupt photosynthetic activity of said organism.

Further provided are methods for producing one or more mammalian colostrum or milk proteins, comprising culturing a cell or an organism as described above and herein. In some embodiments, the cell or the organism is grown in the absence of light and in the presence of an organic carbon source.

Further provided are polynucleotides for expression of colostrum/milk polypeptides in a chloroplast. In some embodiments, the polynucleotide encoding osteopontin comprises a polynucleotide having at least about 60% sequence identity, e.g., at least about 65%, 70%, 75%, 80%, 85%, 90%, 95%, 98% or 99% sequence identity, to SEQ ID NO:7. In some embodiments, the polynucleotide encoding lactadherin comprises a polynucleotide having at least about 60% sequence identity, e.g., at least about 65%, 70%, 75%, 80%, 85%, 90%, 95%, 98% or 99% sequence identity, to SEQ ID NO:9. In some embodiments, the polynucleotide encoding cathelicidin-1 comprises a polynucleotide having at least about 60% sequence identity, e.g., at least about 65%, 70%, 75%, 80%, 85%, 90%, 95%, 98% or 99% sequence identity, to SEQ ID NO:11.

Further provided are mammalian osteopontin polypeptides. In varying embodiments, the osteopontin polypeptide is a bovine osteopontin polypeptide phosphorylated at one or more amino acids comprising S45, S47, S218, S230, S241, S252 and S259, wherein the amino acid positions are with reference to SEQ ID NO:8 and FIG. 14. In some embodiments, the osteopontin polypeptide is further phosphorylated at one or more amino acids comprising S48, T51, S85, S88, T93, T94, S100, S103, S106, S109 and S260, wherein the amino acid positions are with reference to SEQ ID NO:8 and FIG. 14. In some embodiments, the bovine osteopontin polypeptide comprises at least about 60% identity, e.g., at least about 65%, 70%, 75%, 80%, 85%, 90%, 95%, 98% or 99% sequence identity, to amino acid sequence of SEQ ID NO:8. In varying embodiments, the osteopontin polypeptide is a human osteopontin polypeptide that is phosphorylated at one or more amino acids comprising Ser20, Ser22, Ser23, Ser58, Ser60, Ser63, Ser81, Ser84, Ser90, Ser99, Ser102, Ser105, Ser108, Ser111, Thr167, Ser173, Ser177, Ser197, Ser201, Ser206, Ser210, Ser216, Ser236, Ser245, Ser249, Ser252, Ser257, Ser273, Ser285, Ser290, and Ser292, wherein the amino acid positions are with reference to FIGS. 3 and 4. In some embodiments, the human osteopontin polypeptide comprises at least about 60% identity, e.g., at least about 65%, 70%, 75%, 80%, 85%, 90%, 95%, 98% or 99% sequence identity, to amino acid sequence of SEQ ID NO:18. In some embodiments, the osteopontin polypeptide is a canine osteopontin polypeptide that is phosphorylated at one or more amino acids comprising Thr57, Thr60, Ser153, Ser163, Thr164, Ser174, Ser176, Ser198, Ser207, Ser230, Ser233, Ser237, Ser246, Ser282, Ser289, and Ser290, wherein the amino acid positions are with reference to FIGS. 5 and 6. In some embodiments, the canine osteopontin polypeptide comprises at least about 60% identity, e.g., at least about 65%, 70%, 75%, 80%, 85%, 90%, 95%, 98% or 99% sequence identity, to amino acid sequence of SEQ ID NO:20. In some embodiments, the osteopontin polypeptide is a feline osteopontin polypeptide that is phosphorylated at one or more amino acids comprising Ser174, Ser176, Ser237, and Ser282, wherein the amino acid positions are with reference to FIGS. 7 and 8. In some embodiments, the feline osteopontin polypeptide comprises at least about 60% identity, e.g., at least about 65%, 70%, 75%, 80%, 85%, 90%, 95%, 98% or 99% sequence identity, to amino acid sequence of SEQ ID NO:22.

Further provided are compositions edible by a mammal comprising one or more populations of cells, one or more populations of organisms and/or an osteopontin polypeptide, as described above and herein. In some embodiments, the composition is selected from a liquid or beverage (e.g., infant formula), a food, a feed, a food supplement, a nutraceutical (e.g., a pill). In some embodiments, the composition is selected from the group consisting of a compressed algal cake, an algal paste and an algal powder. In varying embodiments, the compositions are lyophilized or spray dried. In some embodiments, the photosynthetic organisms (e.g., algae) are lyophilized or spray-dried prior to the addition to an edible composition, e.g., a food, beverage or tablet consumable by a mammal, e.g., a human, a canine, a feline. In some embodiments, the photosynthetic organisms (e.g., algae) are formulated into a wet paste prior to the addition to an edible composition, e.g., a food, beverage or tablet consumable by a mammal, e.g., a human, a canine, a feline. In some embodiments, the photosynthetic organisms (e.g., algae) are formulated into a powder to be sprinkled onto or into an edible composition, e.g., a food, beverage or tablet consumable by a mammal, e.g., a human, a canine, a feline. In some embodiments the photosynthetic organisms (e.g., algae) are blended or mixed into an edible composition, e.g., a food, beverage or tablet consumable by a mammal, e.g., a human, a canine, a feline.

Further provided are methods of producing a such compositions edible by a mammal. In varying embodiments, the methods comprise combining two or more populations of cells or two or more populations of organisms as described above and herein. In some embodiments, the methods comprise combining two or more of: a population of cells, a population of cyanobacteria, a population of photosynthetic organisms, and an osteopontin polypeptide, as described above and herein.

DEFINITIONS

The term "non-vascular photosynthetic eukaryotic organism" refers to an organism of the kingdom Planta that does not have xylem or phloem. These include all species of algae and mosses as well as other photosynthetic organisms like liverworts.

The term "bioactive" refers to detectable biological activity of a polypeptide, using any assay known in the art to detect the biological activity. The biological activities of the polypeptides described herein and assays for detecting their biological activity are known in the art. For example, the bioactivity of osteopontin can be measured by the ability of osteopontin to adhere to human embryonic 293 cells when in the presence of the divalent cations, $Mg^{2+}$ or $Mn^{2+}$ but not $Ca^{2+}$ (Hu, et al, *J Biol Chem*. (1995) 270(17):9917-25). The bioactivity of mammary-associated serum amyloid (M-SAA3) protein can be determined by the purified proteins ability to stimulate muc3 production from HT29 cells (Manuell et al., *Plant Biotechnol J*. (2007) 5(3):402-12). The bioactivity of lactadherin can be determined by its ability to bind to phosphatidylserine (Otzen, et al., *Biochim Biophys Acta*. (2012) 1818(4):1019-27). Cathelicidin-1 activity can be determined using an antimicrobial assay and measuring luminescence. See, e.g., Sue, et al. *Infect Immun*. 2000 68(5) 2748-2755.

The terms "identical" or percent "identity," and variants thereof in the context of two or more polynucleotide or two or more amino acid sequences, refer to two or more sequences or subsequences that are the same. Sequences are "substantially identical" if they have a specified percentage of nucleic acid residues or amino acid residues that are the same (i.e., at least 60% identity, optionally at least 65%, 70%, 75%, 80%, 85%, 90%, 95%, 96%, 97%, 98%, or 99% identity to a reference sequence (e.g., SEQ ID NOs: 1-24) over a specified region (or the whole reference sequence when not specified)), when compared and aligned for maximum correspondence over a comparison window, or designated region as measured using any sequence comparison algorithm known in the art (GAP, BESTFIT, BLAST, Align, FASTA, and TFASTA in the Wisconsin Genetics Software Package, Genetics Computer Group (GCG), 575 Science Dr., Madison, Wisc.), Karlin and Altschul Proc. Natl. Acad. Sci. (U.S.A.) 87:2264-2268 (1990) set to default settings, or by manual alignment and visual inspection (see, e.g., Ausubel et al., Current Protocols in Molecular Biology (1995-2014). Provided are polynucleotides improved for expression in photosynthetic (e.g., algal) host cells that are substantially identical to the polynucleotides of SEQ ID NOs: 1, 3, 5, 7, 9, 11, 17, 19, 21 and 23. Provided are polypeptides expressed in photosynthetic (e.g., algal) host cells that are substantially identical to the polypeptides of SEQ ID NOs: 2, 4, 6, 8, 10, 12, 13, 14, 15, 16, 17, 20, 22 and 24. Optionally, the identity exists over a region that is at least about 50, 100, 150, 200, 250, 300 amino acids in length, or more preferably over a region that is 100, 200, 300, 400, 500, 600, 800, 1000, or more, nucleic acids in length, or over the full-length of the sequence.

The term "conservatively modified variations" refers to individual substitutions, deletions or additions which alter, add or delete a single amino acid or a small percentage of amino acids (typically less than 5%, more typically less than 1%) in an encoded sequence, where the alterations result in the substitution of an amino acid with a chemically similar amino acid; and the alterations, deletions or additions do not alter the structure, function and/or immunogenicity of the sequence. Conservative substitution tables providing functionally similar amino acids are well known in the art. The following six groups each contain amino acids that are conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V); and
  6) Phenylalanine (F), Tyrosine (Y), Tryptophan (W).

BRIEF DESCRIPTION OF THE DRAWINGS

This application contains at least one drawing executed in color. Copies of this patent or patent application publication with color drawing(s) will be provided by the Office upon request and payment of the necessary fee.

FIG. 1 illustrates examples of colostrum/milk proteins and their bioactivities

FIG. 2 illustrates a polynucleotide sequence (SEQ ID NO: 34) with altered codons for improved expression of bovine osteopontin from the chloroplast genome and the corresponding amino acid sequence (SEQ ID NO: 35).

FIG. 3 illustrates a polynucleotide sequence (SEQ ID NO: 36) with altered codons for improved expression of human osteopontin from the chloroplast genome and the corresponding amino acid sequence (SEQ ID NO: 37). Optional N-terminal STREP-TAG® is underlined.

FIG. 4 illustrates the amino acids that are phosphorylated on the human variant of osteopontin expressed from a chloroplast genome (SEQ ID NO: 38). The phosphorylated residues include Ser20, Ser22, Ser23, Ser58, Ser60, Ser63, Ser81, Ser84, Ser90, Ser99, Ser102, Ser105, Ser108, Ser111, Thr167, Ser173, Ser177, Ser197, Ser201, Ser206, Ser210, Ser216, Ser236, Ser245, Ser249, Ser252, Ser257, Ser273, Ser285, Ser290, and Ser292. Amino acid position numbers are with reference to FIGS. 3 and 4. See also, Christensen et al. Biochem J. 2005 Aug. 15; 390(Pt 1): 285-292.

FIG. 5 illustrates a polynucleotide sequence (SEQ ID NO: 39) with altered codons for improved expression of canine osteopontin from the chloroplast genome and the corresponding amino acid sequence (SEQ ID NO: 40). Optional N-terminal FLAG-tag is underlined.

FIG. 6 illustrates the amino acids that are phosphorylated on the canine variant of osteopontin expressed from a chloroplast genome (SEQ ID NO: 41). The phosphorylated residues include Thr57, Thr60, Ser153, Ser163, Thr164, Ser174, Ser176, Ser198, Ser207, Ser230, Ser233, Ser237, Ser246, Ser282, Ser289, and Ser290. Amino acid position numbers are with reference to FIGS. 5 and 6.

FIG. 7 illustrates a polynucleotide sequence (SEQ ID NO: 42) with altered codons for improved expression of feline osteopontin from the chloroplast genome and the corresponding amino acid sequence (SEQ ID NO: 43). Optional N-terminal FLAG-tag is underlined.

FIG. 8 illustrates the amino acids that are phosphorylated on the feline variant of osteopontin expressed from a chloroplast genome (SEQ ID NO: 44). The phosphorylated residues include Ser174, Ser176, Ser237, and Ser282. Amino acid position numbers are with reference to FIGS. 7 and 8.

FIG. 9 illustrates a polynucleotide sequence (SEQ ID NO: 45) with altered codons for improved expression of lactadherin from the chloroplast genome and the corresponding amino acid sequence (SEQ ID NO: 46).

FIG. 10 illustrates a polynucleotide sequence (SEQ ID NO: 47) with altered codons for improved expression of cathelicidin-1 from the chloroplast genome and the corresponding amino acid sequence (SEQ ID NO: 48).

FIG. 14A illustrates a mass spectrometry analysis of purified chloroplast expressed bovine osteopontin (SEQ ID NO: 8). FIG. 14B summarizes mass spec identification of phosphorylation sites of bovine osteopontin expressed from a chloroplast. Localized phosphorylation sites on chloroplast expressed bovine osteopontin include S45, S47, S218, S230, S241, S252 and S259. Ambiguous phosphorylation sites on chloroplast expressed bovine osteopontin include S48, T51, S84, S88, T93, T94, S100, S103, S106, S109 and S260. Amino acid position numbers are with reference to SEQ ID NO:8.

FIG. 21 illustrates Western blots showing the accumulation of M-SAA3 and osteopontin both expressed in the chloroplast genome. The lanes contain the following: Lane 1: Negative Control, Lane 2: A Protein Standard, Lane 3 Soluble protein from a transgenic strain of *C. reinhardtii* expressing only osteopontin from the chloroplast genome, Lane 4: Total from a transgenic strain of *C. reinhardtii* expressing only osteopontin from the chloroplast genome, Lane 5: Soluble protein from a transgenic strain expressing both osteopontin and M-SAA3 from the chloroplast genome, Lane 6: Total protein from a transgenic strain expressing both osteopontin and M-SAA3 from the chloroplast genome, Lane 7: Soluble protein from a transgenic strain of *C. reinhardtii* expressing only M-SAA3 from the chloroplast genome, Lane 8: Total from a transgenic strain of *C. reinhardtii* expressing only M-SAA3 from the chloroplast genome. The top Western is probed with an antibody against the M-SAA3 protein and the bottom Western was probed with an antibody against the flag tag of the osteopontin protein.

DETAILED DESCRIPTION

1. Introduction

Figure 11:
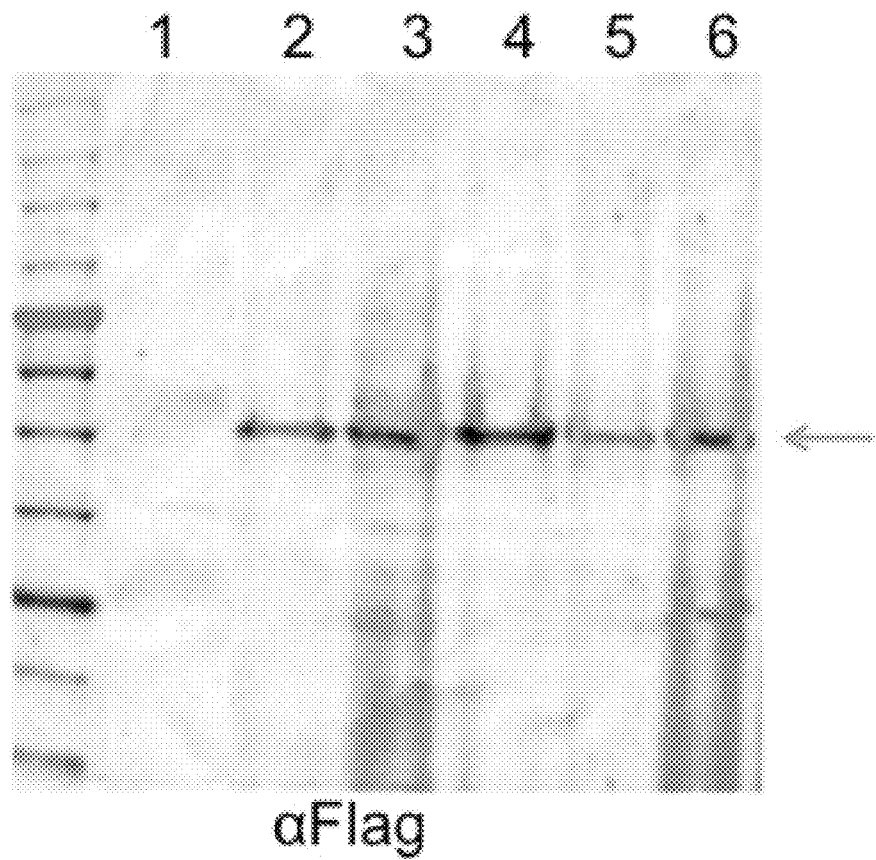
FIG. 11 illustrates a Western blot analysis of transgenic algae strains whose chloroplast genome has been transformed with a flag tagged osteopontin gene. Westerns probed with an anti-flag antibody. Lane 1 Negative control. Lanes 2-6: Independent transgenic strains.

Described herein are compositions and processes to produce bioactive colostrum and/or milk proteins for health and nutrition purposes using chloroplast-engineered photosynthetic organisms (e.g., algae) as both a production and delivery vehicle. The organisms and processes described herein provide an alternative system and organisms for lower cost and large-scale production of singular and/or tailored mixtures/combinations of orally active colostrum and milk bioactives in an orally available form (e.g., edible algae). In varying embodiments, two or more colostrum/milk polypeptides can be expressed from the chloroplasts of the same organism.

Genes encoding bioactive colostrum/milk proteins have altered codons for expression from the chloroplast genomes of edible photosynthetic organisms (e.g., for example, higher plants, algae, microalgae, including Chlorophyta, e.g., *Chlamydomonas reinhardtii*) or from the genome or plasmid of cyanobacteria). Illustrative colostrum/milk proteins include without limitation mammary associated serum amyloid A3, lactoperoxidase, lactoferrin, osteopontin, lysozyme, alpha-lactalbumin, lactadherin, soluble CD14, cathelicidin-1, and lingual antimicrobial peptide (FIG. 1). The colostrum/milk genes can be integrated into and expressed from the chloroplast genomes of photosynthetic organisms. Expression and bioactivity can be confirmed using methods known in the art.

Production and/or delivery of colostrum/milk polypeptides in edible photosynthetic organisms finds use, e.g., in human and mammal health and nutrition; prophylaxis and treatment for enteric infection; prophylaxis and/or treatment of gastric, intestinal, or bowel inflammation; improving nutrient uptake efficiency; improving bone strength; food preservation and processing; cosmetics preservation; odor treatment and neutralization; oral hygiene; acne treatment; and topical and oral antibacterial, antiviral, and/or antimicrobial therapy.

2. Colostrum/Milk Polynucleotides and Polypeptides

Photosynthetic eukaryotic organisms have one or more polynucleotides encoding one or more mammalian colostrum/milk polypeptides are integrated into the chloroplast genome. In varying embodiments, 2, 3, 4, 5, 6, 7, 8, 9, 10, or more, polynucleotides encoding mammalian colostrum/milk polypeptides are independently integrated into the chloroplast genome of a photosynthetic organism.

Illustrative mammalian colostrum/milk polypeptides for expression in photosynthetic organisms (e.g. chlorophyta, e.g., *Chlamydomonas*), and chloroplast and cells thereof, are described above and herein. See, e.g., Smolenski, et al., *J Proteome Res*. 2007 January; 6(1):207-15; Boudry and Thewis, Bulletin UASVM Animal Science and Biotechnologies (2009) 66 (1-2); Chatterton, et al., *Intl Journal of Biochemistry & Cell Biology* 45 (2013) 1730-1747; Lis, et al., *Postepy Hig Med Dosw* (2013) 67: 529-547; and Artym, et al., *Postepy Hig Med Dosw* (2013) 67: 800-816. In varying embodiments, the one or more colostrum/milk polypeptides are whey proteins (e.g., alpha-lactalbumim, beta-lactoglobulin, osteopontin, lactoferrin and/or immunoglobulins). The expressed mammalian colostrum/milk polypeptides, and chloroplasts, cells and photosynthetic organisms comprising the polypeptides, can be used as and in compositions edible by a mammal (e.g., having both nutritional and therapeutic value).

In varying embodiments, the milk/colostrum polypeptides are human, non-human primate, bovine (e.g., cow, bison), ovine, caprine, camelid, human, canine, feline, equine, marsupial, or from any other mammal of interest. The polynucleotide and polypeptide sequences of mammalian homologs of milk/colostrum polypeptides are known in the art. For example, the GenBank Ref. Seq. Accession Nos. for osteopontin polypeptide homologs are NP_000573.1 (human), XP_003434072.1 (canine), XP_003985233.1 (feline), and NP_776612.1 (bovine). For example, mammalian milk/colostrum proteins (e.g., osteopontin, e.g., from a human, canine, or feline) can be produced in a photosynthetic organism (e.g., algae) and subsequently lyophilized and sprinkled onto a food or into a beverage consumable by the mammal (e.g., human, canine, or feline, respectively). In another example, mammalian milk/colostrum proteins (e.g., from a human, canine, feline or equine) produced in a photosynthetic organism (e.g., algae) can be formulated into a wet paste and delivered orally to the mammal (e.g., to the human, canine, feline or equine), e.g., using a syringe. In another example, lyophilized, freeze-dried or spray-dried photosynthetic organisms (e.g., algae) comprising mammalian milk/colostrum polypeptides can be re-suspended in water for oral delivery to the mammal (e.g., to the human, canine, feline or equine), e.g., using a syringe. In another example, lyophilized, freeze-dried, spray-dried or powdered photosynthetic organisms (e.g., algae) comprising mammalian milk/colostrum polypeptides can be sprayed onto or mixed or blended into a food, feed or beverage edible by a mammal (e.g., to the human, canine, feline or equine), e.g., sprayed onto kibble for a non-human mammal.

Polynucleotides encoding one or more milk/colostrum polypeptides, or immunogenic fragments thereof, can be altered for improved expression in a photosynthetic (e.g., algal) host cells. For example, codons in the wild-type polynucleotides encoding one or more milk/colostrum polypeptides rarely used by the photosynthetic (e.g., algal) host cell can be replaced with a codon coding for the same or a similar amino acid residue that is more commonly used by the photosynthetic (e.g., algal) host cell (i.e., employing algal chloroplast codon bias), thereby allowing for more efficient expression of the milk/colostrum polypeptide and higher yields of the expressed milk/colostrum polypeptide in the photosynthetic host, in comparison to expression of the milk/colostrum polypeptide from the wild-type polynucleotide. Methods for altering polynucleotides for improved expression in a photosynthetic (e.g., algal) host cell, particularly in a *Chlamydomonas reinhardtii* host cell, are known in the art and described in, e.g., Franklin et at (2002) *Plant J* 30:733-744; Fletcher, et al., *Adv Exp Med Biol.* (2007) 616:90-8; Heitzer, et al., *Adv Exp Med Biol.* (2007) 616:46-53; Rasala and Mayfield, *Bioeng Bugs.* (2011) 2(1): 50-4; Rasala, et al, *Plant Biotechnol J.* (2010) 8(6):719-33; Wu, et al., *Bioresour Technol.* (2011) 102(3):2610-6; Morton, *J Mol Evol.* (1993) 37(3):273-80; Morton, *J Mol Evol.* (1996) 43(1):28-31; and Morton, *J Mol Evol.* (1998) 46(4): 449-59.

In various embodiments, polynucleotide sequences encoding milk/colostrum polypeptides can be improved for expression in photosynthetic organisms (e.g., algae) by changing codons that are not common in the algae host cell (e.g., used less than ~20% of the time). A codon usage database of use is found at kazusa.or.jp/codon/. For improved expression of polynucleotide sequences encoding milk/colostrum polypeptides in *C. reinhardtii* host cells, codons rare or not common to the chloroplast of *C. reinhardtii* in the native milk/colostrum nucleic acid sequences are reduced or eliminated. A representative codon table summarizing codon usage in the *C. reinhardtii* chloroplast is found on the internet at kazusa.or.jp/codon/cgi-bin/showcodon.cgi?species=3055.chloroplast. In various embodiments, preferred or more common codons for amino acid residues in *C. reinhardtii* are as follows:

| Amino Acid Residue | Preferred codons for improved expression in algae |
|---|---|
| Ala | GCT, GCA |
| Arg | CGT |
| Asn | AAT |
| Asp | GAT |
| Cys | TGT |
| Gln | CAA |
| Glu | GAA |
| Gly | GGT |
| Ile | ATT |
| His | CAT |
| Leu | TTA |
| Lys | AAA |
| Met | ATG |
| Phe | TTT |
| Pro | CCA |
| Ser | TCA |
| Thr | ACA, ACT |
| Trp | TGG |
| Tyr | TAT |
| Val | GTT, GTA |
| STOP | TAA |

In certain instances, less preferred or less common codons for expression in an algal host cell can be included in a polynucleotide sequence encoding a milk/colostrum polypeptide, for example, to avoid sequences of multiple or extended codon repeats, or sequences of reduced stability (e.g., extended A/T-rich sequences), or having a higher probability of secondary structure that could reduce or interfere with expression efficiency. In various embodiments, the polynucleotide sequence can be synthetically prepared. For example, the desired amino acid sequence of a milk/colostrum polypeptide as described herein can be entered into a software program with algorithms for determining codon usage for a photosynthetic (e.g., algal) host cell. Illustrative software includes GeneDesigner available from DNA 2.0, on the internet at dna20.com/genedesigner2.

In varying embodiments, the polypeptides are phosphorylated. Chloroplast-expressed gene products provide a distinct advantage over those encoded in the nuclear genome, particularly in the case in which phosphorylation contributes to the biologic activity of the end product protein. In varying embodiments, mammalian polypeptides expressed from the chloroplasts of photosynthetic organisms are phosphorylated and bioactive. In varying embodiments, the pattern of phosphorylation of the mammalian polypeptide expressed from the chloroplast is different is different from the pattern of phosphorylation of the mammalian polypeptide expressed from a mammalian cell. In varying embodiments, the one or more mammalian polypeptides are bioactive and phosphorylated at 50% or more, e.g., 60%, 70%, 80%, 90% or more, of the amino acid positions that are phosphorylated in the mammalian peptide expressed from a mammalian cell. In some embodiments, the one or more mammalian polypeptides comprises bovine osteopontin and the bovine osteopontin is phosphorylated at one or more amino acids comprising S45, S47, S218, S230, S241, S252 and S259, wherein the amino acid positions are with reference to SEQ ID NO:8 and FIG. 14. In some embodiments, the bovine osteopontin is further phosphorylated at one or more amino acids comprising S48, T51, S85, S88, T93, T94, S100, S103, S106, S109 and 5260, wherein the amino acid positions are with reference to SEQ ID NO:8 and FIG. 14. In varying embodiments, the one or more mammalian polypeptides comprises human osteopontin and the human osteopontin is phosphorylated at one or more amino acids comprising Ser20, Ser22, Ser23, Ser58, Ser60, Ser63, Ser81, Ser84, Ser90, Ser99, Ser102, Ser105, Ser108, Ser111, Thr167, Ser173, Ser177, Ser197, Ser201, Ser206, Ser210, Ser216, Ser236, Ser245, Ser249, Ser252, Ser257, Ser273, Ser285, Ser290, and Ser292, wherein the amino acid positions are with reference to FIGS. 3 and 4. In some embodiments, the one or more mammalian polypeptides comprises canine osteopontin and the canine osteopontin is phosphorylated at one or more amino acids comprising Thr57, Thr60, Ser153, Ser163, Thr164, Ser174, Ser176, Ser198, Ser207, Ser230, Ser233, Ser237, Ser246, Ser282, Ser289, and Ser290, wherein the amino acid positions are with reference to FIGS. 5 and 6. In some embodiments, the one or more mammalian polypeptides comprises feline osteopontin and the feline osteopontin is phosphorylated at one or more amino acids comprising Ser174, Ser176, Ser237, and Ser282, wherein the amino acid positions are with reference to FIGS. 7 and 8.

In varying embodiments, the polynucleotide sequences encoding the mammalian milk/colostrum polypeptides can further encode a sequence that promotes protein accumulation. Protein accumulation amino acid sequences are known in the art and find use.

The psbA promoter and untranslated regions (UTRs) supports high levels of recombinant protein accumulation in *C. reinhardtii*. Accordingly, in varying embodiments, the polynucleotide encoding one or more colostrum/milk polypeptides is operably linked to a polynucleotide encoding a psbA promoter and 5'UTR, an atpA promoter and 5' UTR, or a psbD promoter and 5' UTR. In varying embodiments, the psbA promoter and 5' UTR, an atpA promoter and 5' UTR, a TufA promoter and 5' UTR, a atpB promoter and 5' UTR, or a psbD promoter and 5' UTR. is upstream of the polynucleotide encoding the one or more colostrum/milk polypeptides. In other embodiments the polynucleotide encoding one or more colostrum/milk polypeptides is operably linked to a polynucleotide encoding a psbA 3' UTR or a rbcL 3' UTR that is downstream of the nucleotide sequence encoding one or more colostrum/milk polypeptides. See, e.g., U.S. Patent Publication No. 2012/0309939.

In varying embodiments, the chloroplasts of photosynthetic (e.g., algal) host cells are transformed, e.g., by homologous recombination techniques, to contain and stably express one or more polynucleotides encoding one or more milk/colostrum polypeptides, as described herein, integrated into the chloroplast genome.

Transformation of the chloroplasts of photosynthetic (e.g., algal) host cells can be carried out according to techniques well known to those persons skilled in the art. Examples of such techniques include without limitation electroporation, particle bombardment, cytoplasmic or nuclear microinjection, gene gun. See, e.g., FIG. 2 of WO 2012/170125.

3. Photosynthetic Organisms

Polynucleotides encoding the colostrum/milk polypeptides can be integrated into and expressed from the chloroplast genome of a eukaryotic photosynthetic organism. The colostrum/milk polypeptides can be integrated into the genome or expressed from a plasmid of cyanobacteria. Photosynthetic organisms useful for the expression of colostrum/milk polypeptides include, without limitation, higher plant chloroplasts, algae (including microalgae), and cyanobacteria. In varying embodiments, the photosynthetic organism can be eukaryotic (e.g., higher plants and algae, including microalgae and macroalgae) or prokaryotic (e.g., cyanobacteria). Plants of interest include vascular plant (e.g., a brassica, corn, soybean, tobacco, rice, etc), and non-vascular plants (e.g., algae, including microalgae, and mosses). Embodiments of photosynthetic organisms are described above and herein.

In varying embodiments, the chloroplast, nucleus, cell and/or organism is a microalgae. Illustrative and additional microalgae species of interest include without limitation, *Achnanthes orientalis, Agmenellum, Amphiprora hyaline, Amphora coffeiformis, Amphora coffeiformis linea, Amphora coffeiformis punctata, Amphora coffeiformis taylori, Amphora coffeiformis tenuis, Amphora delicatissima, Amphora delicatissima capitata, Amphora* sp., *Anabaena, Ankistrodesmus, Ankistrodesmus falcatus, Boekelovia hooglandii, Borodinella* sp., *Botryococcus braunii, Botryococcus sudeticus, Carteria, Chaetoceros gracilis, Chaetoceros muelleri, Chaetoceros muelleri subsalsum, Chaetoceros* sp., *Chlamydomonas* sp., *Chlamydomonas reinhardtii, Chlorella anitrata, Chlorella Antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora* (strain SAG 37.88), *Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vannielii, Chlorella vulgaris, Chlorella vulgaris, Chlorella vulgaris f. tertia, Chlorella vulgaris* var. *autotrophica, Chlorella vulgaris* var. *viridis, Chlorella vulgaris* var. *vulgaris, Chlorella vulgaris* var. *vulgaris f. tertia, Chlorella vulgaris* var. *vulgaris f. viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena, Franceia* sp., *Fragilaria crotonensis, Fragilaria* sp., *Gleocapsa* sp., *Gloeothamnion* sp., *Hymenomonas* sp., *Isochrysis aff. galbana, Isochrysis galbana, Lepocinclis, Micractinium, Micractinium* (UTEX LB 2614), *Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pellicuosa, Navicula saprophila, Navicula* sp., *Nephrochloris* sp., *Nephroselmis* sp., *Nitschia communis, Nitzschia alexandrina, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Pascheria acidophila, Pavlova* sp., *Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pyramimonas* sp., *Pyrobotrys, Sarcinoid chrysophyte, Scenedesmus armatus, Schizochytrium, Spirogyra, Spirulina platensis, Stichococcus* sp., *Synechococcus* sp., *Tetraedron, Tetraselmis* sp., *Tetraselmis suecica, Thalassiosira weissflogii,* and *Viridiella fridericiana.*

In varying embodiments, the chloroplast, cell and/or organism is from a higher plant or vascularized plant. Illustrative and additional plant species of interest include without limitation, Brassicaceae (broccoli, cabbage, cauliflower, kale), Solanaceae (e.g., tomato, potato, tobacco), Phaseoleae (e.g., soybean), Zea (e.g., corn) and Oryzeae (e.g., rice).

4. Methods of Producing

Recombinant expression of proteins from heterologous polynucleotides incorporated into the chloroplast genome of a photosynthetic (e.g., algal) host cell, particularly a Chlorophyta (green algae) host cell of the genus *Chlamydomonas*, in particular *Chlamydomonas reinhardtii*, is known in the art, finds use, and is described in numerous publications, including, e.g., in Rasala and Mayfield, *Bioeng Bugs*. (2011) 2(1):50-4; Rasala, et al., *Plant Biotechnol J*. (2011) May 2, PMID 21535358; Coragliotti, et al., *Mol Biotechnol*. (2011) 48(1):60-75; Specht, et al., *Biotechnol Lett*. (2010) 32(10): 1373-83; Rasala, et al., *Plant Biotechnol J*. (2010) 8(6):719-33; Mulo, et al., *Biochim Biophys Acta*. (2011) May 2, PMID:21565160; and Bonente, et al., *Photosynth Res*. (2011) May 6, PMID: 21547493; U.S. Patent Publication No. 2012/0309939; U.S. Patent Publication No. 2010/0129394; and Intl. Publication No. WO 2012/170125. All of the foregoing references are incorporated herein by reference in their entirety for all purposes.

a. Culturing of Cells or Organisms

Techniques for culturing of microalgae and cyanobacteria and vascular plants for expression of recombinant polypeptides are known in the art and can be used for the production of milk/colostrum polypeptides. The photosynthetic organism containing the recombinant polynucleotides encoding one or more colostrum/milk polypeptides can be grown under conditions which permit photosynthesis, however, this is not a requirement (e.g., a host organism may be grown in the absence of light). In some instances, the host organism may be genetically modified in such a way that its photosynthetic capability is diminished or destroyed. In growth conditions where a host organism is not capable of photosynthesis (e.g., because of the absence of light and/or genetic modification), typically, the organism will be provided with the necessary nutrients to support growth in the absence of photosynthesis. For example, a culture medium in (or on) which an organism is grown, may be supplemented with any required nutrient, including an organic carbon source, nitrogen source, phosphorous source, vitamins, metals, lipids, nucleic acids, micronutrients, and/or an organism-specific requirement. Organic carbon sources include any source of carbon which the host organism is able to metabolize including, but not limited to, acetate, simple carbohydrates (e.g., glucose, sucrose, and lactose), complex carbohydrates (e.g., starch and glycogen), proteins, and lipids. One of skill in the art will recognize that not all organisms will be able to sufficiently metabolize a particular nutrient and that nutrient mixtures may need to be modified from one organism to another in order to provide the appropriate nutrient mix.

Organisms can be grown on a defined minimal medium (for example, high salt medium (HSM), modified artificial sea water medium (MASM), or F/2 medium) with light as the sole energy source. In other instances, the organism can be grown in a medium (for example, tris acetate phosphate (TAP) medium), and supplemented with an organic carbon source.

Organisms, such as algae, can grow naturally in fresh water or marine water. Culture media for freshwater algae can be, for example, synthetic media, enriched media, soil water media, and solidified media, such as agar. Various culture media have been developed and used for the isolation and cultivation of fresh water algae and are described in Watanabe, M. W. (2005). Freshwater Culture Media. In R. A. Andersen (Ed.), Algal Culturing Techniques (pp. 13-20). Elsevier Academic Press, 2005. Culture media for marine algae can be, for example, artificial seawater media or natural seawater media. Guidelines for the preparation of media are described in Harrison, P. J. and Berges, J. A. (2005). Marine Culture Media. In R. A. Andersen (Ed.), Algal Culturing Techniques (pp. 21-33). Elsevier Academic Press, 2005.

Culturing techniques for algae are well known to one of skill in the art and are described, for example, in Freshwater Culture Media. In R. A. Andersen (Ed.), Algal Culturing Techniques. Elsevier Academic Press, 2005. See also, Richmond and Hu, Handbook of Microalgal Culture: Applied Phycology and Biotechnology, Wiley-Blackwell; 2nd edition (Jun. 4, 2013). In varying embodiments, algae can be grown in a bioreactor or a fermenter using either sunlight or reduced carbon as an energy source.

*Chlamydomonas* sp., *Scenedesmus* sp., and *Chlorella* sp. are illustrative algae that can be cultured as described herein and can grow under a wide array of conditions.

One organism that can be cultured as described herein is a commonly used laboratory species *C. reinhardtii*. Cells of this species are haploid, and can grow on a simple medium of inorganic salts, using photosynthesis to provide energy. This organism can also grow in total darkness if acetate is provided as a carbon source. *C. reinhardtii* can be readily grown at room temperature under standard fluorescent lights. In addition, the cells can be synchronized by placing them on a light-dark cycle. Other methods of culturing *C. reinhardtii* cells are known to one of skill in the art.

b. Introduction of Polynucleotide into a Host Organism or Cell

To generate a genetically modified host cell, a polynucleotide, or a polynucleotide cloned into a vector, is introduced stably or transiently into a host cell, using established techniques, including, but not limited to, electroporation, biolistic, calcium phosphate precipitation, DEAE-dextran mediated transfection, and liposome-mediated transfection. For transformation, a polynucleotide of the present disclosure will generally further include a selectable marker, e.g., any of several well-known selectable markers such as restoration of photosynthesis, or kanamycin resistance or spectinomycin resistance.

A polynucleotide or recombinant nucleic acid molecule described herein, can be introduced into a cell (e.g., alga cell) using any method known in the art. A polynucleotide can be introduced into a cell by a variety of methods, which are well known in the art and selected, in part, based on the particular host cell. For example, the polynucleotide can be introduced into a cell using a direct gene transfer method such as electroporation or microprojectile mediated (biolistic) transformation using a particle gun, or the "glass bead method," or by pollen-mediated transformation, liposome-mediated transformation, transformation using wounded or enzyme-degraded immature embryos, or wounded or enzyme-degraded embryogenic callus (for example, as described in Potrykus, Ann. Rev. Plant. Physiol. Plant Mol. Biol. 42:205-225, 1991).

As discussed above, microprojectile mediated transformation can be used to introduce a polynucleotide into a cell (for example, as described in Klein et al., Nature 327:70-73, 1987). This method utilizes microprojectiles such as gold or tungsten, which are coated with the desired polynucleotide by precipitation with calcium chloride, spermidine or polyethylene glycol. The microprojectile particles are accelerated at high speed, into a cell using a device such as the BIOLISTIC PD-1000 particle gun (BioRad; Hercules Calif.). Methods for the transformation using biolistic methods are well known in the art (for example, as described in Christou, Trends in Plant Science 1:423-431, 1996). Microprojectile mediated transformation has been used, for example, to generate a variety of transgenic plant species, including cotton, tobacco, corn, hybrid poplar and papaya. Important cereal crops such as wheat, oat, barley, sorghum and rice also have been transformed using microprojectile mediated delivery (for example, as described in Duan et al., Nature Biotech. 14:494-498, 1996; and Shimamoto, Curr. Opin. Biotech. 5:158-162, 1994). The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, and the glass bead agitation method.

The basic techniques used for transformation and expression in photosynthetic microorganisms are similar to those commonly used for *E. coli, Saccharomyces cerevisiae* and other species. Transformation methods customized for photosynthetic microorganisms, e.g., the chloroplast of a strain of algae, are known in the art. These methods have been described in a number of texts for standard molecular biological manipulation (see Packer & Glaser, 1988, "Cyanobacteria", Meth. Enzymol., Vol. 167; Weissbach & Weissbach, 1988, "Methods for plant molecular biology," Academic Press, New York, Green and Sambrook, Molecular Cloning, A Laboratory Manual, 4th Ed., Cold Spring Harbor Press, (2012); and Clark M S, 1997, Plant Molecular Biology, Springer, N.Y.). These methods include, for example, biolistic devices (See, for example, Sanford, Trends In Biotech. (1988) .delta.: 299-302, U.S. Pat. No. 4,945,050; electroporation (Fromm et al., Proc. Nat'l. Acad. Sci. (USA) (1985) 82: 5824-5828); use of a laser beam, electroporation, microinjection or any other method capable of introducing DNA into a host cell.

Plastid transformation is a routine and well known method for introducing a polynucleotide into a plant cell chloroplast (see U.S. Pat. Nos. 5,451,513, 5,545,817, and 5,545,818; WO 95/16783; McBride et al., Proc. Natl. Acad. Sci., USA 91:7301-7305, 1994). In some embodiments, chloroplast transformation involves introducing regions of chloroplast DNA flanking a desired nucleotide sequence, allowing for homologous recombination of the exogenous DNA into the target chloroplast genome. In some instances one to 1.5 kb flanking nucleotide sequences of chloroplast genomic DNA may be used. Using this method, point mutations in the chloroplast 16S rRNA and rps12 genes, which confer resistance to spectinomycin and streptomycin, can be utilized as selectable markers for transformation (Svab et al., Proc. Natl. Acad. Sci., USA 87:8526-8530, 1990), and can result in stable homoplasmic transformants, at a frequency of approximately one per 100 bombardments of target leaves.

In some embodiments, an alga is transformed with one or more polynucleotides which encode one or more milk/colostrum polypeptides, as described herein. In one embodiment, a transformation may introduce a nucleic acid into a plastid of the host alga (e.g., chloroplast). In another embodiment, a transformation may introduce a second nucleic acid into the chloroplast genome of the host alga. In still another embodiment, a transformation may introduce two protein coding regions into the plastid genome on a single gene, or may introduced two genes on a single transformation vector.

Transformed cells can be plated on selective media following introduction of exogenous nucleic acids. This method may also comprise several steps for screening. A screen of primary transformants can be conducted to determine which clones have proper insertion of the exogenous nucleic acids. Clones which show the proper integration may be propagated and re-screened to ensure genetic stability. Such methodology ensures that the transformants contain the genes of interest. In many instances, such screening is performed by polymerase chain reaction (PCR); however, any other appropriate technique known in the art may be utilized. Many different methods of PCR are known in the art (e.g., nested PCR, real time PCR). For any given screen, one of skill in the art will recognize that PCR components may be varied to achieve optimal screening results. For example, magnesium concentration may need to be adjusted upwards when PCR is performed on disrupted alga cells to which (which chelates magnesium) is added to chelate toxic metals. Following the screening for clones with the proper integration of exogenous nucleic acids, clones can be screened for the presence of the encoded protein(s) and/or products. Protein expression screening can be performed by Western blot analysis and/or enzyme activity assays. Product screening may be performed by any method known in the art, for example mass spectrometry, SDS PAGE protein gels, or HPLC or FPLC chromatography.

The expression of the colostrum/milk protein can be accomplished by inserting a polynucleotide sequence (gene) encoding the protein or enzyme into the chloroplast genome of a microalgae. The modified strain of microalgae can be made homoplasmic to ensure that the polynucleotide will be stably maintained in the chloroplast genome of all descendants. A microalga is homoplasmic for a gene when the inserted gene is present in all copies of the chloroplast genome, for example. It is apparent to one of skill in the art that a chloroplast may contain multiple copies of its genome, and therefore, the term "homoplasmic" or "homoplasmy" refers to the state where all copies of a particular locus of interest are substantially identical. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% or more of the total soluble plant protein. The process of determining the plasmic state of an organism of the present disclosure involves screening transformants for the presence of exogenous nucleic acids and the absence of wild-type nucleic acids at a given locus of interest.

c. Vectors

Numerous suitable expression vectors are known to those of skill in the art. The following vectors are provided by way of example; for bacterial host cells: pQE vectors (Qiagen), pBluescript plasmids, pNH vectors, lambda-ZAP vectors (Stratagene), pTrc99a, pKK223-3, pDR540, and pRIT2T (Pharmacia); for eukaryotic host cells: pXT1, pSG5 (Stratagene), pSVK3, pBPV, pMSG, pET21a-d(+) vectors (Novagen), and pSVLSV40 (Pharmacia). However, any other plasmid or other vector may be used so long as it is compatible with the host cell. For example, illustrative vectors including without limitation, psbA-kanamycin vector can be used for the expression of one or more milk/colostrum proteins, e.g., in a cyanobacteria or in the plastids of a photosynthetic organism.

Knowledge of the chloroplast genome of the host organism, for example, *C. reinhardtii*, is useful in the construction of vectors for use in the disclosed embodiments. Chloroplast vectors and methods for selecting regions of a chloroplast genome for use as a vector are well known (see, for example, Bock, J. Mol. Biol. 312:425-438, 2001; Staub and Maliga, Plant Cell 4:39-45, 1992; and Kavanagh et al., Genetics 152:1111-1122, 1999, each of which is incorporated herein by reference). The entire chloroplast genome of *C. reinhardtii* is available to the public on the world wide web, at the URL "biology.duke.edu/chlamy_genome/-chloro.html" (see "view complete genome as text file" link and "maps of the chloroplast genome" link; J. Maul, J. W. Lilly, and D. B. Stern, unpublished results; revised Jan. 28, 2002; to be published as GenBank Acc. No. AF396929; and Maul, J. E., et al. (2002) The Plant Cell, Vol. 14 (2659-2679)). Generally, the nucleotide sequence of the chloroplast genomic DNA that is selected for use is not a portion of a gene, including a regulatory sequence or coding sequence. For example, the selected sequence is not a gene that if disrupted, due to the homologous recombination event, would produce a deleterious effect with respect to the chloroplast. For example, a deleterious effect on the replication of the chloroplast genome or to a plant cell containing the chloroplast. In this respect, the website containing the *C. reinhardtii* chloroplast genome sequence also provides maps showing coding and non-coding regions of the chloroplast genome, thus facilitating selection of a sequence useful for constructing a vector (also described in Maul, I. E., et al. (2002) The Plant Cell, Vol. 14 (2659-2679)). For example, the chloroplast vector, p322, is a clone extending from the Eco (Eco RI) site at about position 143.1 kb to the Xho (Xho I) site at about position 148.5 kb (see, world wide web, at the URL "biology.duke.edu/chlamy_genome/chloro.html", and clicking on "maps of the chloroplast genome" link, and "140-150 kb" link; also accessible directly on world wide web at URL "biology.duke.edu/chlam-y/chloro/chloro140.html").

For expression of the colostrum/milk polypeptide in a host, an expression cassette or vector may be employed. The expression vector will comprise a transcriptional and translational initiation region, which may be inducible or constitutive, where the coding region is operably linked under the transcriptional control of the transcriptional initiation region, and a transcriptional and translational termination region. These control regions may be native to the gene, or may be derived from an exogenous source. Expression vectors generally have convenient restriction sites located near the promoter sequence to provide for the insertion of nucleic acid sequences encoding exogenous proteins. A selectable marker operative in the expression host may be present in the vector.

The nucleotide sequences disclosed herein may be inserted into a vector by a variety of methods. In the most common method the sequences are inserted into an appropriate restriction endonuclease site(s) using procedures commonly known to those skilled in the art and detailed in, for example, Green and Sambrook, Molecular Cloning, A Laboratory Manual, 4th Ed., Cold Spring Harbor Press, (2012) and Ausubel et al., Current Protocols in Molecular Biology, John Wiley & Sons (through 2013).

Further provided are host cells that can be transformed with vectors. One of skill in the art will recognize that such transformation includes transformation with circular vectors, linearized vectors, linearized portions of a vector, or any combination of the above. Thus, a host cell comprising a vector may contain the entire vector in the cell (in either circular or linear form), or may contain a linearized portion of a vector of the present disclosure.

d. Colostrum/Milk Protein Expression

To determine percent total soluble protein, immunoblot signals from known amounts of purified protein can be compared to that of a known amount of total soluble protein lysate. Other techniques for measuring percent total soluble protein are known to one of skill in the art. For example, an ELISA assay or protein mass spectrometry (for example, as described in Varghese, R. S. and Ressom, H. W., Methods Mol. Bio. (2010) 694:139-150) can also be used to determine percent total soluble protein.

In some embodiments, the one or more colostrum/milk polypeptides are produced in a genetically modified host cell at a level that is at least about 0.5%, at least about 1%, at least about 1.5%, at least about 2%, at least about 2.5%, at least about 3%, at least about 3.5%, at least about 4%, at least about 4.5%, or at least about 5% of the total soluble protein produced by the cell. In other embodiments, the colostrum/milk compound is produced in a genetically modified host cell at a level that is at least about 0.15%, at least about 0.1%, or at least about 1% of the total soluble protein produced by the cell. In other embodiments, the colostrum/milk compound is produced in a genetically modified host cell at a level that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, or at least about 70% of the total soluble protein produced by the cell.

Expression of the milk/colostrum polypeptides in the photosynthetic (e.g., algal) host cell can be detected using any method known in the art, e.g., including immunoassays (ELISA, Western Blot) and/or nucleic acid assays (RT-PCR). Sequences of expressed polypeptides can be confirmed using any method known in the art (e.g., mass spectrometry).

Milk/colostrum polypeptides expressed in a photosynthetic (e.g., algal) host cell are generally properly folded without performing denaturation and refolding. Furthermore, the polypeptides expressed in the chloroplast genome are not glycosylated, so coding sequences do not need to be altered to remove glycosylation sites and glycosylated moieties do not need to be removed post-translationally.

Milk/colostrum polypeptides expressed in a photosynthetic (e.g., algal chloroplasts and cyanobacteria) host can have a phosphorylation pattern, even if different from the natively expressed protein, allows for bioactivity. Similar polypeptides expressed in the cytoplasm of photosynthetic organisms may not correctly phosphorylated, and thus not biologically active. The phosphorylation machinery of chloroplasts and cyanobacteria can modified to increase or decrease the degree of phosphorylation of a mammalian protein produced in those compartments.

e. Colostrum/Milk Protein Bioactivity

The bioactivity of the expressed colostrum milk polypeptides can be determined using any method known in the art. For example, lysozyme bioactivity can be measured by determining the activity of cell lysates or purified polypeptide to effect killing of gram positive bacteria (e.g., micrococcus cells). See, e.g., Ito, et al., *Chem Pharm Bull* (Tokyo). 1992 June; 40(6):1523-6 and Mörsky, et al., *Anal Biochem*. 1983 January; 128(1):77-85. Lactadherin bioactivity can be determined by measuring binding to phosphatidylserine. See, e.g., Otzen, et al., *Biochim Biophys Acta*. (2012) 1818(4):1019-27; Hou, et al., *Vox Sang*. 2011 February; 100(2):187-95 and Dasgupta, et al., *Transl Res*. 2006 July; 148(1):19-25. The bioactivity of osteopontin can be measured by the ability of osteopontin to adhere to human embryonic 293 cells when in the presence of the divalent cations, $Mg^{2+}$ or $Mn^{2+}$ but not $Ca^{2+}$. See, e.g., Hu, et al, *J Biol Chem*. (1995) 270(17):9917-25; and Agnihotri, et al., *J Biol Chem* (2001) 276:28261-28267. CD14 bioactivity can be determined by measuring binding to lipopolysaccharide (LPS). See, e.g., Wright, et al., *Science*. 1990 Sep. 21; 249(4975):1431-3. Cathelicidin-1 activity can be determined using an antimicrobial assay and measuring luminescence. See, e.g., Sue, et al. *Infect Immun*. 2000 May; 68(5) 2748-2755. M-SAA3 bioactivity can be determined by measuring the induction of mucin3 expression by intestinal epithelial cells. See, e.g. Manuell. et al., *Plant Biotechnology J*, 2007 May; 5(3):402-12. Lingual antimicrobial peptide (LAP) and cathelicidin-1 bioactivity can be determined by measuring bactericidial activity. See, Tomasinsig, et al., *J Pept Sci*. 2012 February; 18(2):105-13. Alpha-lactalbumin bioactivity can be determined by measuring lactase synthase activity. See, Fitzgerald, et al., *Anal Biochem*. 1970 July; 36(1):43-61. The bioactivity of a polypeptide is determined in a test assay known in the art and the bioactivity of the test polypeptide can be compared to a positive control (e.g., a known bioactive polypeptide or a native polypeptide) and a negative control (e.g., no peptide or a known biologically inactive polypeptide). In varying embodiments, colostrum/milk polypeptides produced in the chloroplast of photosynthetic organisms are characterized by at least 50%, 75%, 85%, 90%, 95% 98%, 99% and even up to 100% of the level of bioactivity of the natural colostrum-derived counterpart protein.

5. Compositions

Further provided are compositions comprising the one or more colostrum/milk polypeptides. Generally, the colostrum/milk polypeptides need not be purified or isolated from the host cell. A distinct advantage of the compositions and methods described herein is that administration of the bioactive protein-expressing organism, without purification or isolation, to a patient, e.g., a human or non-human mammal, confers a clinical or nutritional benefit. For example, administration of photosynthetic organisms comprising chloroplast-expressed milk/colostrum polypeptides, e.g. osteopontin, to the gastrointestinal tract, e.g., orally, and is efficiently absorbed and assimilated into bodily tissues such as bone and immune cells. Accordingly, in varying embodiments, the compositions comprise the photosynthetic (e.g., algal) host cells which have been engineered to express one or more colostrum/milk polypeptides. In varying embodiments, the compositions are edible by a mammal. The edible compositions can take the form of a liquid or beverage (e.g., infant formula), a food, a feed (e.g., kibble), a food supplement, a nutraceutical (e.g., a pill). In varying embodiments, the compositions comprise a compressed algal cake (e.g., a compressed solid mass of algal cells), algal paste and/or algal powder. In varying embodiments, the compositions are lyophilized or spray dried. In some embodiments, the photosynthetic organisms (e.g., algae) are lyophilized or spray-dried prior to the addition to an edible composition, e.g., a food, beverage or tablet consumable by a mammal, e.g., a human, a canine, a feline. In some embodiments, the photosynthetic organisms (e.g., algae) are formulated into a wet paste prior to the addition to an edible composition, e.g., a food, beverage or tablet consumable by a mammal, e.g., a human, a canine, a feline. In some embodiments, the photosynthetic organisms (e.g., algae) are formulated into a powder to be sprinkled onto or into an edible composition, e.g., a food, beverage or tablet consumable by a mammal, e.g., a human, a canine, a feline. In some embodiments the photosynthetic organisms (e.g., algae) are blended or mixed into an edible composition, e.g., a food, beverage or tablet consumable by a mammal, e.g., a human, a canine, a feline.

EXAMPLES

The following examples are offered to illustrate, but not to limit the claimed invention.

Example 1

Chloroplast Expression of Osteopontin

A cDNA encoding for bovine osteopontin was synthesized in *C. reinhardtii* chloroplast codon bias and ligated into a *C. reinhardtii* chloroplast transformation vector. This vector directed the osteopontin cDNA into the chloroplast genome via homologous recombination and allowed the cDNA to directly replace the psbA gene. This vector also contained regulatory elements, promoters and untranslated regions (UTRs) that ensure the stable expression and translation of the osteopontin mRNA.

The transformation vector containing the osteopontin cDNA was introduced into the chloroplast genome by first coating the vector onto 1 µM gold particles and then shooting the gold particles into *C. reinhardtii* cells that had been plated on Tris-Acetate-phosphate (TAP) plates containing 100 µg/mL kanamycin with a particle gun from Bio-Rad laboratory. Places were incubated in the dark for 24 hours followed by an incubation in light with an intensity of 4000 lux for 2 weeks. Transformed algae formed colonies following the incubation. Colonies from the transformation was patched onto TAP plates containing 150 µg/mL kanamycin.

To ensure that colonies from algal chloroplast transformations contained our gene of interest PCR gene screens were done using a forward primer, 5'-gtgctaggtaactaacgttt-gattttt-3' (SEQ ID NO: 26), that anneals to the untranslated region of the psbA gene that is used to drive the accumulation of the osteopontin protein and a reverse primer, 5'-CTGAATCACCACGACCATCATTAGC-3' (SEQ ID NO: 27), that anneals to the chloroplast codon optimized osteopontin cDNA. The PCR yields a product that is 500 bp. The chloroplast also contains up to 80 copies of its genome. To ensure that the osteopontin gene is integrated into all copies of the chloroplast genome, a PCR screen was done to ensure that the gene that was being replaced was completely removed. Two sets of primers were used: 1. A control set of primers to ensure that the PCR worked, amplifies the DNA that encodes for the 16s rRNA with a forward primer 5'-ccgaactgaggttgggttta-3' (SEQ ID NO: 28) and a reverse primer 5'-GGGGGAGCGAATAGGATTAG-3' (SEQ ID NO: 29). 2. A set of primers to amplify the M-SAA3 gene that currently resided in the psbA locus of the untransformed strain with a forward primer 5'-gtgctaggtaactaacgtttgattttt-3' (SEQ ID NO: 26) and a reverse primer 5'-TCTTCACG-TACTTGGTCACGTGTCATACC-3' (SEQ ID NO: 30). The loss of the M-SAA3 PCR product indicates a strain that is homoplasmic for osteopontin.

Homoplasmic cell lines were grown to a final volume of 20 L and harvested by continuous flow centrifugation. To isolate the osteopontin proteins from the *C. reinhardtii* cell, the harvested cells were re-suspended in a buffer that contained 50 mM Tris-HCl pH8.0, 400 mM NaCl, and 0.5% Tween 20. Cells were lysed at 4° C. by sonication with an amplitude of 25% with a pulse of 30 seconds followed by a rest period of 30 seconds. The sonication cycle was repeated for a total of 16 minutes.

Once lysed, cell debris, insoluble proteins, lipids, and carbohydrates were separated by centrifugation at 20,000 g for 15 mins at 4° C. Once separated soluble protein was mixed with 1mL of anti-M2-Flag resin. Algal total soluble lysate and resin were allowed to mix for 1 hour. Following the binding of the osteopontin protein to the anti-M2-flag resin, resin was washed and unbound fractions removed. Osteopontin protein was eluted from the flag resin using an elution buffer that contains 100 mM glycine-HCl pH3.5 and 400 mM NaCl. Elutions were analyzed by Western blot to ensure the presence of the protein (FIG. 11). Protein was concentrated and used for Mass spectrometry LC-LC-MS analysis to identify the protein as authentic osteopontin (FIG. 14). Mass spectrometry was used to identify if any osteopontin amino acids were phosphorylated in the chloroplast produced protein (FIG. 14B). A number of amino acids could be identified as being phosphorylated, and all of these appear to be the same amino acids that are phosphorylated in the native bovine protein (FIG. 14B). This unexpected result demonstrated that chloroplasts are able to recognize mammalian phosphorylation signals and correctly add phosphates at only the appropriate amino acids on the osteopontin protein. Osteopontin produced in algae by translation in the cytoplasm from a nuclear encoded gene is not phosphorylated in algae cells.

Figure 15:
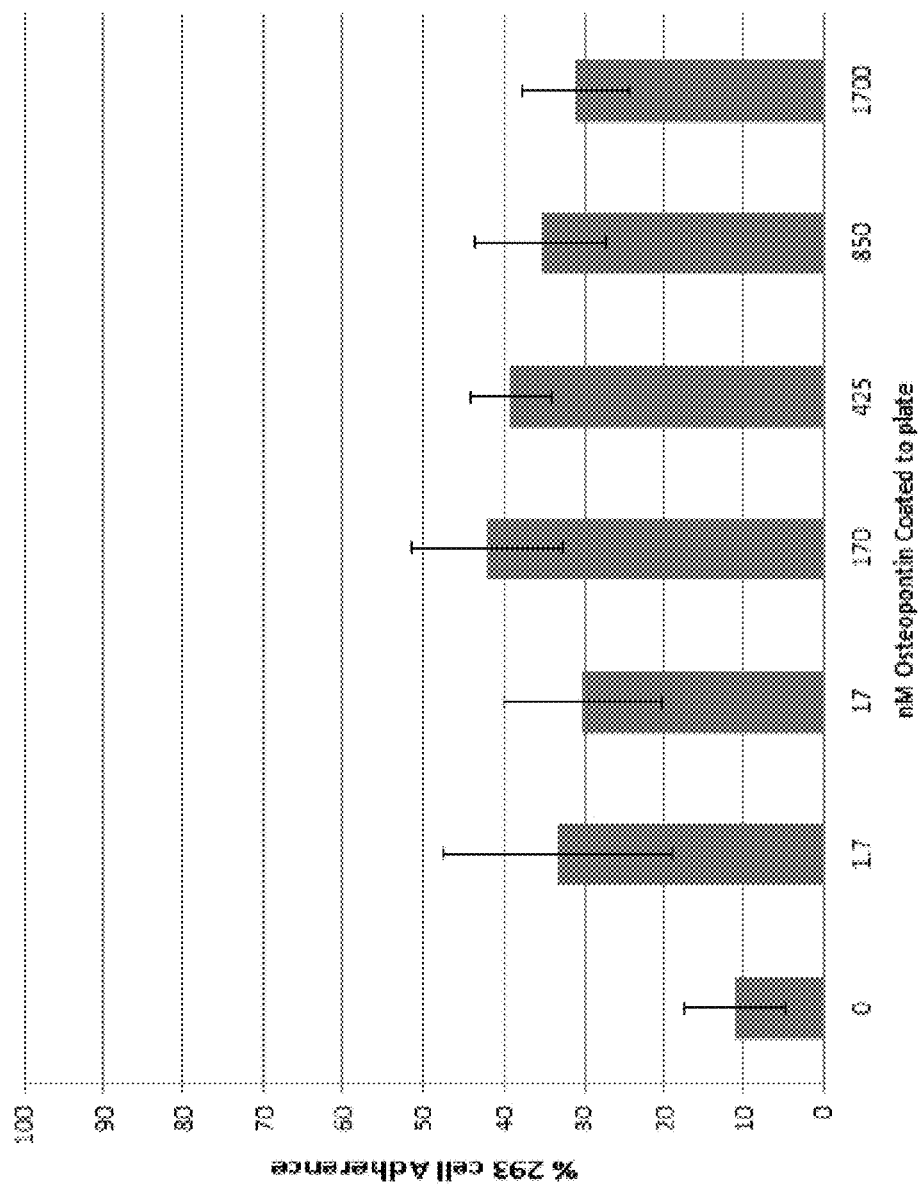
FIG. 15 illustrates cell adhesion bioactivity assay for bovine osteopontin expressed from the chloroplast genome. Purified chloroplast bovine osteopontin was coated on a microtiter plate and cell adhesion assays performed. 293 kidney cells in the presence of 2 mM $Mg^{2+}$ were incubated in microtiter plates coated with chloroplast produced bovine osteopontin. Unbound cells were washed away and 100 µL culture medium was added to each well. 10 µL of wst-8 reagent (cell identification reagent) was added to each well and plates were incubated for 1 hour. Following incubation the absorbance was measured at 450 nm and compared to a standard curve to determine the percent of cells that bound the algal produced chloroplast osteopontin in each well. Chloroplast-expressed bovine osteopontin was bound by up to 40% of the cells (170 nM osteopontin).

To determine if osteopontin was bioactive a cell adhesion assay was performed. Increasing concentrations of osteopontin (1.7 nM to 1700 nM) were coated in a 96-well microtiter plate. Once coated $1 \times 10^4$ 293 kidney cells were incubated in the wells with RPMI media that was supplemented with 10% fetal bovine serum and 2 mM $MgCl_2$. Unbound cells were then washed off with PBS followed by the addition of 100 µL, of RPMI media that was supplemented with 10% fetal bovine serum. Immediately, 100 µL, of a wst-8 reagent (Cell counting kit-8) was added to each well to determine what percentage of cells that were bound to the plate compared to the controls (FIG. 15). As a control a well had no cells added and another well had the total number of cells added to represent 100% adherence.

Example 2

Chloroplast Expression of Lactadherin

A cDNA encoding for bovine lactadherin was synthesized in *C. reinhardtii* chloroplast codon bias and ligated into a *C. reinhardtii* chloroplast transformation vector. This vector directed the lactadherin cDNA into the chloroplast genome via homologous recombination and allowed the cDNA to directly replace the psbA gene. This vector also contained regulatory elements, untranslated regions (UTRs) that ensure the stable expression of the lactadherin mRNA.

The transformation vector containing the lactadherin cDNA was introduced into the chloroplast genome by first coating the vector onto 1 µM gold particles and then shooting the gold particles into *C. reinhardtii* cells that had been plated on Tris-Acetate-phosphate (TAP) plates containing 100 µg/mL kanamycin with a particle guy from Bio-Rad laboratory. Places were incubated in the dark for 24 hours followed by an incubation in light with an intensity of 4000 lux for 2 weeks. Transformed algae formed colonies following the incubation. Colonies from the transformation was patched onto TAP plates containing 150 µg/mL kanamycin.

Figure 12:
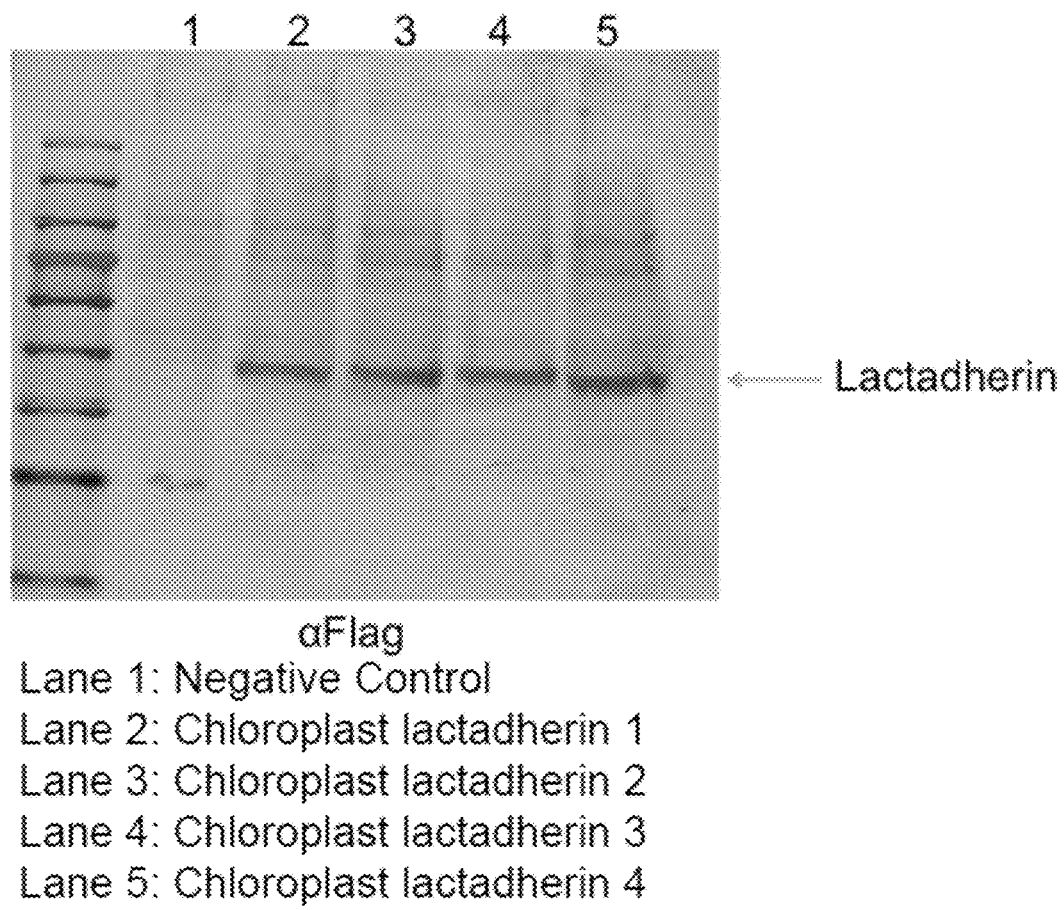
FIG. 12 illustrates a Western blot analysis of transgenic algae strains whose chloroplast genome has been transformed with a flag tagged lactadherin gene. Westerns probed with an anti-flag antibody. Lane 1 Negative control. Lanes 2-5: Independent transgenic strains.
Figure 13:
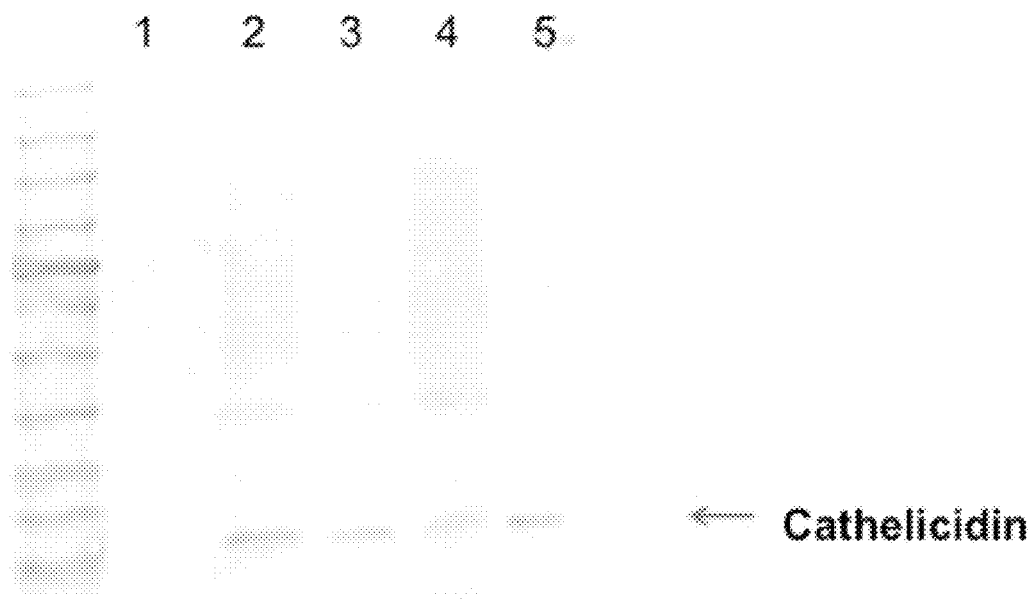
FIG. 13 illustrates a Western blot analysis of transgenic algae strains whose chloroplast genome has been transformed with a flag tagged cathelicidin-1 gene. Westerns probed with an anti-flag antibody. Lane 1 Negative control. Lanes 2-5: Independent transgenic strains.

To ensure that colonies from algal chloroplast transformations contained our gene of interest PCR gene screens were done using a forward primer, 5'-gtgctaggtaactaacgtttgattttt-3' (SEQ ID NO: 26), that anneals to the untranslated region of the psbA gene that is used to drive the accumulation of the lactadherin protein and a reverse primer, 5'-CCTGAAGTCCAAGCATTAACAATACC-3' (SEQ ID NO: 31), that anneals to the chloroplast codon optimized cDNA. The PCR yields a product that is 500 bp (FIG. 12). The chloroplast also contains up to 80 copies of its genome. To ensure that the gene that lactadherin is integrated into all copies of the chloroplast genome a PCR screen was done to ensure that the gene being replaced was completely removed. Two sets of primers were used: 1. A control set of primers to ensure that the PCR worked amplifies the DNA that encodes for the 16s rRNA with a forward primer 5'-ccgaactgaggttgggttta-3' (SEQ ID NO: 28) and a reverse primer 5'-GGGGGAGCGAATAGGATTAG-3' (SEQ ID NO: 29). 2. A set of primers to amplify the M-SAA3 gene that currently resided in the psbA locus of the untransformed strain with a forward primer 5'-gtgctaggtaactaacgtttgattttt-3' (SEQ ID NO: 26) and a reverse primer 5'-TCTTCACG-TACTTGGTCACGTGTCATACC-3' (SEQ ID NO: 30). The loss of the M-SAA3 PCR product indicates a strain that is homoplasmic for lactadherin.

Homoplasmic cell lines were grown to a final volume of 20 L and harvested by continuous flow centrifugation. The lactadherin proteins were purified from the *C. reinhardtii* cell by re-suspending the cell pellet in a buffer that contained 50 mM Tris-HCl pH8.0, 400 mM NaCl, and 0.5% Tween 20. Cells were lysed at 4° C. by sonication with an amplitude of 25% with a pulse of 30 seconds followed by a rest period of 30 seconds. The sonication cycle was repeated for a total of 16 minutes.

Once lysed cell debris, insoluble proteins, lipids, and carbohydrates were separated by centrifugation at 20,000 g for 15 mins at 4° C. Once separated soluble protein was mixed with 1mL of anti-M2-Flag resin. Algal total soluble lysate and resin were allowed to mix for 1 hour. Following the binding of the lactadherin protein to the anti-M2-flag resin, resin was washed and unbound fractions removed. Lactadherin protein was eluted from the flag resin using an elution buffer that contains 100 mM glycine-HCl pH3.5 and 400 mM NaCl. Elutions were analyzed by Western blot to ensure the presence of the protein (FIG. 12). Protein was concentrated and used for Mass spectrometry LC-LC-MS analysis to identify the protein as lactadherin. Mass spectrometry was also used to identify any phosphorylated amino acids. No phosphorylated amino acids were identified in lactadherin.

Figure 16:
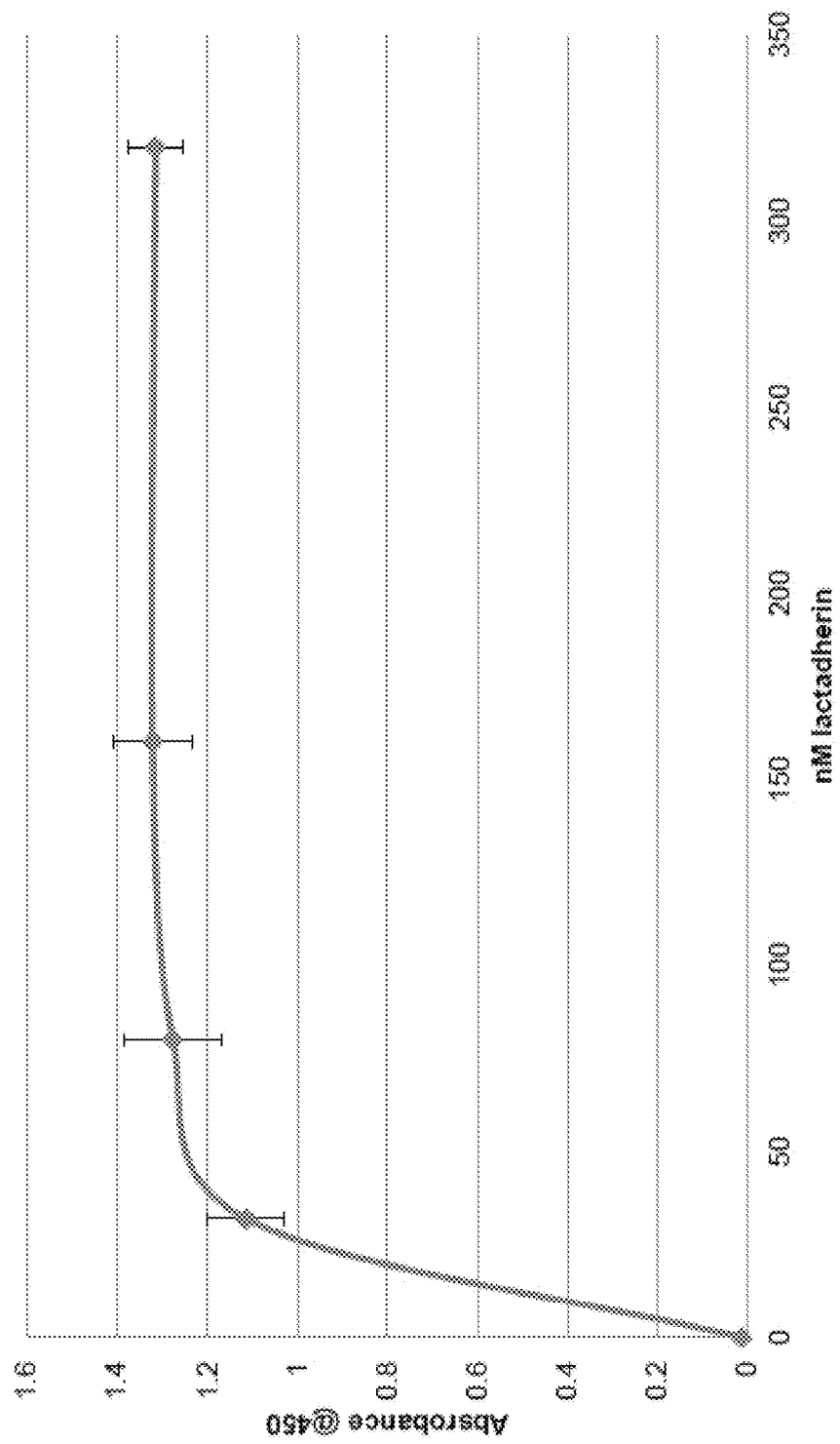
FIG. 16 illustrates bioactivity of lactadherin expressed from the chloroplast genome in binding to phosphatidylserine.

To determine whether algal chloroplast-expressed lactadherin is bioactive, an activity assay was performed. Lactadherin contains a phosphatidylserine-binding domain is required for the protein's function in cell adhesion. FIG. 16 illustrates bioactivity of lactadherin expressed from the chloroplast genome in binding to phosphatidylserine. Microtiter plates were coated with 3 µg/ml of phosphatidyl-L-serine in methanol and methanol allowed to evaporate. Increasing titers of lactadherin from 30 nM up to 350 nM of lactadherin-FLAG were incubated with immobilized phosphatidyl-L-serine for 1 hour. Following incubation unbound protein was washed from the wells. The amount of bound FLAG-tagged protein was quantitated using anti-FLAG antibodies conjugated to horseradish peroxidase (HRP). Lactadherin binds to phosphatidylserine, indicating that algae chloroplast expressed lactadherin is bioactive.

Example 3

Cyanobacteria Expression of Osteopontin and Mammary Associated Serum Amyloid A3 (M-SAA3)

Figure 17:
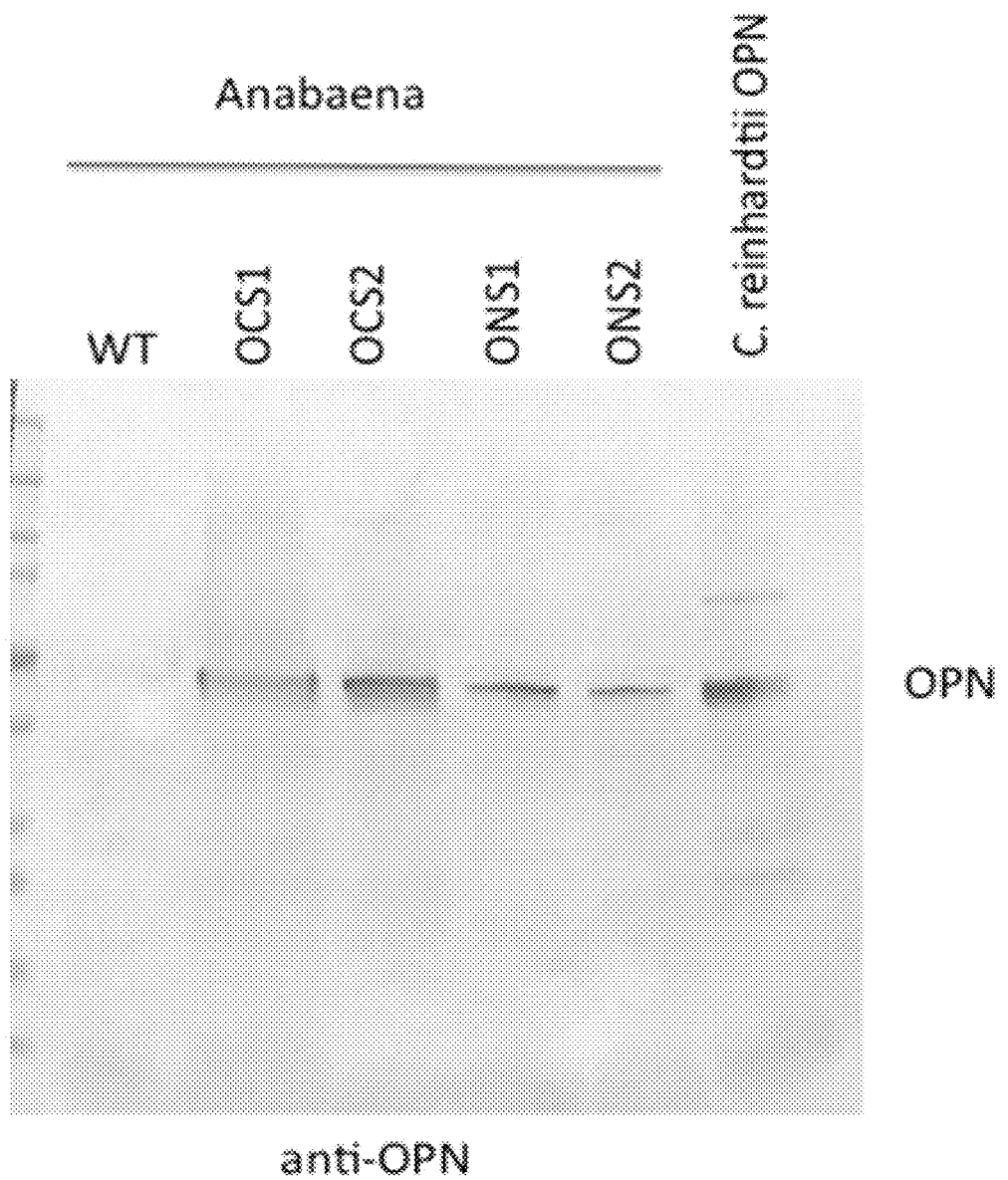
FIG. 17 illustrates a Western blot showing the accumulation of bovine osteopontin protein in the cyanobacteria *Anabaena*. Lane 1 contains wild-type *anabaena*. Lanes 2 and 3 contain independent *anabaena* transformations transformed with an osteopontin gene containing a chloroplast codon bias. Lanes 4 and 5 contain independent *anabaena* transformations that were transformed with an osteopontin gene coded in a nuclear genome bias. Lane 6 contains a transgenic *Chlamydomonas reinhardtii* strain accumulating osteopontin that is serving as a positive control. Transgenic protein was detected using a rabbit polyclonal antibody directed against bovine osteopontin.
Figure 18:
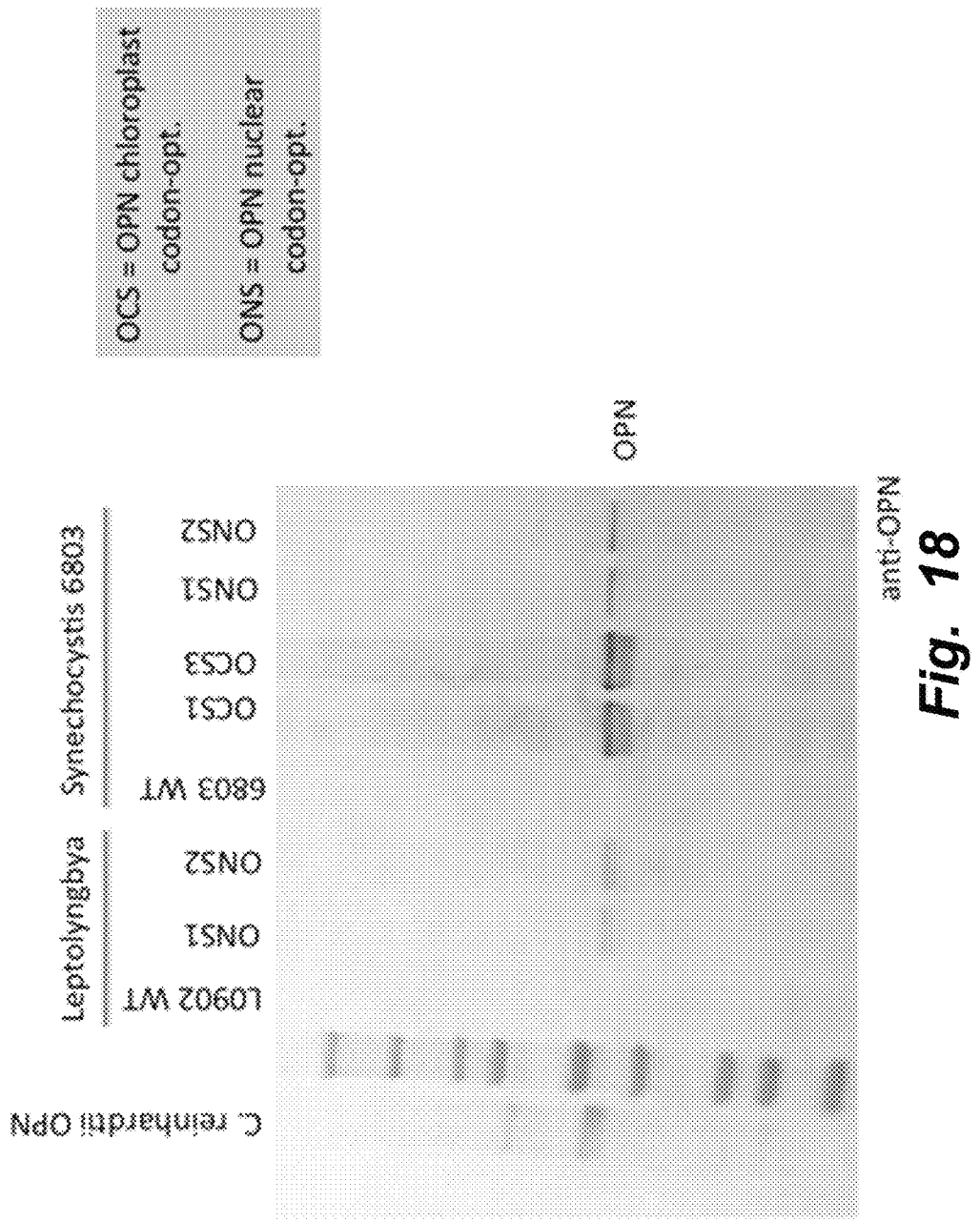
FIG. 18 illustrates a Western blot showing the accumulation of bovine osteopontin in the cyanobacteria *Leptolyngbya* and *Synechocystis* 6803. Lane 1 contains a transgenic *Chlamydomonas reinhardtii* strain accumulating bovine osteopontin that is serving as a positive control. Lane 2 contains a Protein Ladder to serve as a size standard. Lane 3 contains wild-type *Leptolyngbya*. Lane 4 and 5 contain *Leptolyngbya* transformed with a bovine osteopontin gene that contains a nuclear codon bias. Lane 6 contains wild-type *Synechocystis* 6803. Lane 7 and Lane 8 contain independent transgenic *Synechocystis* 6803 strains transformed with a bovine osteopontin that was coded in a chloroplast codon bias. Lane 9 and 10 contain transgenic *Synechocystis* 6803 transformed with a bovine osteopontin gene coded in a nuclear codon bias.
Figure 19:
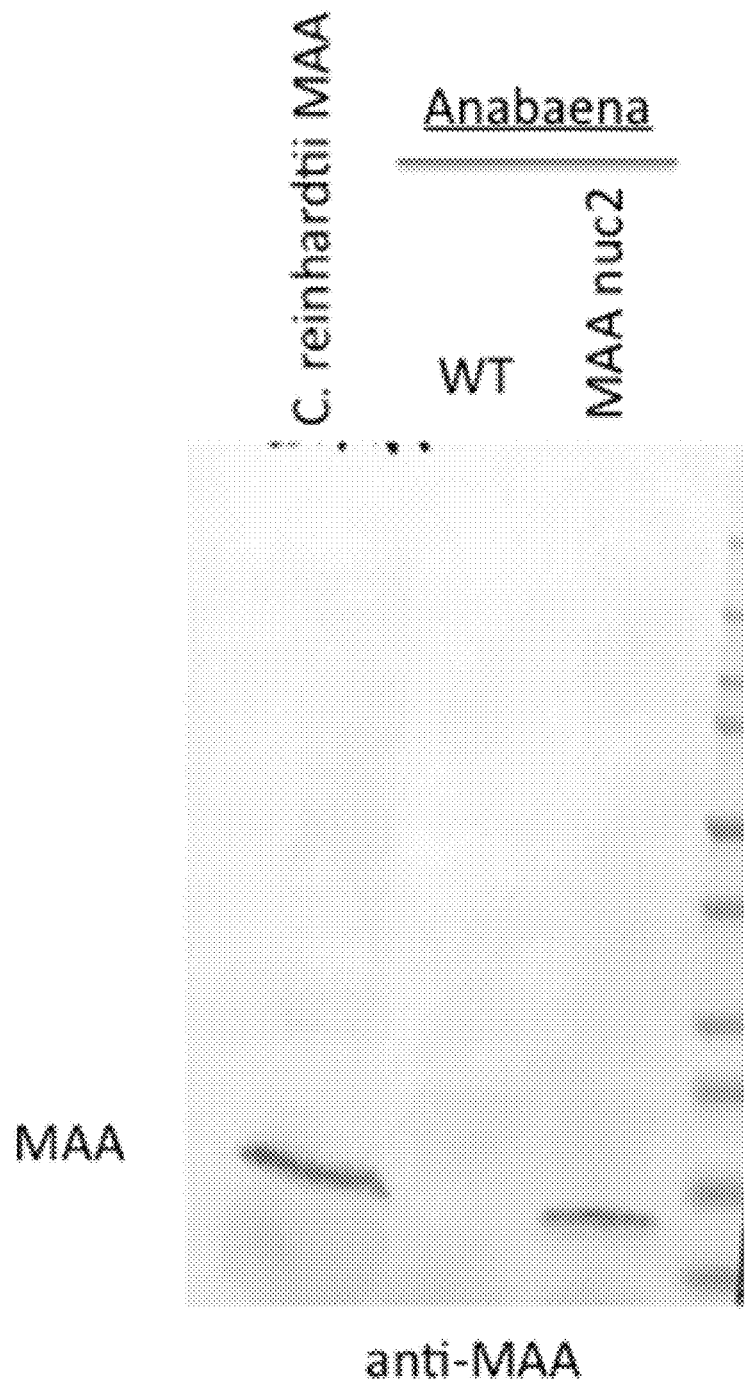
FIG. 19 illustrates a Western blot showing the accumulation of M-SAA3 in the cyanobacteria *Anabaena*. Lane 1 contains a transgenic *Chlamydomonas reinhardtii* strain transformed with the mammary-associated serum amyloid A3 (M-SAA3) gene. Lane 2 contains wild-type *anabaena*. Lane 3 contains a transgenic *anabaena* strain transformed with a M-SAA3 gene that was coded in a nuclear codon bias. Westerns were detected using a polyclonal antibody directed against the M-SAA3 protein.
Figure 20:
FIG. 20 illustrates a Western blot showing the accumulation of M-SAA3 in *Synechococcus elongatus* 7942. Lane 1 contains wild-type *Synechococcus elongatus* 7942. Lane 2 contains a transgenic *Synechococcus elongatus* 7942 transformed with the M-SAA3 gene that has not been induced for protein accumulation. Lane 3 contains a transgenic *Synechococcus elongatus* 7942 transformed with the M-SAA3 gene that has been induced to accumulate MAA protein.

A gene coding for bovine osteopontin was placed in a DNA vector allowing for the recombinant gene to be transcribed and subsequently translated into the osteopontin protein. FIG. 17 demonstrates the production of osteopontin in the cyanobacteria *Anabaena*. Osteopontin protein was detected on the Western blots using an anti-osteopontin antibody. Lane 1 contains wild-type *anabaena* while lanes 2 and lanes 3 contain a transgenic *anabaena* strain expressing a recombinant gene coding for the chloroplast codon optimized osteopontin gene. Lanes 4 and lanes 5 contain a transgenic *anabaena* strain expressing a recombinant gene coding for the nuclear optimized osteopontin gene. Lane 6 contains a transgenic *C. reinhardtii* strain expressing osteopontin in the chloroplast that is serving as the positive control. FIG. 18 demonstrates the expression of osteopontin in two additional cyanobacteria strains (*Leptolyngbya* and *Synechocystis* 6803). Western blots were probed with an anti-osteopontin antibody. Lane 1 contains a transgenic *C. reinhardtii* strain expressing osteopontin in the chloroplast that is serving as the positive control. Lane 2 is the protein ladder. Lane 3 is the wild-type *Leptolyngba* negative control. Lane 3 and lane 4 are transgenic *Leptolyngba* strains expressing a nuclear codon optimized osteopontin gene. Lane 5 is a wild-type *Synechocystis* 6803 that is serving as a negative control. Lane 6 and lane 7 contain a transgenic *Synechocystis* 6803 strain expressing a recombinant gene coding for the chloroplast codon optimized osteopontin gene. Lanes 8 and lanes 9 contain a transgenic *Synechocystis* 6803 strain expressing a recombinant gene coding for the nuclear optimized osteopontin gene. FIG. 19 demonstrates the production of M-SAA3 in the cyanobacteria *anabaena*. Western blots were detected with an anti-MAA antibody. Lane 1 contains a transgenic *C. reinhardtii* strain expressing the M-SAA3 protein in the chloroplast. Lane 2 contains wild-type *anabaena* which serves as a negative control. Lane 3 contains a transgenic *anabaena* strain that is expressing a nuclear codon optimized M-SAA3 gene. FIG. 20 is a Western blot demonstrating the production of M-SAA3 in the cyanobacteria, *Synechococcus elongatus* 7942. Lane 1 contains the wild-type *Synechococcus elongatus* 7942 serving as a negative control. Lane 2 contains a transgenic *Synechococcus elongatus* 7942 strain that is expressing the M-SAA3 recombinant gene that has not been induced by F41. Lane 3 contains a transgenic *Synechococcus elongatus* 7942 strain that is expressing the MAA recombinant gene that has been induced by F41.

Example 4

Co-Expression of Nuclear Mammary Associated Serum Amyloid A3 (M-SAA3) and Chloroplast Osteopontin in Chloroplast A cDNA encoding for bovine osteopontin was synthesized in *C. reinhardtii* chloroplast codon bias and ligated into a *C. reinhardtii* chloroplast transformation vector. The transformation vector containing the osteopontin cDNA was introduced into the chloroplast genome of *C. reinhardtii* cells by particle bombardment. Transformed algae formed colonies following two weeks incubation.

To ensure that colonies from algal chloroplast transformations contained our gene of interest PCR gene screens were done using a forward primer, 5' gtgctaggtaactaacgttt-gattttt-3' (SEQ ID NO: 26) and a reverse primer, 5' GGGGGAGCGAATAGGATTAG-3' (SEQ ID NO: 29). The PCR yields a product that is approximately 700 bp. To ensure that the osteopontin is integrated into all copies of the chloroplast genome a PCR screen was done to ensure that the gene that was being replaced was completely removed. Two sets of primers were used: 1. A control set of primers to ensure that the PCR reaction worked with a forward primer 5'-ccgaactgaggttgggttta-3' (SEQ ID NO: 28 and a reverse primer 5' GGGGGAGCGAATAGGATTAG-3' (SEQ ID NO: 29) and a set of primers to amplify the M-SAA3 gene that resided in the psbA locus of the untransformed strain with a forward primer 5' ggaaggggaggacgtaggta-cataaa-3' (SEQ ID NO: 32) and a reverse primer 5'-tta-gaacgtgttttgttcccaat-3' (SEQ ID NO: 33). The loss of the M-SAA3 PCR product indicates a strain that is homoplasmic for osteopontin.

A cDNA encoding for bovine M-SAA3 was synthesized in *C. reinhardtii* nuclear codon bias and ligated into a *C. reinhardtii* nuclear transformation vector. The transformation vector containing the M-SAA3 cDNA was introduced into the nuclear genome of the homoplasmic osteopontin-transformed strain by electroporating it into *C. reinhardtii* cells. Transformed algae formed colonies following the incubation. Thus, the osteopontin expression construct was stably transformed into the chloroplast genome and the M-SAA3 expression cassette was transformed into the nuclear genome of the same cell.

Clones were checked by Western blot for the presence of both the M-SAA3 protein using an anti M-SAA3 antibody and the osteopontin protein using an anti-flag antibody (FIG. 21). Clones 1-6 of FIG. 21 demonstrate strains of algae that produce both the M-SAA3 protein and the osteopontin protein.

The commonly owned, co-pending application International Appl. No. PCT/US2015/016596, entitled "COLOSTRUM/MILK PROTEIN COMPOSITIONS," filed on Feb. 19, 2015 is explicitly incorporated by reference in its entirety for its teachings regarding expression of mammalian colostrum/milk proteins from the nucleus of a photosynthetic organism.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A microalgal chloroplast comprising a polynucleotide encoding mammalian osteopontin integrated into the chloroplast genome, wherein the osteopontin polypeptide has at least 90% sequence identity to a polypeptide sequence selected from the group consisting of SEQ ID NO:8, SEQ ID NO:18, SEQ ID NO:20 and SEQ ID NO:22, wherein the chloroplast expresses a phosphorylated and bioactive osteopontin polypeptide.

2. The chloroplast of claim 1, wherein the chloroplast is from a green algae.

3. The chloroplast of claim 1, wherein the microalgal chloroplast is from a microalga selected from the group consisting of *Chlamydomonas reinhardtii, Dunaliella salina, Haematococcus pluvialis, Chlorella vulgaris, Acutodesmus obliquus*, and *Scenedesmus dimorphus*.

4. The chloroplast of claim 2, wherein the green algae is selected from the group consisting of *Chlamydomonas, Dunaliella, Haematococcus, Chlorella*, and *Scenedesmaceae*.

5. The chloroplast of claim 1, further wherein the chloroplast comprises at least two polynucleotides encoding at least two mammalian milk or colostrum polypeptides.

6. The chloroplast of claim 5, wherein the at least two mammalian milk or colostrum polypeptides comprise (i) osteopontin and (ii) mammary associated serum amyloid A3 (M-SAA3) and/or lactadherin.

7. The chloroplast of claim 5, wherein the at least two mammalian polypeptides comprises osteopontin and one or more mammalian milk or colostrum polypeptides selected from mammary associated serum amyloid A3 (M-SAA3), lactadherin, beta-lactoglobin, haptoglobin, IgG1, IgG2, IgA, IgM, IgD, lactoferrin, proline rich polypeptide (PRP), transforming growth factor (TGF)-β1, TGF-β2, insulin-like growth factor 1 (IGF-1), IGF-2, epidermal growth factor, heparin-binding epidermal growth factor-like growth factor, betacellulin, IL-6, IL-1β, IL 1ra, milk fat globule membrane (MFGM) proteins, serum albumin, glycomacropeptide, β-casein, κ-casein, αs1 casein, αs2-casein, γ-casein, superoxide dismutase, lactoperoxidase, alkaline phosphatase, platelet-activating factor-acetylhydroxylase, lipase, mucins, antimicrobial peptides, alpha-defensins, beta-defensins, cathelicidins, 14-3-3 protein zeta chain, 5-oxoprolinase, actin, beta-actin, adipose differentiation-related protein, albumin precursor, aldehyde dehydrogenase, ankyrin 3, ankyrin G, annexin 1, annexin A2, apolipoprotein A-I, apolipoprotein B, actin-related protein 3, ATP synthase, beta-2-microglobulin precursor; butyrophilin, actin filament capping protein; muscle Z-line, alpha 1; casein kinase 1, alpha 1; coronin, actin binding protein, 1A; CD36 antigen; Chitinase-like protein 1 (CLP-1); DEAD (Asp-Glu-Ala-Asp (SEQ ID NO:25)) box polypeptide 54; deleted in malignant brain tumors 1; diacylglycerol kinase kappa; endoplasmin precursor (GRP94); enolase 1; eukaryotic translation initiation factor 4, gamma 2; heart type fatty acid binding protein (MDGI); fetuin; fibrinogen alpha chain; fibrinogen beta chain precursor; fibrinogen gamma-B chain precursor; gene model 440; glucose regulated protein 58 kD; glutamate receptor, ionotropic, delta 1; glutathione S-transferase; glyceraldehyde-3-phosphate; dehydrogenase (GAPDH); glycerol-3-phosphate dehydrogenase 2; glycoprotein antigen MGP57/53; glycosylation-dependent cell adhesion molecule 1; guanine nucleotide binding protein, beta 2; H3 histone, family 3A; heat shock 70 kDa protein 8; heat shock 70 kD protein 5 ; heat shock protein 27; heat shock protein 70 kDa protein 1A; histone 2, H2ab; zinc finger protein 668; hypothetical/unnamed protein LOC51063; IRTA2; isocitrate dehydrogenase 1; keratin 9; keratin complex 2, basic, gene 6a; keratin, type I cytoskeletal 10; and KIAA1586 protein.

8. The chloroplast of claim 1, wherein the osteopontin polypeptide is from a mammal selected from the group consisting of human, canine, feline, bovine, porcine, ovine, and caprine.

9. The chloroplast of claim 1, wherein the polynucleotide encoding mammalian osteopontin comprises a polynucleotide having at least 90% sequence identity to a polynucleotide selected from the group consisting of SEQ ID NO:7, SEQ ID NO:17, SEQ ID NO:19 and SEQ ID NO:21.

10. The chloroplast of claim 5, wherein the two or more mammalian polypeptides are bioactive and phosphorylated at 50% or more of the amino acid positions that are phosphorylated in the mammalian peptide expressed from a mammalian cell.

11. A cell comprising the chloroplast of claim 1.

12. The cell of claim 11, wherein the cell is intact.

13. The cell of claim 11, wherein the cell is freeze-dried.

14. A method for producing one or more mammalian colostrum or milk proteins, comprising culturing the cell of claim 11.

15. A composition edible by a mammal and/or a chicken comprising one or more populations of cells of claim 11.

16. The composition of claim 15, wherein the composition is selected from a beverage, a food, a feed, a food supplement, and a nutraceutical.

17. The composition of claim 15, wherein the composition is selected from the group consisting of a compressed algal cake, an algal paste, and an algal powder.

18. The composition of claim 15, wherein the composition is freeze-dried, lyophilized, or spray-dried.

19. The cell of claim 11, further comprising a polynucleotide encoding mammary associated serum amyloid A3 (M-SAA3) integrated into the nuclear genome of the cell.

20. The chloroplast of claim 1, wherein the polynucleotide encoding mammalian osteopontin comprises a polynucleotide having at least 95% sequence identity to a polynucleotide selected from the group consisting of SEQ ID NO:7, SEQ ID NO:17, SEQ ID NO:19 and SEQ ID NO:21.

21. The cell of claim 11, wherein the cell is a microalgal cell.

22. The cell of claim 11, wherein the cell is from a green algae selected from the group consisting of *Chlamydomonas, Dunaliella, Haematococcus, Chlorella*, and *Scenedesmaceae*.

* * * * *